United States Patent
Thainashmuthu et al.

(10) Patent No.: US 11,427,542 B2
(45) Date of Patent: Aug. 30, 2022

(54) COMPOUNDS FOR TREATMENT OF CARDIAC ARRHYTHMIAS AND HEART FAILURE

(71) Applicant: Elex Biotech, Inc., Portland, OR (US)

(72) Inventors: Josephrajan Thainashmuthu, Fletcher, NC (US); Martha Sibrian-Vazquez, Portland, OR (US); Douglas Boatman, Petaluma, CA (US)

(73) Assignee: Elex Biotech, Inc., Portland, OR (US)

( * ) Notice: Subject to any disclaimer, the term of this patent is extended or adjusted under 35 U.S.C. 154(b) by 0 days.

(21) Appl. No.: 17/042,616

(22) PCT Filed: Mar. 28, 2019

(86) PCT No.: PCT/US2019/024694
§ 371 (c)(1),
(2) Date: Sep. 28, 2020

(87) PCT Pub. No.: WO2019/191502
PCT Pub. Date: Oct. 3, 2019

(65) Prior Publication Data
US 2021/0139429 A1   May 13, 2021

Related U.S. Application Data

(60) Provisional application No. 62/649,840, filed on Mar. 29, 2018.

(51) Int. Cl.
| | | |
|---|---|---|
| *C07C 211/49* | (2006.01) | |
| *C07C 217/88* | (2006.01) | |
| *C07D 213/74* | (2006.01) | |
| *A61P 9/06* | (2006.01) | |
| *A61P 9/04* | (2006.01) | |
| *C07C 229/64* | (2006.01) | |
| *C07C 309/24* | (2006.01) | |
| *C07D 209/44* | (2006.01) | |
| *C07D 215/12* | (2006.01) | |
| *C07D 217/04* | (2006.01) | |
| *C07D 231/56* | (2006.01) | |
| *C07D 257/04* | (2006.01) | |
| *C07D 271/06* | (2006.01) | |
| *C07D 295/13* | (2006.01) | |

(52) U.S. Cl.
CPC .............. *C07D 213/74* (2013.01); *A61P 9/04* (2018.01); *A61P 9/06* (2018.01); *C07C 211/49* (2013.01); *C07C 217/88* (2013.01); *C07C 229/64* (2013.01); *C07C 309/24* (2013.01); *C07D 209/44* (2013.01); *C07D 215/12* (2013.01); *C07D 217/04* (2013.01); *C07D 231/56* (2013.01); *C07D 257/04* (2013.01); *C07D 271/06* (2013.01); *C07D 295/13* (2013.01)

(58) Field of Classification Search
CPC ........................... C07C 211/49; C07C 217/88
See application file for complete search history.

(56) References Cited

U.S. PATENT DOCUMENTS

2009/0208557 A1   8/2009   Spada et al.

FOREIGN PATENT DOCUMENTS

| CN | 102 846 623 A | 1/2013 |
|---|---|---|
| JP | H 0841193 A | 2/1996 |
| WO | WO 2003/101490 A1 | 12/2003 |
| WO | WO 2007/008895 A1 | 1/2007 |
| WO | WO 2007/113596 A1 | 10/2007 |
| WO | WO 2010/055117 A1 | 5/2010 |
| WO | WO 2012/146526 A3 | 11/2012 |
| WO | WO 2015/085245 A1 | 6/2015 |
| WO | WO 2016/207785 A1 | 12/2016 |

OTHER PUBLICATIONS

Abramson et al., "Mechanism of Anthraquinone-induced Calcium Release from Skeletal Muscle Sacoplasmic Reticulum," *J Biol Chem* 263(35):18750-18758 (Dec. 15, 1988).
Fabiato, "Calcium-induced release of calcium from the cardiac sarcoplasmic reticulum," *Cell Physiology*, vol. 245, Issue 1, 14 pp. (Jul. 1, 1983).
Huang et al., "Discovery of Indolinone-Based Multikinase Inhibitors as Potential Therapeutics for Idiopathic Pulmonary Fibrosis," *ACS Medicinal Chemistry Letters*. vol. 8, pp. 1142-1147 (2017).
Hunt et al., "K201 (JTV519) suppresses spontaneous $Ca^{2+}$ release and [$^3$H]ryanodine binding to RyR2 irrespective of FKBP12.6 association," *Biochem J* 404, pp. 431-4438 (2007).
International Search Report and Written Opinion for related PCT/US2019/024694, dated Aug. 6, 2019 (27 pages).
Laver et al., "Three independent mechanisms contribute to tetracaine inhibition of cardiac calcium release channels," *Journal of Molecular and Cellular Cardiology*, vol. 51, No. 3, pp. 357-369 (May 11, 2011).

(Continued)

*Primary Examiner* — Shawquia Jackson
(74) *Attorney, Agent, or Firm* — Klarquist Sparkman, LLP

(57) ABSTRACT

This disclosure concerns compounds and a method for modulating the activity of calcium ion channels, including $Ca^{2+}$-induced (or $Ca^{2+}$-activated) calcium release channels and conformationally coupled calcium release channels such as ryanodine receptors. Some of the compounds have a structure according to formula I, or a stereoisomer, tautomer, hydrate, solvate, prodrug, or pharmaceutically acceptable salt thereof.

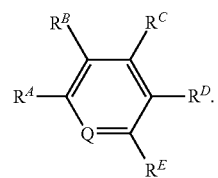

(I)

14 Claims, 22 Drawing Sheets

(56) References Cited

OTHER PUBLICATIONS

Marinov et al., "Non-Thiol Reagents Regulate Ryanodine Receptor Function by Redox Interactions That Modify Reactive Thiols," *Antioxid Redox Signal*, 9(5);609-621 (2007).

Nsumiwa et al., "Structure-activity relationships for ferriprotoporphyrin IX association and β-hematin inhibition by 4-aminoquinolines using experimental and ab initio methods," *Bioorganic & Medicinal Chemistry* 21(13):3738-3748, author manuscript, 36 pp. (Apr. 23, 2013).

Okombo et al., "Antischistosomal Activity of Pyrido[1,2-a]benzimidazole Derivatives and Correlation with Inhibition of [beta]-Hematin Formation," *ACS Infectious Diseases*. vol. 3, No. 6, (May 3, 2017), 29 pages.

Ongarora et al., "Antimalarial benzoheterocyclic 4-aminoquinolines: Structure-activity relationship, in vivo evaluation, mechanistic and bioactivation Studies," *Bioorganic & Medicinal Chemistry*, vol. 23, No. 17, pp. 5419-5432 (Sep. 1, 2015).

Rynearson et al., "2-Aminobenzoxazole ligands of the hepatitis C virus internal ribosome entry site," *Bioorganic & Medicinal Chemistry Letters*. vol. 24, No. 15, pp. 3521-3525, author manuscript, (Aug. 1, 2015).

Schneider et al., "Voltage dependent charge movement of skeletal muscle: a possible step in excitation-contraction coupling," *Nature* vol. 242, pp. 244-246 (Mar. 23, 1973).

Trimm et al., "Sulfhydryl oxidation induces rapid calcium release from sarcoplasmic reticulum vesicles," *J Biol Chem* 261(34);:6092-16098 (Dec. 5, 1986).

Wehrens et al., "Protection from Cardiac Arrhythmia Through Ryanodine Receptor-Stabilizing Protein Calstabin2," *Science* 304(5668):292-296 (Apr. 9, 2004).

Zhou et al., "Screening for inhibitors of the hepatitis C virus internal ribosome entry site RNA," *Bioorganic & Medicinal Chemistry*, 21(20):6139-6144, author manuscript (Apr. 2, 2013).

STN Database accession No. 1333745-16-6, Chemical Abstracts Service (Sep. 29, 2011).

STN Database accession No. 1622495-11-7, Chemical Abstracts Service (Sep. 12, 2014).

STN Database accession No. 1638367-57-3, Chemical Abstracts Service (Dec. 10, 2014).

STN Database accession No. 1940684-93-4, Chemical Abstracts Service (Jun. 28, 2016).

STN Database accession No. 2035045-41-9, Chemical Abstracts Service (Nov. 18, 2016).

STN Database accession No. 2035269-46-4, Chemical Abstracts Service (Nov. 21, 2016).

STN Database accession No. 2036101-94-5, Chemical Abstracts Service (Nov. 22, 2016).

STN Database accession No. 2038402-09-2, Chemical Abstracts Service (Nov. 27, 2016).

STN Database accession No. 2039200-84-3, Chemical Abstracts Service (Nov. 28, 2016).

| Entry | Formula | ID | Compound Structure | Plasma Stability 120 min (Mouse/rat/ human) % | Microsomal Stability 60 min (Mouse/Human) % | Cytotoxicity (HEK293/HepG2) μM |
|---|---|---|---|---|---|---|
| 1 | VII | EB3001 | 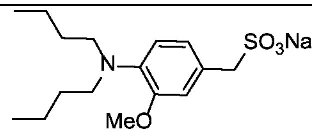 | 96.3/90.7/ 94.2 | 68.6/66.3 | >100/>100 |
| 2 | VII | EB3004 | 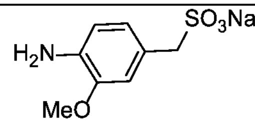 | --- | --- | >100/>100 |
| 3 | II | EB3017 | 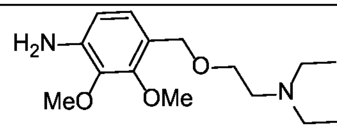 | 86.6/91.6/ 91.1 | | >100/>100 |
| 4 | IIID | 251 | 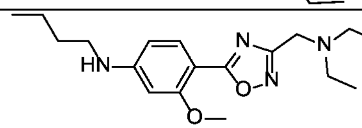 | --- | --- | --- |
| 5 | IIID | 252 | 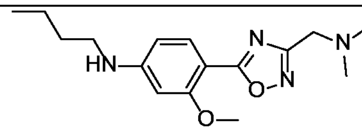 | --- | --- | --- |
| 6 | IIID | 253 | 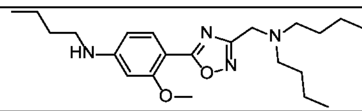 | 100.3/97.6 (mouse/ human) | 1.0/71.4 | --- |

FIG. 17A

| Entry | Formula | ID | Compound Structure | Plasma Stability 120 min (Mouse/rat/ human) % | Microsomal Stability 60 min (Mouse/Human) % | Cytotoxicity (HEK293/HepG2) μM |
|---|---|---|---|---|---|---|
| 7 | IIID | 254 | 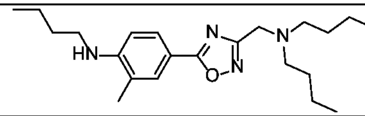 | --- | --- | --- |
| 8 | II | EB3019 | 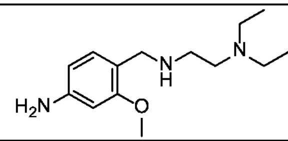 | 94.4/78.6/ 89.0 | 74.8/88.6 | >33.3 (tox @ 100) |
| 9 | II | EB3021 | 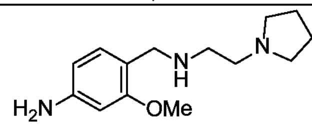 | 84.9/93.6/ 66.3 | 83.1/78.2 | >33.3 (tox @ 100) |
| 10 | II | EB3022 | 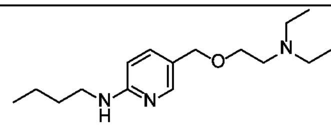 | 82.7/93.1/96 | 30.76/83.44 | >100/>100 |
| 11 | VII | EB3005 | 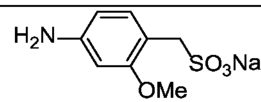 | 112/38.0/ 61.2 | 102.6/106.8 | >100/>100 |
| 12 | IIIA | EB3007 | 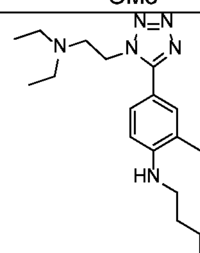 | --- | 17.0/43.2 | 41.7/34.04 |

FIG. 17B

| Entry | Formula | ID | Compound Structure | Plasma Stability 120 min (Mouse/rat/human) % | Microsomal Stability 60 min (Mouse/Human) % | Cytotoxicity (HEK293/HepG2) µM |
|---|---|---|---|---|---|---|
| 13 | IIIA | EB3008 | 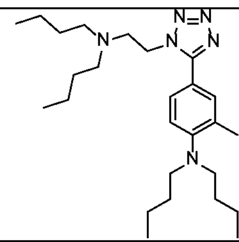 | 52.8/68.9/66 | N/A/NA | >100/>100 |
| 14 | VIB | EB3009 | 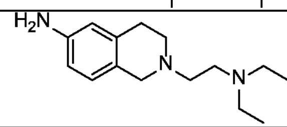 | 85.9/93.4/91.6 | 85.77/83.32 | >100/>100 |
| 15 | IV | EB3010 | 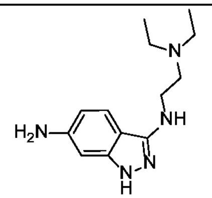 | --- | 85.77/83.32 | >33.3/>100 |
| 16 | IV | EB3012 | 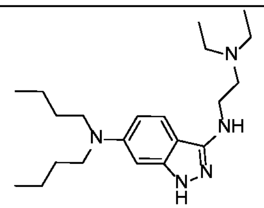 | --- | 2.51/23.76 | --- |

FIG. 17C

| Entry | Formula | ID | Compound Structure | Plasma Stability 120 min (Mouse/rat/human) % | Microsomal Stability 60 min (Mouse/Human) % | Cytotoxicity (HEK293/HepG2) µM |
|---|---|---|---|---|---|---|
| 17 | VA | EB3011 | 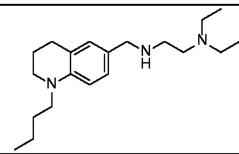 | -- | 1.13/24.67 | -- |
| 18 | = | EB3025 | 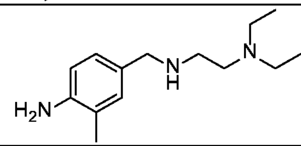 | 90.4/90.3/93.6 | 108.99/71.04 | >100/>100 |
| 19 | = | EB3053 | 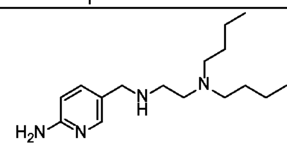 | 83.4/92.4/90.1 | -- | >100/>100 |
| 20 | = | EB3056 | 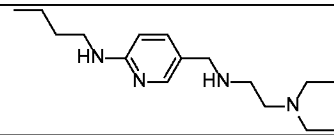 | 92.2/89.6/93.3 | -- | >100/>100 |
| 21 | = | EB3057 | 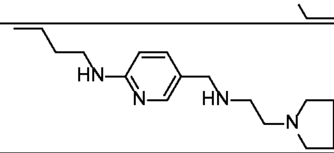 | 92.2/93.1/92.0 | -- | >100/>100 |
| 22 | VIA | EB3059 | 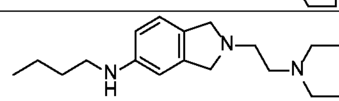 | 55.2/83.5/84.2 | -- | 31.49/30.55 |

FIG. 17D

| Entry | Formula | ID | Compound Structure | Plasma Stability 120 min (Mouse/rat/ human) % | Microsomal Stability 60 min (Mouse/Human) % | Cytotoxicity (HEK293/HepG2) μM |
|---|---|---|---|---|---|---|
| 23 | VIB | EB3060 | 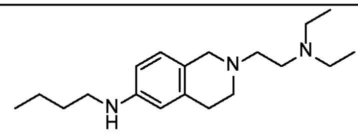 | 71.7/86.5/ 88.5 | --- | 117.27/96.12 |
| 24 | VIB | EB3061 | 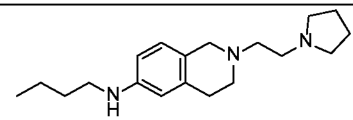 | --- | --- | --- |
| 25 | VIA | EB3064 | 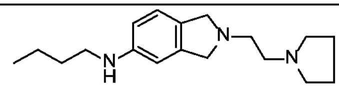 | --- | --- | --- |
| 26 | | tetracaine (control) | 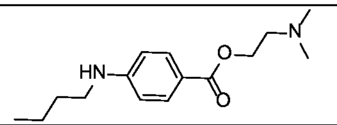 | --- | --- | >50 / >50 |
| 27 | | 4-MmC (control) | 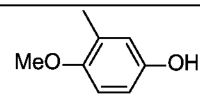 | --- | --- | >50 / >50 |
| 28 | | K201 (control) | 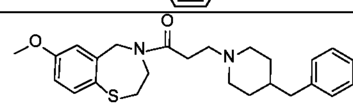 | --- | 0%/0% | 35 / 29 |
| 29 | | EL20 | 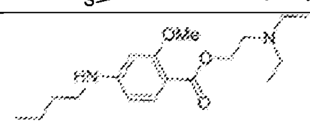 | --- | --- | >50 / >50 |

FIG. 17E

| Entry | Formula | ID | Compound Structure | In vitro Ca²⁺ Spark screen | $Ca^{2+}$ Spark $IC_{50}$ nM | In vivo CPVT screen/$ED_{50}$ Low & High Dose µg/Kg |
|---|---|---|---|---|---|---|
| 1 | VII | EB3001 | 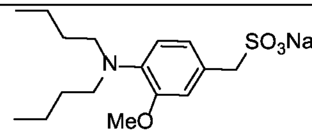 | Active | 5.8 | -- |
| 2 | VII | EB3004 | 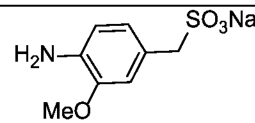 | Not Active | -- | -- |
| 3 | II | EB3017 | 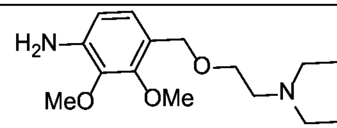 | Not Active | -- | -- |
| 4 | IIID | 251 | 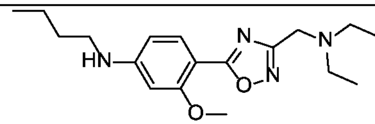 | Active | 210 | -- |
| 5 | IIID | 252 | 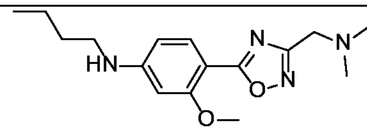 | Not Active | -- | -- |
| 6 | IIID | 253 | 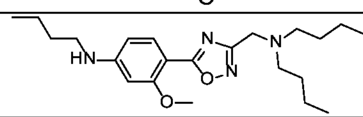 | Active | 100 | -- |

FIG. 18A

| Entry | Formula | ID | Compound Structure | In vitro Ca²⁺ Spark screen | Ca²⁺ Spark IC$_{50}$ nM | In vivo CPVT screen/ED$_{50}$ Low & High Dose µg/Kg |
|---|---|---|---|---|---|---|
| 7 | IIID | 254 | 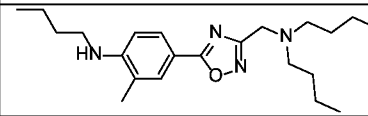 | Active | -- | -- |
| 8 | II | EB3019 | 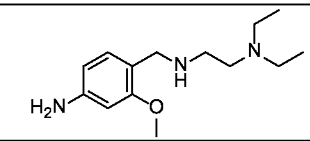 | Active | 100 | 0.95&9.5 |
| 9 | II | EB3021 | 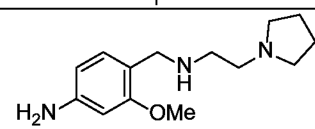 | Active | 21 | 1.36 |
| 10 | II | EB3022 | 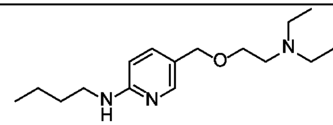 | Not Active | -- | -- |
| 11 | VII | EB3005 | 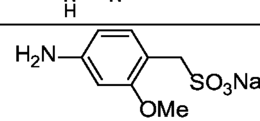 | Active | 100 | 0.32&3.2 |
| 12 | IIIA | EB3007 | 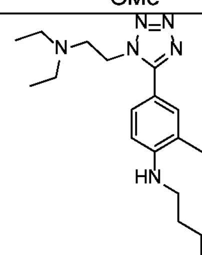 | Active | 15 | -- |

| Entry | Formula | ID | Compound Structure | In vitro Ca²⁺ Spark screen | Ca²⁺ Spark IC$_{50}$ nM | In vivo CPVT screen/ED$_{50}$ Low & High Dose μg/Kg |
|---|---|---|---|---|---|---|
| 13 | IIIA | EB3008 | 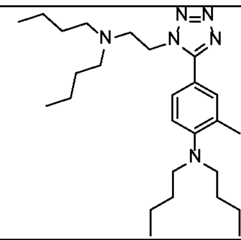 | Active | 252 | -- |
| 14 | VIB | EB3009 | 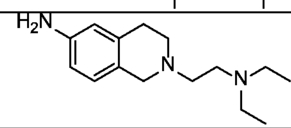 | Not Active | -- | -- |
| 15 | IV | EB3010 | 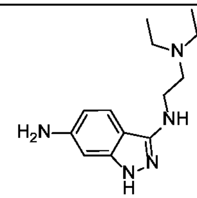 | Not Active | -- | -- |
| 16 | IV | EB3012 | 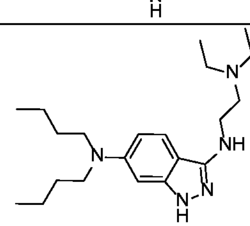 | Not Active | -- | -- |

| Entry | Formula | ID | Compound Structure | In vitro Ca²⁺ Spark screen | Ca²⁺ Spark IC$_{50}$ nM | In vivo CPVT screen/ED$_{50}$ Low & High Dose µg/Kg |
|---|---|---|---|---|---|---|
| 17 | VA | EB3011 | 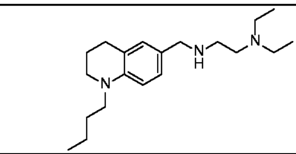 | Not Active | -- | -- |
| 18 | II | EB3025 | 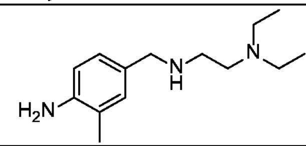 | Not Active | -- | -- |
| 19 | II | EB3053 | 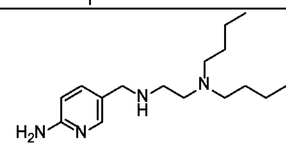 | Not Active | -- | -- |
| 20 | II | EB3056 | 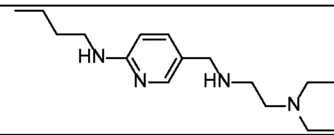 | Not Active | -- | -- |
| 21 | II | EB3057 | 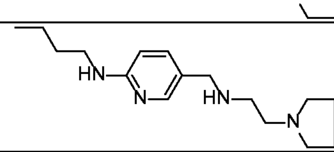 | Not Active | -- | -- |
| 22 | VIA | EB3059 | 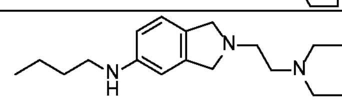 | Active | 88 | -- |

FIG. 18D

| Entry | Formula | ID | Compound Structure | In vitro Ca²⁺ Spark screen | Ca²⁺ Spark IC$_{50}$ nM | In vivo CPVT screen/ED$_{50}$ Low & High Dose µg/Kg |
|---|---|---|---|---|---|---|
| 23 | VIB | EB3060 | 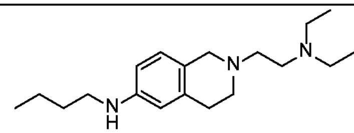 | Not Active | -- | -- |
| 24 | VIB | EB3061 | 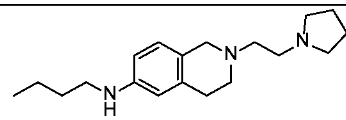 | Not Active | -- | -- |
| 25 | VIA | EB3064 | 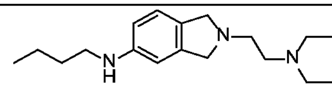 | -- | -- | -- |
| 26 | | tetracaine (control) | 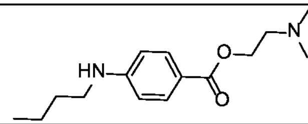 | -- | 60,000–100,000 | -- |
| 27 | | 4-MmC (control) | 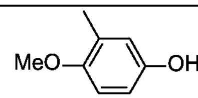 | -- | 2,180 | -- |
| 28 | | K201 (control) | 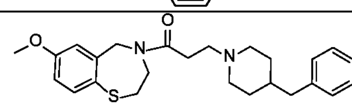 | -- | 7,730 | 500 |
| 29 | | EL20 | 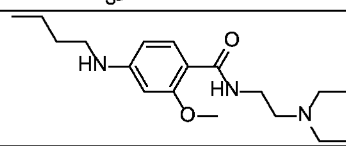 | Active | 35 | 2.5/TBD |

COMPOUNDS FOR TREATMENT OF CARDIAC ARRHYTHMIAS AND HEART FAILURE

CROSS REFERENCE TO RELATED APPLICATIONS

This is the U.S. National Stage of International Application No. PCT/US2019/024694, filed Mar. 28, 2019, which was published in English under PCT Article 21(2), which in turn claims the benefit of U.S. Provisional Application No. 62/649,840, filed Mar. 29, 2018, each of which is incorporated herein in its entirety.

ACKNOWLEDGMENT OF GOVERNMENT SUPPORT

This invention was made with government support under Grant No. HL114206, awarded by the National Institutes of Health. The government has certain rights in the invention.

FIELD

This disclosure concerns compounds and embodiments of a method for using such compounds to modulate the activity of calcium ion channels, including $Ca^{2+}$-induced (or $Ca^{2+}$-activated) calcium release channels and conformationally coupled calcium release channels such as ryanodine receptors.

BACKGROUND

The sarcoplasmic reticulum (SR) is a sub-cellular organelle responsible for regulating the $Ca^{2+}$ concentration in the cytosol of muscle fibers (Hasselbach and Makinose, *Biochem Biophys Res Commun* 7, 132-136 (1962)). By ATP hydrolysis, the SR network lowers the free $Ca^{2+}$ concentration in the space surrounding the myofibrils to sub-micromolar levels, pumping $Ca^{2+}$ into the lumen of the SR. The reduction of myoplasmic free $Ca^{2+}$ concentration leads to muscle relaxation.

Muscle contraction is initiated by an action potential at the cell surface membrane. This depolarization propagates down the transverse (T) tubules, which in turn triggers the release of $Ca^{2+}$ stored in the SR and contraction. More particularly, calcium release channels (CRCs) in the SR called ryanodine receptors (RyRs) open and release $Ca^{2+}$ from the SR into the intracellular cytoplasm of the cell. $Ca^{2+}$ release into the cytoplasm from the SR increases cytoplasmic $Ca^{2+}$ concentration. Open probability (Po) of the RyR receptor refers to the likelihood that the RyR channel is open at any given moment, and therefore capable of releasing $Ca^{2+}$ into the cytoplasm from the SR.

There are three types of ryanodine receptors, all of which are highly-related $Ca^{2+}$ channels: RyR1, RyR2, and RyR3. RyR1 is found predominantly in skeletal muscle as well as other tissues, while RyR2 is found predominantly in the heart as well as other tissues, and RyR3 is found in the brain as well as other tissues. The RyR channels are formed by four RyR polypeptides in association with four FK506 binding proteins (FKBPs), specifically FKBP12 (calstabin1) and FKBP12.6 (calstabin2). Calstabin1 binds to RyR1, calstabin2 binds to RyR2, and calstabin1 binds to RyR3. The FKBP proteins (calstabin1 and calstabin2) bind to the RyR channel (one molecule per RyR subunit), stabilize RyR-channel functioning, and facilitate coupled gating between neighboring RyR channels, thereby preventing abnormal activation of the channel during a closed state.

Recent advances have been made toward understanding the 3-dimensional structure of the ryanodine receptor (RyR)/$Ca^{2+}$ release protein, and the possible functional role of other junctional SR proteins in excitation contraction coupling (ECC) in skeletal muscle. As such, ECC differs in skeletal and cardiac muscle. In skeletal muscle, there appears to be a mechanical coupling between the dihydropyridine receptor (DHPR) found in the T-tubule membrane and the CRC or RyR found at the terminal end of the SR (Schneider and Chandler, *Nature* 242, 244-246 (1973)). On the other hand, in cardiac muscle, $Ca^{2+}$ enters the cell during the action potential through the DHPR, and initiates $Ca^{2+}$ release from the SR via a mechanism known as $Ca^{2+}$-induced $Ca^{2+}$ release (Fabiato, *Am J Physiol* 245, C1-14 (1983)).

A number of associated proteins regulate the activity of the SR ryanodine receptors. The DHPR and RyR appear to form a hub for a large macromolecular complex, which includes triadin and calsequestrin (on the luminal face of the SR), FKBP12 (skeletal muscle) and FKBP12.6 (cardiac muscle), calmodulin, Ca'-CaM kinase (skeletal muscle), and protein kinase A (PKA) (cardiac muscle). Defective RyR-FKBP12.6 association has been implicated in heart failure, cardiomyopathy, cardiac hypertrophy, and exercise induced sudden cardiac death. PKA phosphorylation of the cardiac RyR2 may result in dissociation of FKBP12.6 from the $Ca^{2+}$ release channel, which results in an increased channel open probability (Po), increased sensitivity to activation by $Ca^{2+}$, and destabilization of the CRC (Wehrens et al., *Science* 304, 292-296 (2004)). Alternatively, it has been proposed that abnormal $Ca^{2+}$ handling by calsequestrin may lead to an increased $Ca^{2+}$ leak and cardiac arrhythmias. The cardioprotective agent K201 (also known as JTV519) and the antioxidant edaravone appear to correct the defective FKBP12.6 control of RyR2 and improve function. However, the mechanism of action of K201 is controversial. One report has shown that K201 suppresses spontaneous $Ca^{2+}$ release in ventricular myocytes independent of the presence of the FKBP12.6 protein, suggesting that the mode by which K201 decreases the $Ca^{2+}$ leak from cardiac SR does not involve the FKBP12.6 protein (Hunt et al., *Biochem J* 404, 431-438 (2007)).

In addition, CRCs from both cardiac and skeletal muscle SR are rich in thiol groups, and therefore, are strongly regulated by thiol reactive agents. Oxidation of these thiol groups increases $Ca^{2+}$ release rates from SR vesicles, increases open probability of the reconstituted CRC, and increases high affinity ryanodine binding to the SR, while reducing the disulfide(s) formed results in decreased activity (Trimm et al., *J Biol Chem* 261, 16092-16098 (1986); Abramson et al., *J Biol Chem* 263, 18750-18758 (1988)). There are also a large number of non-thiol reagents known to either activate or inhibit RyR1 and/or RyR2. Among those compounds that activate the RyR/CRC are methylxanthines such as caffeine, plant alkaloids such as ryanodine, polyamines such as polylysine, quinone such as doxorubicin, and phenols such as 4-chloro-m-cresol (4-CmC). Among the non-thiol RyR/CRC inhibitors are local anesthetics such as tetracaine and procaine, and the poly-unsaturated fatty acids such as docosahexaenoic acid (DHA). These reagents are physiologically and pharmacologically diverse, and their mode of action was somewhat controversial (Marinov et al., *Antioxid Redox Signal* 9, 609-621 (2007)).

In the normal heart, Ca$^{2+}$ release from the SR via RyR2 is a tightly regulated process that involves discrete release of Ca$^{2+}$ during systole, and cessation of Ca$^{2+}$ release during diastole. For the timely rhythmic release of Ca2+ from RyR2, the channel must open in response to a cytoplasmic Ca$^{2+}$ flux, but remain closed during diastolic SR Ca$^{2+}$ filling. Destabilization of RyR2 may occur as a result of genetic mutations (e.g., Catecholaminergic Polymorphic Ventricular Tachycardia, or CPVT) or acquired modifications (e.g., oxidation, nitrosylation, phosphorylation). The common consequence of both genetic and acquired modifications in RyR2 is an increased propensity towards pathologic SR Ca$^{2+}$ release during diastole, which can initiate cardiac arrhythmias and/or heart failure.

SUMMARY

Embodiments of compounds and methods for modulating the activity of calcium ion channels are disclosed. A compound according to formula I, or a stereoisomer, tautomer, pharmaceutically acceptable salt, hydrate, or solvate thereof, has a structure:

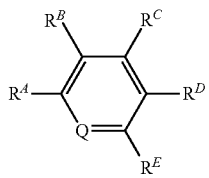
(I)

wherein R$^A$ is —N(R$^1$)R$^2$ and R$^B$ is H, aliphatic, —O-aliphatic, —S-aliphatic, —O—C(O)-aliphatic, or halogen, or R$^A$ is N(R$^1$) or —CH$_2$N(R$^1$)— and R$^A$ together with R$^B$ forms a 5- or 6-membered heteroaliphatic or heteroaryl ring; R$^C$ is H, aliphatic, —S-aliphatic, or —O—C(O)-aliphatic, and R$^D$ is substituted aliphatic or —Y—X—(CR$^7_2$)$_m$—N(R$^4$)R$^5$, or R$^C$ and R$^D$ together form a 5- or 6-membered heteroaliphatic or heteroaryl ring, such as a 5- or 6-membered nitrogen-containing heteroaliphatic or heteroaryl ring substituted with —X—(CR$^7_2$)$_m$—N(R$^4$)R$^5$; R$^E$ is H, aliphatic, —O-aliphatic, —S-aliphatic, —O—C(O)-aliphatic, or halogen; Q is N or C—R$^3$; X is N(R$^6$), O, C(O), —S(O$_2$)O—, —OS(O$_2$)—, —P(O)(OH)O—, —OP(O)(OH)$_3$, —N(H)—C(H)(CF$_3$)— or —C(H)(CF$_3$)—N(H)—, or X is absent; Y is —(CR$^7_2$)$_m$— or a divalent azole ring; R$^1$ and R$^2$ independently are H or aliphatic; R$^3$ is H, aliphatic, —O-aliphatic, or —S-aliphatic; R$^4$ and R$^5$ independently are H, aliphatic, aryl, or heteroaryl, or R$^4$ and R$^5$ together with N form a heterocycloaliphatic or heteroaryl ring; R$^6$ is H or aliphatic; each R$^7$ independently is H, halogen, or aliphatic; and m and n independently are integers from 1 to 10. In some embodiments, at least one of the following conditions applies: (i) if Q is C—R$^3$, then at least one of R$^B$, R$^C$, R$^E$, and R$^3$ is other than H, or (ii) if R$^D$ is —Y—X—(CH$_2$)$_m$—N(R$^4$)R$^5$ where X is absent, then Y is not —(CH$_2$)$_n$—, or (iii) the compound includes —Y—X—(CR$^7_2$)$_m$—N(R$^4$)R$^5$ or-X —(CR$^7_2$)$_m$—N(R$^4$)R$^5$, where X is present, or (iv) if Y is a divalent azole ring, then X is absent, or (v) if R$^4$ and R$^5$ together with N form a heterocycloaliphatic or heteroaryl ring and Q is C—R$^3$, then at least of one of R$^B$, R$^C$, R$^E$, and R$^3$ is other than H, or at least one of R$^1$ and R$^2$ is other than H or —CH$_3$.

In some embodiments, the compound has a structure according to one of formulas II, III, IV, V, VI, or VII:

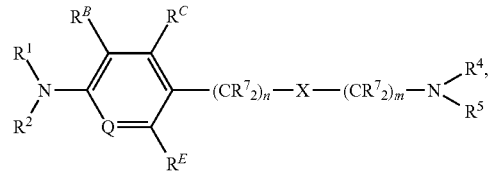
(II)

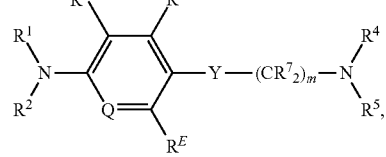
(III)

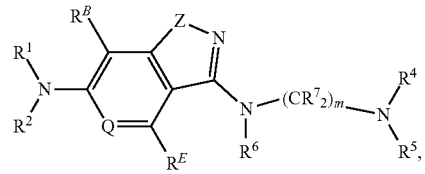
(IV)

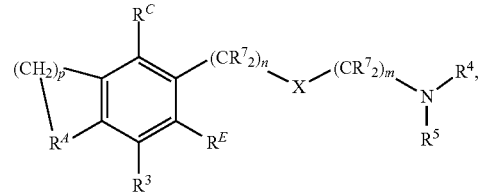
(V)

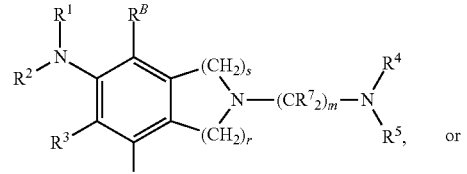
(VI)

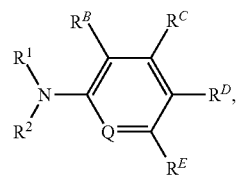
(VII)

wherein R$^A$ is N(R$^1$) or —CH$_2$N(R$^1$)—; R$^B$ is H, aliphatic, —O-aliphatic, —S-aliphatic, or halogen; R$^C$ is H or aliphatic; R$^D$ is —(CH$_2$)$_q$NH$_2$, —(CH$_2$)$_q$OH, or —(CH$_2$)$_q$SO$_3$M where q is an integer from 1 to 10 and M is a monatomic cation; X is N(R$^6$), O, C(O), —S(O$_2$)O—, —OS(O$_2$)—, —P(O)(OH)O—, —OP(O)(OH)$_3$, —N(H)—C(H)(CF$_3$)— or —C(H)(CF$_3$)—N(H)—; Y is an azole; Z is O, N(H), or CH$_2$; p is 1, 2, or 3 when R$^A$ is N(R$^1$), or p is 1 or 2 when R$^A$ is —CH$_2$N(R$^1$)—; q is an integer from 1 to 10; and r is 1 or 2, s is 1 or 2, and r+s=2 or 3. R$^1$-R$^3$, R$^6$, and R$^7$ are as previously defined. Embodiments of a pharmaceutical composition include a therapeutically effective amount of at least one compound as disclosed herein, or a pharmaceutically acceptable salt thereof, and at least one pharmaceutically acceptable additive, including a second therapeutic agent.

A method for modulating activity of a calcium ion channel includes contacting the calcium ion channel with an effective amount of a compound as disclosed herein, or a pharmaceutically acceptable salt, solvate, hydrate, or prodrug thereof. In some embodiments, contacting the calcium ion channel with the compound inhibits activity of the calcium ion channel. In certain embodiments, the calcium ion channel is a ryanodine receptor, such as RyR2. In any or all of the foregoing embodiments, contacting the calcium ion channel may be performed in vivo. In some embodiments, contacting the calcium ion channel comprises administering an effective amount of the compound, or pharmaceutically acceptable salt, solvate, hydrate, or prodrug thereof, to a subject identified as having, or being at risk of having, a cardiac arrhythmia or heart failure. Administering the effective amount of the compound, or pharmaceutically acceptable salt, solvate, hydrate, or prodrug thereof, may comprise administering an amount of a pharmaceutical composition comprising the effective amount of the compound to the subject.

A method for ameliorating at least one sign or symptom of a cardiac arrhythmia or heart failure includes administering one or more therapeutically effective doses of a compound as disclosed herein, or a pharmaceutically acceptable salt thereof, over an effective period of time to a subject identified as having, or being at risk of having, a cardiac arrhythmia or heart failure, thereby ameliorating at least one sign or symptom of the cardiac arrhythmia or heart failure. Administering the therapeutically effective dose of the compound, or pharmaceutically acceptable salt, solvate, hydrate, or prodrug thereof, may comprise administering an amount of a pharmaceutical composition comprising the therapeutically effective dose of the compound to the subject. In one embodiment, administering is performed by an oral, parenteral, transmucosal, or transdermal route. In an independent embodiment, administering is performed by an oral, intramuscular, subcutaneous, intravenous, or intra-arterial route.

The foregoing and other objects, features, and advantages of the invention will become more apparent from the following detailed description, which proceeds with reference to the accompanying figures.

BRIEF DESCRIPTION OF THE DRAWINGS

FIGS. 17A-17E are tables showing structures, plasma stability, microsomal stability, and cytotoxicity data of several disclosed compounds within the scope of the present disclosure.

FIGS. 18A-18E are tables showing structures, $Ca^{2+}$ spark data and in vivo CPVT screen/$ED_{50}$ data of several disclosed compounds within the scope of the present disclosure.

DETAILED DESCRIPTION

Figure 1:
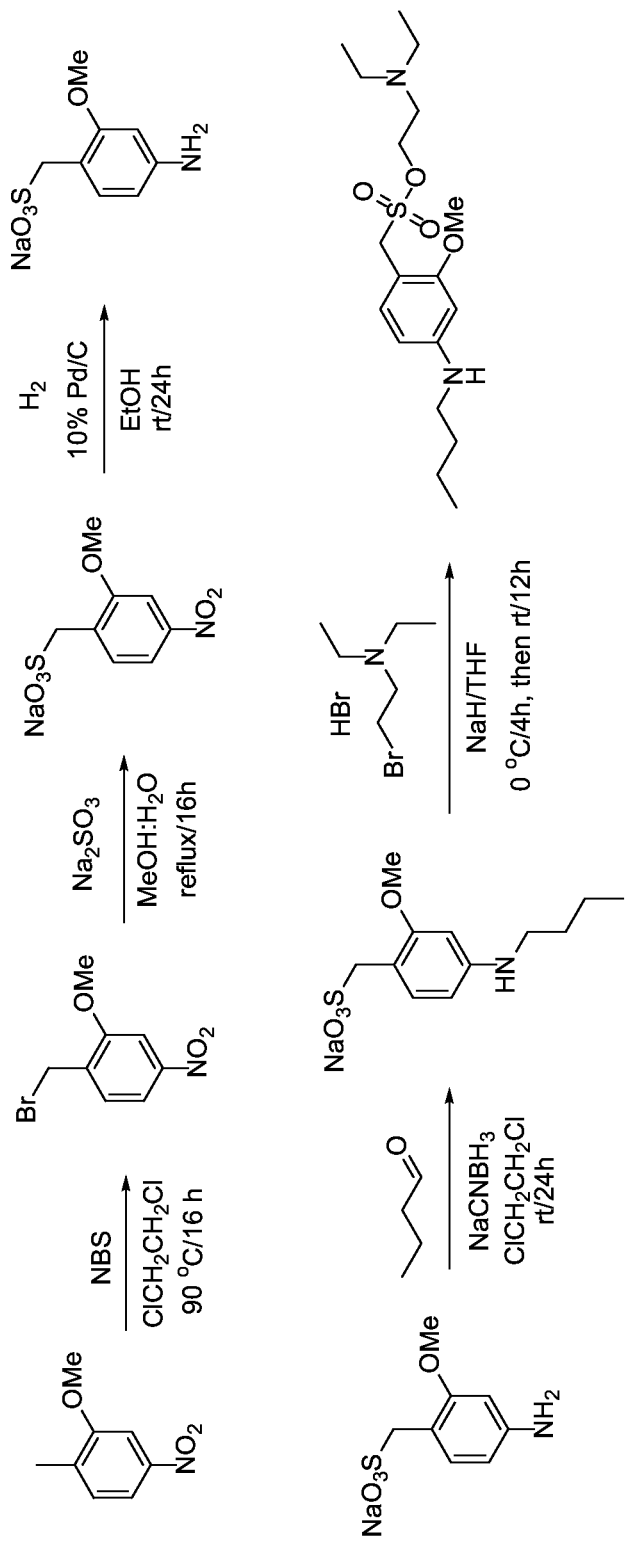
FIG. 1 is an exemplary synthetic scheme for preparing compounds according to formula II, with the particular synthesis illustrating preparing an exemplary compound according to formula II where X is $SO_3$ and Q is CH.
Figure 2:
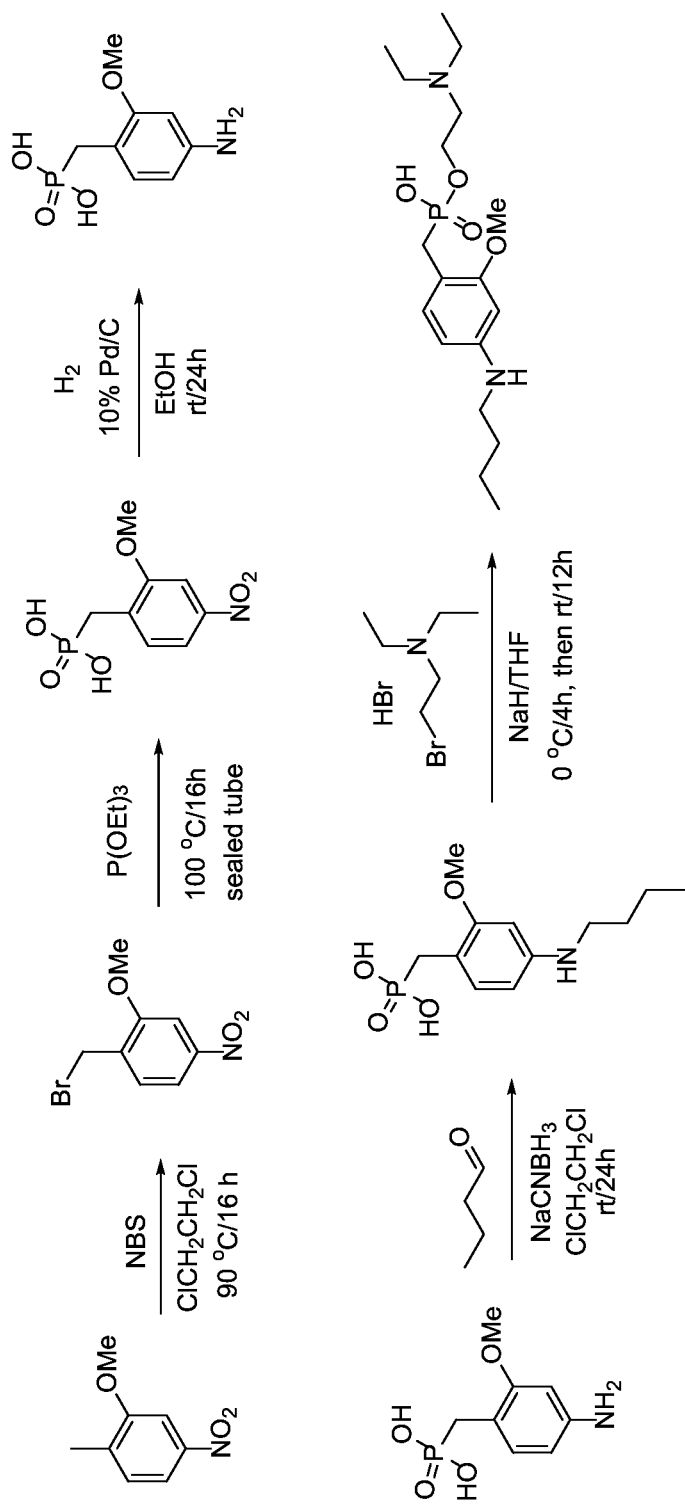
FIG. 2 is an exemplary synthetic scheme for preparing compounds according to formula II, with the particular synthesis illustrating preparing an exemplary compound according to formula II where X is $PO_2OH$ and Q is CH.
Figure 3:
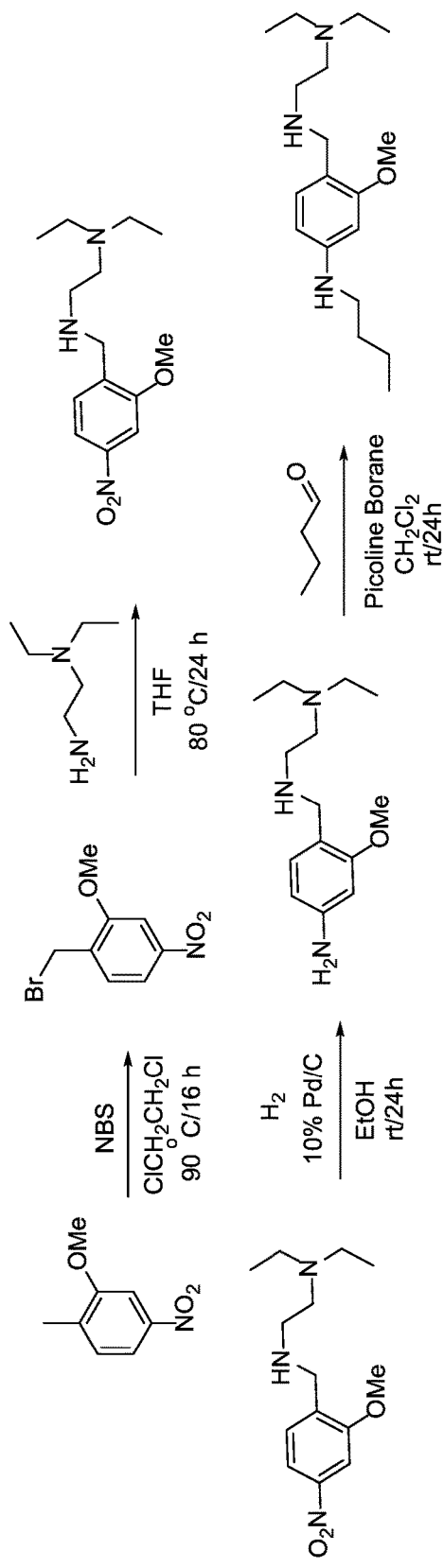
FIG. 3 is an exemplary synthetic scheme for preparing compounds according to formula II, with the particular synthesis illustrating preparing an exemplary compound according to formula II where X is NH and Q is CH.
Figure 4:
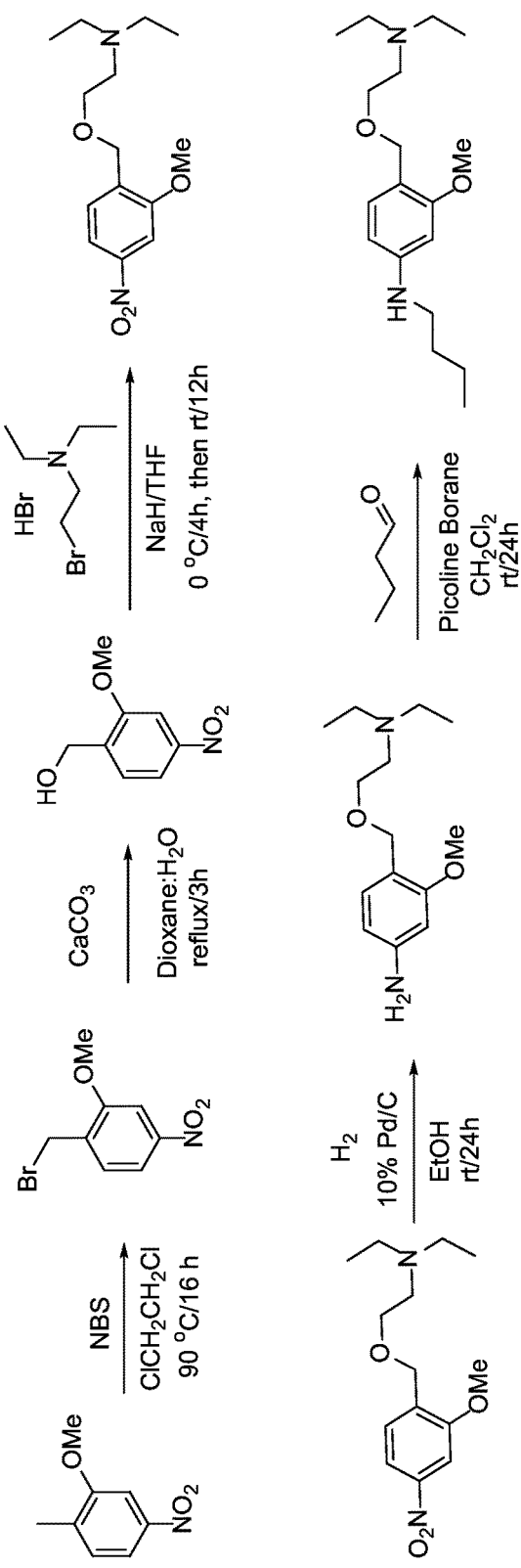
FIG. 4 is an exemplary synthetic scheme for preparing compounds according to formula II, with the particular synthesis illustrating preparing an exemplary compound according to formula II where X is O and Q is CH.
Figure 5:
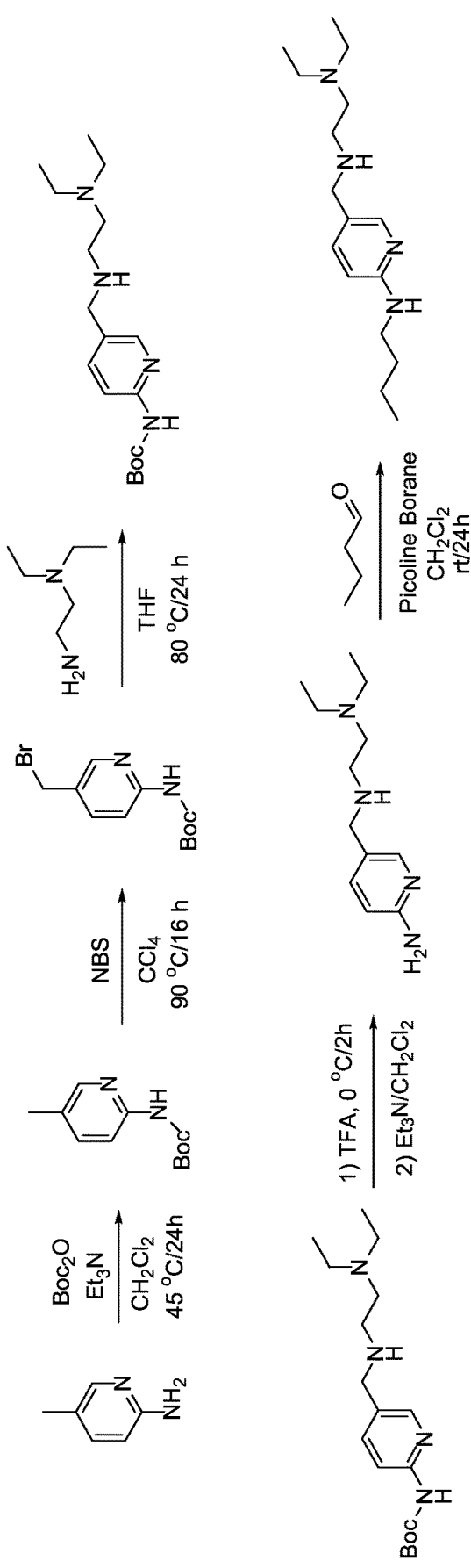
FIG. 5 is an exemplary synthetic scheme for preparing compounds according to formula II, with the particular synthesis illustrating preparing an exemplary compound according to formula II where X is NH and Q is N.
Figure 6:
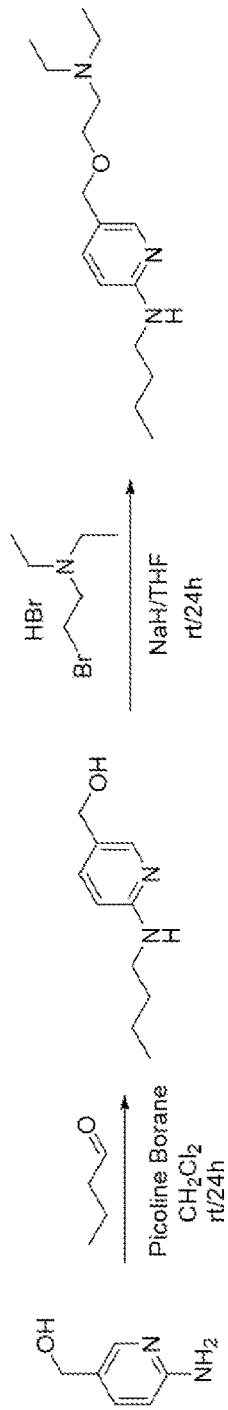
FIG. 6 is an exemplary synthetic scheme for preparing compounds according to formula II, with the particular synthesis illustrating preparing an exemplary compound according to formula II where X is O and Q is N.
Figure 7:
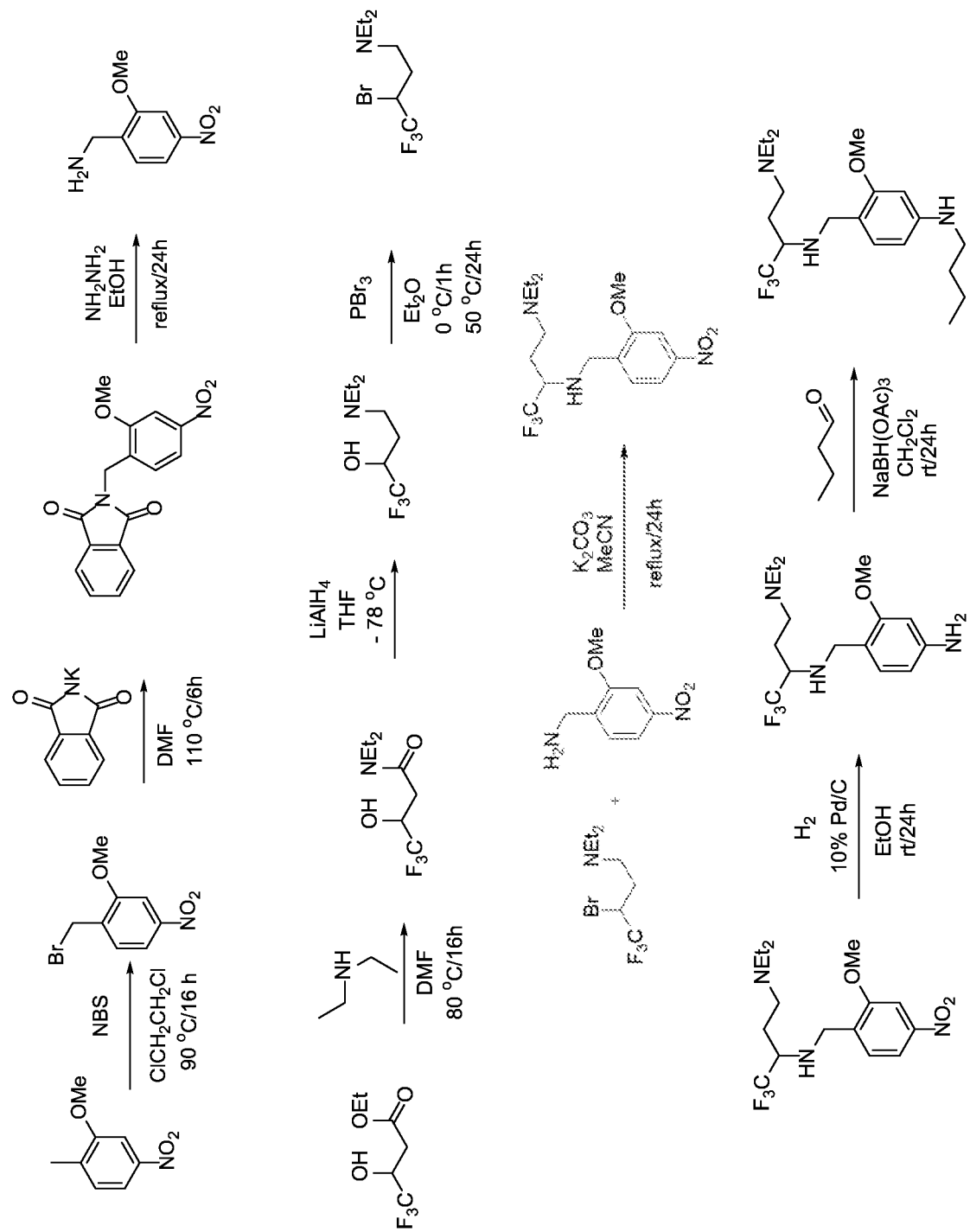
FIG. 7 is an exemplary synthetic scheme for preparing compounds according to formula II, with the particular synthesis illustrating preparing an exemplary compound according to formula II where X is N(H)—C(H)(CF$_3$) and Q is CH.

Disclosed herein are embodiments of compounds and a method for modulating the activity of calcium ion channels, including $Ca^{2+}$-induced (or $Ca^{2+}$-activated) calcium release channels and conformationally coupled calcium release channels, such as ryanodine receptors (RyR). RyR2 plays an important role during excitation-contraction coupling. The inventors have discovered that antiarrhythmic compounds targeting the RyR2 channel complex do not interfere with systolic SR $Ca^{2+}$ release. At the same time, inhibition of diastolic SR $Ca^{2+}$ release is a desirable feature of compounds that might prevent arrhythmias Some embodiments of the disclosed compounds have enhanced electron donor properties compared to known antiarrhythmic compounds that target RyR2 while being highly effective in decreasing the SR $Ca^{2+}$ leak associated with ventricular arrhythmias.

Some embodiments of the disclosed compounds and/or methods may inhibit or decrease intracellular calcium release, including calcium release in muscle cells (e.g., from SR in skeletal or cardiac muscle cells). These compounds and/or methods can include down-regulating or inhibiting the activity of calcium release channels, such as ryanodine receptors. Certain embodiments of the disclosed compounds and/or methods may change the redox potential of reactive thiols on ryanodine receptors in cells of a subject. Such redox potential changes can be achieved by modifying the thiol/disulfide balance within ryanodine receptors in cells of a subject, particularly, mammalian cells (Xia et al., *J Biol Chem* 275, 36556-36561 (2000)). Some embodiments of the disclosed compounds and/or methods may be useful for treating or reducing the risk of a ryanodine receptor (RyR) associated disease, disorder, or condition in a subject. In particular, the RyR-associated disorder, disease, or condition can be a cardiac or skeletal muscle condition, disorder, or disease. For example, the compounds according to the present disclosure may be used to treat CPVT arrhythmias, (e.g., by targeting one or more of RyR1, RyR2, and RyR3), or ventricular arrhythmias, atrial arrhythmias, heart failure, skeletal muscle fatigue, and cardiac disease linked to diabetes, and hypertension.

I. DEFINITIONS AND ABBREVIATIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, temperatures, times, and so forth, as used in the specification or claims are to be understood as being modified by the term "about." As used herein, the term "about" or the symbol "~" refers to a ±10% variation from the nominal value unless otherwise indicated or inferred. Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

At various places in the present specification, substituents are disclosed in groups or in ranges. It is specifically intended that the description include each and every individual subcombination of the members of such groups and ranges. For example, the term "C1-05 alkyl" is specifically intended to individually disclose C1, C2, C3, C4, C5, C1-05, C1-C4, C1-C3, C1-C2, C2-05, C2-C4, C2-C3, C3-05, C3-C4, and C4-C5 alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The presently disclosed compounds also include all isotopes of atoms present in the compounds, which can include, but are not limited to, deuterium, tritium, $^{18}$F, $^{14}$C, etc.

Aliphatic: A substantially hydrocarbon-based compound or moiety (e.g., $C_6H_{13}$, for a hexane moiety), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group). Exemplary substituents include, but are not limited to, alkyl, alkenyl, alkynyl, alkoxy, alkylamino, alkylthio, acyl, aldehyde, amide, amino, aminoalkyl, aryl, arylalkyl, carboxyl, cyano, cycloalkyl, dialkylamino, halo, haloaliphatic, heteroaliphatic, heteroaryl, heterocycloaliphatic, hydroxyl, oxo, sulfonamide, sulfhydryl, thioalkoxy, or other functionality.

Alkyl: A hydrocarbon group having a saturated carbon chain. The chain may be cyclic, branched or unbranched. Examples, without limitation, of alkyl groups include $C_1$-$C_{10}$ alkyl groups, such as methyl, ethyl, propyl (e.g., n-propyl and isopropyl), butyl (e.g., n-butyl, isobutyl, sec-butyl, tert-butyl), pentyl, hexyl, heptyl, octyl, nonyl and decyl. Cyclic alkyl groups such as cyclopropyl, cyclobutyl, cyclopentyl, and the like are also included. Unless expressly referred to as an "unsubstituted alkyl," an alkyl group can either be unsubstituted or substituted.

Alkylsulfanyl: A chemical functional group —SR where R is an alkyl group, such as a $C_1$-$C_{10}$ alkyl group.

Aminoalkyl: A chemical functional group —RNR'R" where R is an alkyl group, such as a $C_1$-$C_{10}$ alkyl group, and R' and R" independently are hydrogen or alkyl, such as $C_1$-$C_{10}$ alkyl.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

Azole: A 5-membered heterocyclic compound containing a nitrogen atom and at least one other heteroatom (nitrogen, sulfur, or oxygen) as part of the ring. Exemplary azoles include imidazole, pyrazole, 1,2,3-triazole, 1,2,4-triazole, tetrazole, pentazole, oxazole, isoxazole, oxadiazole, furazan, 1,3,4-oxadiazole, thiazole, isothiazole, 1,2,3-thiadiazole, 1,2,4-thiadiazole, 1,2,5-thiadiazole, and 1,3,4-thiadiazole. Unless expressly referred to as an "unsubstituted azole," an azole group can either be unsubstituted or substituted.

CPVT: Catecholaminergic Polymorphic Ventricular Tachycardia

Divalent: As used herein, the term "divalent" means bonded to, or capable of forming covalent bonds with, two other atoms or groups within a molecule.

Effective amount (or dose): An amount sufficient to effect a change, such as a change in activity or function of a ryanodine receptor.

Enantiomeric excess (e.e.): A measurement of purity for chiral substances, which reflects the degree to which a sample contains one enantiomer in greater amounts than the other. A racemic mixture has an e.e. of zero, while a completely pure enantiomer has an e.e. of 100%.

Excipient: A physiologically inert substance that is used as an additive in a pharmaceutical composition. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Examples of excipients include but are not limited to polyvinylpyrrolidone (PVP), tocopheryl polyethylene glycol 1000 succinate (also known as vitamin E TPGS, or TPGS), dipalmitoyl phosphatidyl choline (DPPC), trehalose, sodium bicarbonate, glycine, sodium citrate, and lactose.

Halogen (halo): The term halogen includes fluorine, chlorine, bromine, and iodine. Similarly, the term halo includes fluoro, chloro, bromo, and iodo.

Heteroaliphatic: An aliphatic compound or group having at least one heteroatom, i.e., one or more carbon atoms has been replaced with an atom having at least one lone pair of electrons, typically nitrogen, oxygen, phosphorus, silicon, sulfur, or selenium. Heteroaliphatic compounds or groups may be substituted or unsubstituted, branched or unbranched, cyclic or acyclic, and include "heterocycle," "heterocyclyl," "heterocycloaliphatic," or "heterocyclic" groups. Unless expressly referred to as an "unsubstituted heteroaliphatic," a heteroaliphatic group can either be unsubstituted or substituted.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, sulfur, or selenium. A heteroaryl group can have, for example, 5 to 24 ring atoms and contain 1-5 ring heteroatoms (e.g., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide). Unless expressly referred to as an "unsubstituted heteroaryl," a heteroaryl group can either be unsubstituted or substituted. Examples of heteroaryl groups include, for example, the 5- or 6-membered monocyclic and 5-6 bicyclic ring systems shown below:

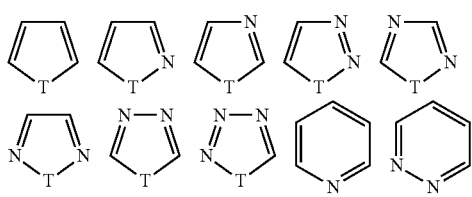

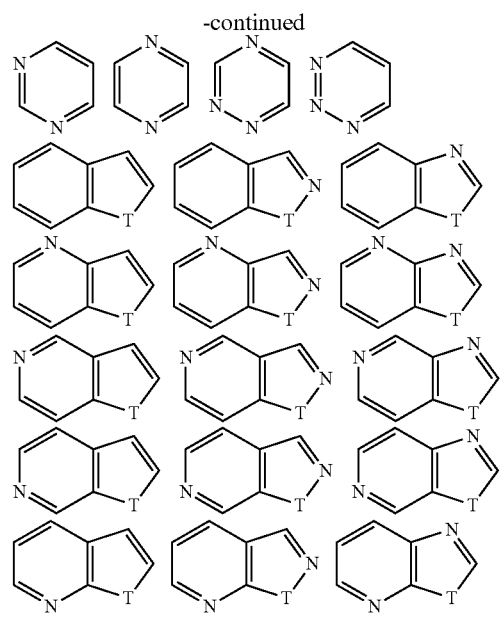

where T is O, S, NH, N-alkyl, N-aryl, N-(arylalkyl) (e.g., N-benzyl), $SiH_2$, SiH(alkyl), Si(alkyl) SiH(arylalkyl), Si(arylalkyl)$_2$, or Si(alkyl)(arylalkyl). Examples of such heteroaryl rings include, but are not limited to, pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinohnvl, benzothienopyridinyl, benzofuropyridinyl groups, and the like.

Hydroxyalkyl: A chemical functional group —ROH where R is an alkyl group.

$IC_{50}$: Half maximal inhibitory concentration, i.e., the concentration of an active agent required to inhibit a biological process by half.

Pharmaceutically acceptable: A substance that can be taken into a subject without significant adverse toxicological effects on the subject. The term "pharmaceutically acceptable form" means any pharmaceutically acceptable derivative or variation, such as stereoisomers, stereoisomer mixtures, enantiomers, solvates, hydrates, isomorphs, polymorphs, pseudomorphs, neutral forms, salt forms, and prodrug agents.

Pharmaceutically acceptable carrier: *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compositions and additional pharmaceutical agents, and is incorporated herein by reference. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected therapeutic dosage of the active agent, for example in a pill, vial, bottle, or syringe.

Pharmaceutically acceptable salt: A biologically compatible salt of a biologically active or therapeutic compound, which salts are derived from a variety of organic and inorganic counter ions and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, benzene sulfonic acid (besylate), cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Prodrug: Prodrugs are compounds that are transformed in vivo to yield a biologically active compound, particularly the parent compound, for example, by hydrolysis in the gut or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R is H or $C_{1-6}$ alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

Solvate: A complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

Stereoisomers: Compounds described herein can contain an asymmetric atom (also referred as a chiral center) and some of the compounds can contain two or more asymmetric atoms or centers, which can thus give rise to stereoisomers. Stereoisomers have the same molecular formula and sequence of bonded atoms, but differ only in the three-dimensional orientation of the atoms in space. Stereoisomers that are not mirror images of one another are termed "diastereomers" and those that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−) isomers respectively). A chiral compound can exist as either individual enantiomer or as a mixture thereof. A mixture containing equal proportions of the enantiomers is called a "racemic mixture." In some embodiments, optical isomers can be obtained in enantiomerically enriched or pure form by standard procedures known to those skilled in the art, which include, for example, chiral separation, diastereomeric salt formation, kinetic resolution, and asymmetric synthesis. E/Z isomers are isomers that differ in the stereochemistry of a double bond. An E isomer (from entgegen, the German word for "opposite") has a trans-configuration at the double bond, in which the two groups of highest priority are on opposite sides of the double bond. A Z isomer (from zusammen, the German word for "together") has a cis-configuration at the double bond, in which the two groups of highest priority are on the same side of the double bond. It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan. It is specifically contemplated that the depiction of one regioisomer includes any other regioisomers and any regioisomeric mixtures unless specifically stated otherwise.

Particular examples of the presently disclosed compounds may include one or more asymmetric centers; thus these compounds can exist in different stereoisomeric forms. Accordingly, compounds and compositions may be provided as individual pure enantiomers or diastereomers, or as stereoisomeric mixtures, including racemic mixtures. In certain embodiments the compounds disclosed herein are synthesized in or are purified to be in substantially enantiopure form, such as in an 85% enantiomeric excess (e.e.), a 90% enantiomeric excess, a 95% enantiomeric excess, a 97% enantiomeric excess, a 98% enantiomeric excess, a 99% enantiomeric excess, or even in greater than a 99% enantiomeric excess, such as in a substantially enantiopure form.

A person of ordinary skill in the art understands that in a compound comprising one or more asymmetric centers, one or both enantiomers or diastereomers are contemplated unless a specific enantiomer or diastereomer is shown or described. For example, a

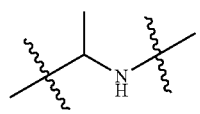

moiety contemplates

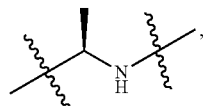 , 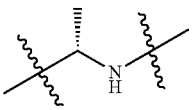

or a mixture thereof, such as a racemic mixture.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloal- kyl, dialkylamino, halo, haloaliphatic (e.g., haloalkyl), haloalkoxy, heteroaliphatic, heteroaryl, heterocycloaliphatic, hydroxyl, oxo, sulfonamide, sulfhydryl, thio, and thioalkoxy groups.

Substituted: A fundamental compound, such as an aryl or aliphatic compound, or moiety, having coupled thereto one or more substituents, each substituent typically replacing a hydrogen atom on the fundamental compound. A person of ordinary skill in the art will recognize that compounds disclosed herein may be described with reference to particular structures and substituents coupled to such structures, and that such structures and/or substituents also can be further substituted, unless expressly stated otherwise or context dictates otherwise. Solely by way of example and without limitation, a substituted aryl compound may have an aliphatic group coupled to the closed ring of the aryl base, such as with toluene. Again solely by way of example and without limitation, a long-chain hydrocarbon may have a halogen or hydroxyl group bonded thereto.

Tautomers: Constitutional isomers of organic compounds that differ only in the position of the protons and electrons, and are interconvertible by migration of a hydrogen atom. Tautomers ordinarily exist together in equilibrium.

Therapeutically effective amount (or dose): An amount sufficient to provide a beneficial, or therapeutic, effect to a subject or a given percentage of subjects.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

II. COMPOUNDS FOR MODIFYING ACTIVITY OF CALCIUM ION CHANNELS

Embodiments of compounds for modifying activity of calcium ion channels, such as ryanodine receptors, are disclosed. Prodrugs, stereoisomers, tautomers, hydrates, solvates, prodrugs, and/or pharmaceutically acceptable salts of the compounds are also encompassed by this disclosure. Some embodiments of the disclosed compounds regulate and/or modulate the activity of calcium release channels such as ryanodine receptors, in cells of a subject (e.g., mammals, such as humans) In particular, because abnormal $Ca^{2+}$ release through RyR2 is now known to be a substantial mechanism of arrhythmogenesis, certain embodiments of the disclosed compounds that target RyR2 also may suppress arrhythmias.

Some embodiments of the disclosed compounds have a chemical structure according to formula I, or a stereoisomer, tautomer, pharmaceutically acceptable salt, hydrate, solvate, or prodrug thereof.

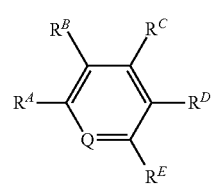

(I)

With respect to formula I, $R^A$ is —N(R$^1$)R$^2$ and $R^B$ is H, aliphatic, —O-aliphatic, —S-aliphatic, —O—C(O)-aliphatic, or halogen, or $R^A$ is N(R$^1$) or —CH$_2$N(R$^1$)— and $R^A$ together with $R^B$ forms a 5- or 6-membered heteroaliphatic or heteroaryl ring; $R^C$ is H, aliphatic, —S-aliphatic, or —O—C(O)-aliphatic, and $R^D$ is substituted aliphatic or —Y—X—(CR$^7_2$)$_m$—N(R$^4$)R$^5$, or $R^C$ and $R^D$ together form a 5- or 6-membered heteroaliphatic or heteroaryl ring, wherein the 5- or 6-membered heteroaliphatic or heteroaryl ring is substituted with —X—(CR$^7_2$)$_m$—N(R$^4$)R$^5$; $R^E$ is H, aliphatic, —O-aliphatic, —S-aliphatic, —O—C(O)-aliphatic, or halogen; Q is N or C—R$^3$; X is absent, N(R$^6$), O, C(O), —S(O$_2$)O—, —OS(O$_2$)—, —P(O)(OH)O—, —OP(O)(OH)$_3$, —N(H)—C(H)(CF$_3$)—, or —C(H)(CF$_3$)—N(H)—; Y is —(CR$^7_2$)$_n$— or a divalent azole ring; R$^1$ and R$^2$ independently are H or aliphatic; R$^3$ is H, aliphatic, —O-aliphatic, or —S-aliphatic; R$^4$ and R$^5$ independently are H, aliphatic, aryl, or heteroaryl, or R$^4$ and R$^5$ together with N form a heterocycloaliphatic or heteroaryl ring; R$^6$ is H or aliphatic; each R$^7$ independently is H, halogen, or aliphatic; and m and n independently are integers from 1 to 10. Unless otherwise specified, the term aliphatic encompasses substituted, unsubstituted, linear, branched, and/or cyclic aliphatic groups. Similarly, unless otherwise specified, the term alkyl hereinafter encompasses substituted, unsubstituted, linear, branched, and/or cyclic alkyl groups. In some embodiments, at least one of the following conditions applies: (i) if Q is C—R$^3$, then at least one of $R^B$, $R^C$, $R^E$, and R$^3$ is other than H, or (ii) if $R^D$ is —Y—X—(CH$_2$)$_m$—N(R$^4$)R$^5$ and X is absent, then Y is not —(CH$_2$)$_n$—, or (iii) the compound includes —Y—N(R$^6$)—(CR$^7_2$)$_m$—N(R$^4$)R$^5$ or —N(R$^6$)—(CR$^7_2$)$_m$—N(R$^4$)R$^5$, or (iv) if Y is a divalent azole ring, then X is absent, or (v) if R$^4$ and R$^5$ together with N form a heterocycloaliphatic or heteroaryl ring and Q is C—R$^3$, then at least of one of $R^B$, $R^C$, $R^E$, and R$^3$ is other than H, or at least one of R$^1$ and R$^2$ is other than H or —CH$_3$; and wherein the compound is not:

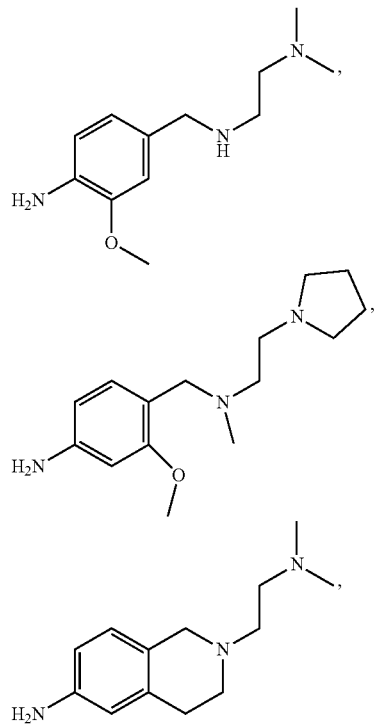

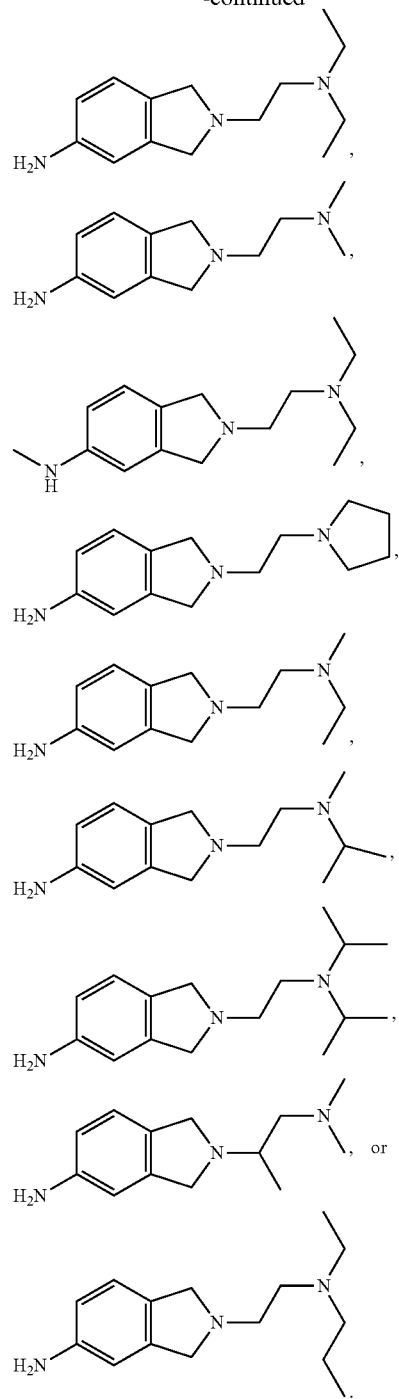

$R^A$ is —N(R$^1$)R$^2$ and $R^B$ is H, aliphatic, —O-aliphatic, —S-aliphatic, —O—C(O)-aliphatic, or halogen, or $R^A$ is N(R$^1$) or —CH$_2$N(R$^1$)— and $R^A$ together with $R^B$ forms a 5- or 6-membered heteroaliphatic or heteroaryl ring. In some embodiments, $R^A$ is N(R$^1$) or —CH$_2$N(R$^1$)— where R$^1$ is H or aliphatic and $R^A$ and $R^B$ together form a 5- or 6-membered heteroaliphatic or heteroaryl ring. In other embodiments, $R^A$ is —N(R$^1$)R$^2$ where R$^1$ and R$^2$ independently are H or aliphatic, and $R^B$ is H, aliphatic, —O-aliphatic (e.g., alkoxy), —S-aliphatic (e.g., alkylsulfanyl), or halogen. In one embodiment, $R^A$ is —N(R$^1$)R$^2$ where R$^1$ is H or alkyl and R$^2$ is H or alkyl, and $R^B$ is H, alkyl, —O-alkyl, —S-alkyl, or halogen. $R^1$ and $R^2$ may be the same or different. In an independent embodiment, $R^A$ is —N($R^1$)— or —$CH_2$N($R^1$)— where $R^1$ is H or alkyl and $R^A$ and $R^B$ together form a 5- or 6-membered heteroaliphatic or heteroaryl ring. In any of the foregoing embodiments, the aliphatic group may be alkyl, the —O-aliphatic group or —S-aliphatic group may be —O-alkyl or —S-alkyl. In some embodiments, the alkyl group or alkyl portion of —O-alkyl or —S-alkyl includes 1-40 carbon atoms, such as 1-20 carbon atoms, 1-10 carbon atoms, or 1-5 carbon atoms. The alkyl portion may be straight, branched, or at least a part of the alkyl portion may be cyclic. For instance, the alkyl group might be methyl, ethyl, propyl, isopropyl, cyclopropyl, n-butyl, sec-butyl, or t-butyl. The —O-alkyl group might be methoxy, ethoxy, propoxy, isopropoxy, cyclopropoxy, n-butoxy, sec-butoxy, or t-butoxy. The —S-alkyl group might be methylsulfanyl, ethylsulfanyl, propylsulfanyl, isopropylsulfanyl, cyclopropylsulfanyl, n-butylsulfanyl, sec-butylsulfanyl, or t-butylsulfanyl. In certain embodiments, the alkyl group or alkyl portion of the O-alkyl group or S-alkyl group is —($CH_2$)—$CF_3$ where n is as previously defined.

In any or all of the above embodiments, $R^C$ is H, aliphatic, —S-aliphatic or —O—C(O)-aliphatic, and $R^D$ is substituted aliphatic or —Y—X—($CR^7_2$)$_m$—N($R^4$)$R^5$, or $R^C$ and $R^D$ together form a 5- or 6-membered heteroaliphatic or heteroaryl ring, wherein the 5- or 6-membered heteroaliphatic or heteroaryl ring is substituted with —X—($CR^7_2$)$_m$—N($R^4$)$R^5$. The 5- or 6-membered heteroaliphatic or heteroaryl ring may be a nitrogen-containing heteroaliphatic or heteroaryl ring. In some embodiments, $R^C$ is H, aliphatic, —S-aliphatic, or —O—C(O)-aliphatic, and $R^D$ is substituted aliphatic or —Y—X—($CR^7_2$)$_m$—N($R^4$)$R^5$. In certain examples, $R^7$ is H. In some embodiments, $R^C$ is H, alkyl, —S-alkyl, or —O—C(O)-alkyl, wherein the alkyl portion is straight, branched, or at least a part of the alkyl portion is cyclic. In some embodiments, the alkyl portion is a $C_1$-$C_{10}$ alkyl, such as a $C_1$-$C_5$ alkyl, e.g., methyl, ethyl, propyl, isopropyl, cyclopropyl, n-butyl, sec-butyl, or t-butyl. In one embodiment, $R^D$ is substituted aliphatic, such as substituted alkyl. $R^D$ may be, for example, aminoalkyl (—($CH_2$)$_q$$NH_2$), hydroxyalkyl (—($CH_2$)$_q$OH), or —($CH_2$)$_q$$SO_3$M where q is an integer from 1 to 10 (i.e., 1, 2, 3, 4, 5, 6, 7, 8, 9, or 10) and M is a monatomic cation (e.g., a group IA metal cation or an ammonium cation); the alkyl portion may be straight, branched, or at least a part of the alkyl portion may be cyclic. In some embodiments, q is 1, 2, 3, 4, or 5; in certain embodiments, q is 1, 2, or 3. In an independent embodiment, $R^D$ is —Y—X—($CR^7_2$)$_m$—N($R^4$)$R^5$ where m is an integer from 1 to 10, i.e., m is 1, 2, 3, 4, 5, 6, 7, 8, 9, or 10. Y is —($CR^7_2$)$_n$— where n is an integer from 1 to 10 (i.e., n is 1, 2, 3, 4, 5, 6, 7, 8, 9, or 10), or a divalent azole ring. In some embodiments, m is 1, 2, 3, 4, or 5, such as 1, 2, or 3; in some embodiments, n is 1, 2, 3, 4, or 5, such as 1, 2, or 3. In certain embodiments, Y is —($CR^7_2$)$_n$— where n is 1, 2, 3, 4, or 5. In any of the foregoing embodiments, each $R^7$ may be H. In particular examples, n is 1. Alternatively, Y may be a divalent azole ring. For instance, Y may be an imidazolyl, pyrazolyl, triazolyl (e.g., 1,2,3- or 1,2,4-triazolyl), tetrazolyl, oxazolyl, isoxazolyl, oxadiazolyl, furazanyl, thiazolyl, isothiazolyl, or thiadiazolyl (e.g., 1,2,3-, 1,2,4-, 1,2,5-, or 1,3,4-thiadiazolyl) group. A carbon atom in the azole ring may be unsubstituted or substituted, e.g., substituted with halogen or alkyl, such as $C_{1-10}$ alkyl, $C_1$-$C_5$ alkyl, or $C_1$-$C_3$ alkyl. Exemplary Y groups include, but are not limited to:

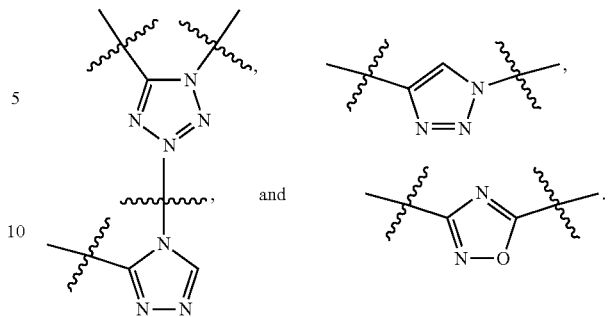

In certain embodiments, $R^C$ and $R^D$ together form a 5- or 6-membered heteroaliphatic or heteroaryl ring. The 5- or 6-membered heteroaliphatic or heteroaryl ring may be a nitrogen-containing heteroaliphatic or heteroaryl ring. In some examples, the ring is a pyrrole, pyrazole, or isoxazole ring. The ring is substituted with —X—($CR^7_2$)$_m$—N($R^4$)($R^5$), where m, X, $R^4$, $R^5$, and $R^7$ are as previously defined. In one embodiment, X is absent. In another embodiment, X is N($R^6$), such as N(H). In some examples, $R^7$ is H.

In any or all of the above embodiments, $R^E$ is H, aliphatic, —O-aliphatic, —S-aliphatic, —O—C(O)-aliphatic, or halogen. In some embodiments, $R^E$ is H, alkyl, —O-alkyl, —S-alkyl, —O—C(O)-alkyl, or halogen. The alkyl group or alkyl portion of —O-alkyl, —S-alkyl, or —O—C(O)-alkyl may include 1-40 carbon atoms, such as 1-20 carbon atoms, 1-10 carbon atoms, or 1-5 carbon atoms. The alkyl portion may be straight, branched, or at least a part of the alkyl portion may be cyclic. For instance, the alkyl group might be methyl, ethyl, propyl, isopropyl, cyclopropyl, n-butyl, sec-butyl, or t-butyl. The —O-alkyl group might be methoxy, ethoxy, propoxy, isopropoxy, cyclopropoxy, n-butoxy, sec-butoxy, or t-butoxy. The —S-alkyl group might be methylsulfanyl, ethylsulfanyl, propylsulfanyl, isopropylsulfanyl, cyclopropylsulfanyl, n-butylsulfanyl, sec-butylsulfanyl, or t-butylsulfanyl. In certain embodiments, the alkyl group or alkyl portion of the O-alkyl group or S-alkyl group is —($CH_2$)—$CF_3$ where n is as previously defined.

In any or all of the above embodiments, Q is N or C—$R^3$ where $R^3$ is H, aliphatic, —O-aliphatic, or —S-aliphatic. In some embodiments, $R^3$ is H, alkyl, —O-alkyl, or —S-alkyl. The alkyl group or alkyl portion of —O-alkyl or —S-alkyl may include 1-40 carbon atoms, such as 1-20 carbon atoms, 1-10 carbon atoms, or 1-5 carbon atoms. The alkyl portion may be straight, branched, or at least a part of the alkyl portion may be cyclic. For instance, the alkyl group might be methyl, ethyl, propyl, isopropyl, cyclopropyl, n-butyl, sec-butyl, or t-butyl. The —O-alkyl group might be methoxy, ethoxy, propoxy, isopropoxy, cyclopropoxy, n-butoxy, sec-butoxy, or t-butoxy. The —S-alkyl group might be methylsulfanyl, ethylsulfanyl, propylsulfanyl, isopropylsulfanyl, cyclopropylsulfanyl, n-butylsulfanyl, sec-butylsulfanyl, or t-butylsulfanyl. In certain embodiments, the alkyl group or alkyl portion of the O-alkyl group or S-alkyl group is —($CH_2$)—$CF_3$ where n is as previously defined. In one embodiment, Q is N. In an independent embodiment, Q is C—$R^3$, where $R^3$ is as described above. In one embodiment, $R^3$ and $R^E$ are the same. In an independent embodiment, $R^3$ and $R^E$ are different.

In any or all of the above embodiments, $R^4$ and $R^5$ independently are H, aliphatic, aryl, or heteroaryl, or $R^4$ and $R^5$ together with N form a heterocycloaliphatic or heteroaryl ring. In some embodiments, $R^4$ and $R^5$ independently are H, alkyl, aryl, or heteroaryl. The alkyl group may be straight, branched, or at least a portion of the alkyl group may be cyclic. The alkyl group may include 1-40 carbon atoms, such as 1-20 carbon atoms, 1-10 carbon atoms, or 1-5 carbon atoms. For instance, the alkyl group might be methyl, ethyl, propyl, isopropyl, cyclopropyl, n-butyl, sec-butyl, or t-butyl. In one embodiment, $R^4$ and $R^5$ are the same. In an independent embodiment, $R^4$ and $R^5$ are different. In one embodiment, $R^4$ and $R^5$ are H. In an independent embodiment, $R^4$ is H and $R^5$ is alkyl. In another independent embodiment, $R^4$ and $R^5$ are alkyl. In yet another independent embodiment, $R^4$ is H and $R^5$ is aryl. In still another independent embodiment, $R^4$ is alkyl and $R^5$ is aryl. In another independent embodiment, $R^4$ and $R^5$ independently are aryl or heteroaryl. In some embodiments, $R^4$ and $R^5$ together with N form a heterocycloaliphatic ring, such as a 5-membered or 6-membered heterocycloaliphatic or heteroaryl ring, for example:

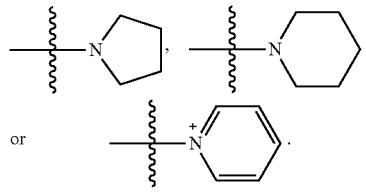

The heterocycloaliphatic or heteroaryl ring may be substituted or unsubstituted. For example, the ring may be substituted with one or more halogens and/or alkyl groups, e.g., one or more $C_1$-$C_{10}$, $C_1$-$C_5$, or $C_1$-$C_3$ groups.

In any or all of the above embodiments, X is absent, $N(R^6)$ 0, C(O), —S(O$_2$)O—, —OS(O$_2$)—, —P(O)(OH)O—, —OP(O)(OH)$_3$, —N(H)—C(H)(CF$_3$)—, or —C(H)(CF$_3$)—N(H)—, where $R^6$ is H or aliphatic. In some embodiments, $R^6$ is H, unsubstituted alkyl, or haloalkyl, such as fluoroalkyl. The alkyl group may include 1-10 carbon atoms, such as 1-5 or 1-3 carbon atoms, and may be straight or branched, or at least a portion of the alkyl group may be cyclic. In some embodiments, if X is absent, then Y is not —(CH$_2$)$_n$—. In certain embodiments, X is N(H), O, C(O), —S(O$_2$)O—, —OS(O$_2$)—, —P(O)(OH)O—, —OP(O)(OH)$_3$, —N(H)—C(H)(CF$_3$)— or —C(H)(CF$_3$)—N(H)—. In one embodiment, X is N(H), O, C(O), —S(O$_2$)O—, or —P(O)(OH)O—. In an independent embodiment, X is N(H), O, or —S(O$_2$)O—. In another independent embodiment, X is N(H).

In any or all of the above embodiments, the variable "m" is an integer. In some embodiments, m is an integer from 1 to 10 (i.e., 1, 2, 3, 4, 5, 6, 7, 8, 9, or 10) or an integer from 1 to 5 (i.e., 1, 2, 3, 4, or 5). In particular examples, m is 2.

In any or all of the above embodiments, the variable "n" is an integer. In some embodiments, n is an integer from 1 to 10 (i.e., 1, 2, 3, 4, 5, 6, 7, 8, 9, or 10) or an integer from 1 to 5 (i.e., 1, 2, 3, 4, or 5). In particular examples, n is 1.

In some embodiments, the compound has a structure according to one of formulas II-VII:

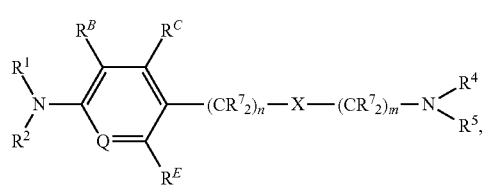

(II)

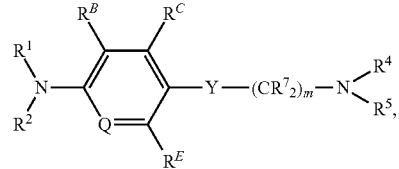

(III)

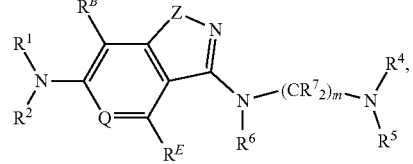

(IV)

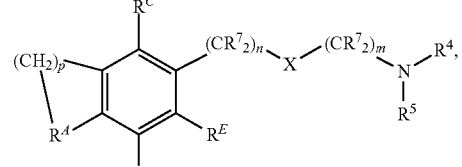

(V)

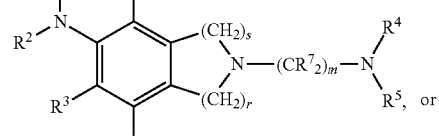

(VI)

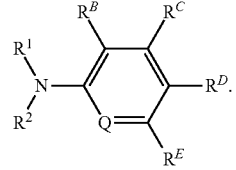

(VII)

With respect to formulas II-VII, $R^1$-$R^6$, $R^E$, M, Q, m, n, and q are as previously described; each $R^7$ independently is H, aliphatic, or halogen; $R^A$ is $N(R^1)$ or —CH$_2$N(R$^1$)—; $R^B$ is H, aliphatic, —O-aliphatic, —S-aliphatic, or halogen; $R^C$ is H or aliphatic; $R^D$ is —(CH$_2$)$_q$NH$_2$, —(CH$_2$)$_q$OH, or —(CH$_2$)$_q$SO$_3$M where q is an integer from 1 to 10 and M is a monatomic cation; X is $N(R^6)$, O, C(O), —S(O$_2$)O—, —OS(O$_2$)—, —P(O)(OH)O—, —OP(O)(OH)$_3$, —N(H)—C(H)(CF$_3$)—, or —C(H)(CF$_3$)—N(H)—; Y is an azole ring; Z is O, N(H), or CH$_2$; $R^A$ is $N(R^1)$ or —CH$_2$N(R$^1$)—; p is 1, 2, or 3 when $R^A$ is $N(R^1)$, or p is 1 or 2 when $R^A$ is —CH$_2$N(R$^1$)—; and r is 1 or 2, s is 1 or 2, and r+s=2 or 3. In some embodiments, $R^6$ is H. In some embodiments, each $R^7$ is H or halogen. In certain embodiments, each $R^7$ is H. In certain examples, q is 1 and M$^+$ is a group IA cation such as Na$^{2+}$. In some embodiments, the compound has a structure according to formula II, formula V, formula VI, or formula VII where $R^D$ is —(CH$_2$)$_q$SO$_3$M.

In any or all of the above embodiments, $R^1$ and $R^2$ independently are H or aliphatic. In some embodiments, $R^1$ is H or alkyl and $R^2$ is H or alkyl. In some examples at least one of $R^1$ and $R^2$ is alkyl. In certain embodiments, $R^1$ and $R^2$ independently are alkyl. In some embodiments, the alkyl group includes 1-40 carbon atoms, such as 1-20 carbon atoms, 1-10 carbon atoms, or 1-5 carbon atoms. The alkyl group may be straight, branched, or at least a part of the alkyl group may be cyclic. For instance, the alkyl group might be methyl, ethyl, propyl, isopropyl, cyclopropyl, n-butyl, sec-butyl, or t-butyl.

In any or all of the above embodiments, $R^4$ and $R^5$ independently may be H, alkyl, such as $C_{1-10}$ or $C_1$-$C_5$ alkyl, aryl, or heteroaryl, or $R^4$ and $R^5$ together with N may form a heterocycloaliphatic or heteroaryl ring, such as a 5- or 6-membered heterocycloaliphatic or heteroaryl ring for example:

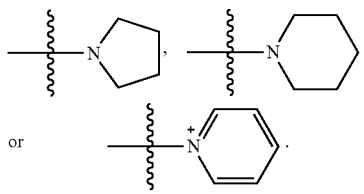

The heterocycloaliphatic or heteroaryl ring may be substituted or unsubstituted. For example, the ring may be substituted with one or more halogens and/or alkyl groups, e.g., one or more $C_1$-$C_{10}$, $C_1$-$C_5$, or $C_1$-$C_3$ groups. The alkyl group may be straight, branched, or at least a part of the alkyl group may be cyclic. For instance, the alkyl group might be methyl, ethyl, propyl, isopropyl, cyclopropyl, n-butyl, sec-butyl, or t-butyl. In one embodiment, $R^4$ and $R^5$ are H. In an independent embodiment, $R^4$ is H and $R^5$ is alkyl. In another independent embodiment, $R^4$ and $R^5$ are alkyl. In yet another independent embodiment, $R^4$ is H and $R^5$ is aryl or heteroaryl. In still another independent embodiment, $R^4$ is alkyl and $R^5$ is aryl or heteroaryl. In another independent embodiment, $R^4$ and $R^5$ independently are aryl or heteroaryl. In yet another independent embodiment, $R^4$ and $R^5$ together with N form a heterocycloaliphatic or heteroaryl ring.

In any or all of the above embodiments, $R^B$ may be H, alkyl, —O-alkyl, —S-alkyl, or halogen. In some embodiments, $R^B$ is H, alkyl, —O-alkyl, or halogen. In any or all of the above embodiments, $R^C$ may be H, alkyl, or S-alkyl. The alkyl group or alkyl portion of —O-alkyl or S-alkyl may include 1-40 carbon atoms, such as 1-20 carbon atoms, 1-10 carbon atoms, or 1-5 carbon atoms. The alkyl portion may be straight, branched, or at least a part of the alkyl portion may be cyclic. For instance, the alkyl group might be methyl, ethyl, propyl, isopropyl, cyclopropyl, n-butyl, sec-butyl, or t-butyl. The —O-alkyl group might be methoxy, ethoxy, propoxy, isopropoxy, cyclopropoxy, n-butoxy, sec-butoxy, or t-butoxy. The —S-alkyl group might be methylsulfanyl, ethylsulfanyl, propylsulfanyl, isopropylsulfanyl, cyclopropylsulfanyl, n-butylsulfanyl, sec-butylsulfanyl, or t-butylsulfanyl.

The variable "m" is an integer. In some embodiments, m is an integer from 1 to 10 (i.e., 1, 2, 3, 4, 5, 6, 7, 8, 9, or 10) or an integer from 1 to 5 (i.e., 1, 2, 3, 4, or 5). In particular examples, m is 2.

The variable "n" is an integer. In some embodiments, n is an integer from 1 to 10 (i.e., 1, 2, 3, 4, 5, 6, 7, 8, 9, or 10) or an integer from 1 to 5 (i.e., 1, 2, 3, 4, or 5). In particular examples, n is 1. In certain examples, when n is 1, Y is —CH$_2$—, —CHF—, or —CF$_2$—.

The variable "q" is an integer. In some embodiments, q is an integer from 1 to 10 (i.e., 1, 2, 3, 4, 5, 6, 7, 8, 9, or 10) or an integer from 1 to 5 (i.e., 1, 2, 3, 4, or 5). In particular examples, q is 1.

In some embodiments, the compound has a structure according to formula II, where Q is CH, N, or C—OCH$_3$, $R^1$ and $R^2$ independently are H or $C_1$-$C_5$ alkyl, X is N($R^6$) or O, n is 1, m is 2, and $R^4$ and $R^5$ independently are $C_1$-$C_5$ alkyl, or $R^4$ and $R^5$ together with N form a 5-membered heterocycloaliphatic ring. In certain embodiments, Q is CH, $R^1$ and $R^2$ are H, X is N($R^6$), n is 1, m is 2, and $R^4$ and $R^5$ independently are $C_1$-$C_5$ alkyl, or $R^4$ and $R^5$ together with N form a 5-membered heterocycloaliphatic ring. In any of the foregoing embodiments, $R^6$ may be H. In some embodiments, if the compound has a structure according to formula II, then at least one of $R^1$ and $R^2$ is other than H, or at least one of $R^C$ and $R^E$ is other than H, or X is other than N(H), or m is not 2, or n is not 1, or if Q is CH then $R^B$ is not —O-aliphatic, or if $R^B$ is H then Q is not C—$R^3$ where $R^3$ is —O-aliphatic.

In formula III, Y is an azole ring. In some embodiments, Y is an imidazolyl, pyrazolyl, triazolyl (e.g., 1,2,3- or 1,2,4-triazolyl), tetrazolyl, oxazolyl, isoxazolyl, oxadiazolyl, furazanyl, thiazolyl, isothiazolyl, or thiadiazolyl (e.g., 1,2,3-, 1,2,4-, 1,2,5-, or 1,3,4-thiadiazolyl) group. Each carbon in the ring, if present, may be unsubstituted or substituted, e.g., substituted with halogen or alkyl, such as $C_1$-$C_5$ alkyl. Exemplary Y groups include, but are not limited to:

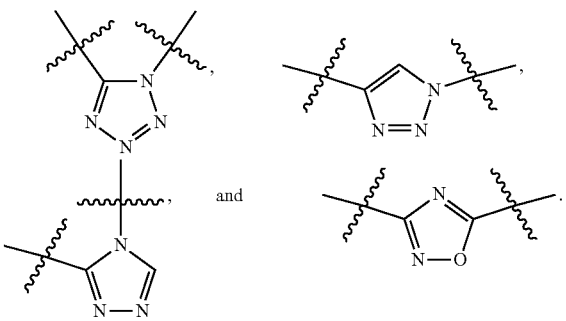

Z is O, N(H), or CH$_2$. In some embodiments, Z is O or N(H).

In some embodiments, a compound according to formula III has a structure according to formula IIIA, IIIB, IIIC, or IIID:

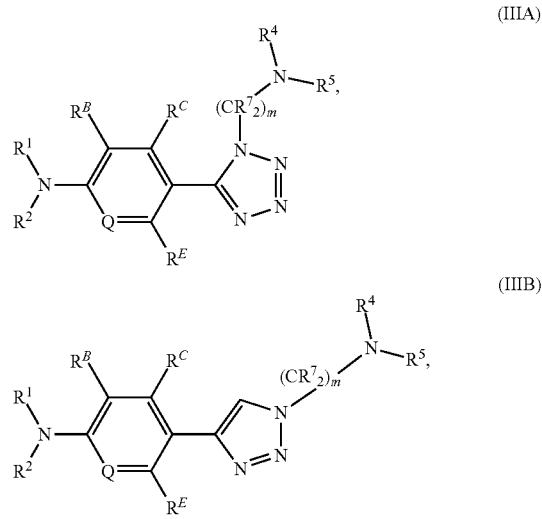

-continued (IIIC)
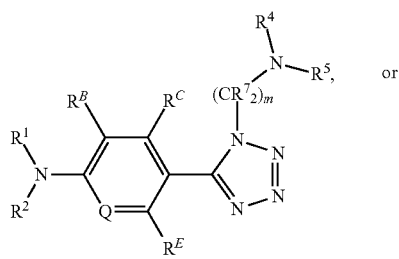

(IIID)
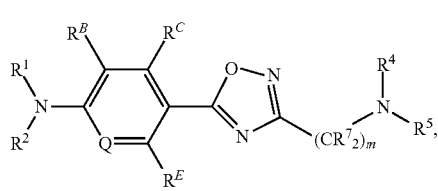

wherein $R^1$-$R^5$, $R^7$, $R^B$, $R^C$, $R^E$, Q, and m are described as above. In one embodiment, $R^4$ and $R^5$ are H. In an independent embodiment, $R^4$ is H and $R^5$ is alkyl. In another independent embodiment, $R^4$ and $R^5$ are alkyl. In yet another independent embodiment, $R^4$ is H and $R^5$ is aryl. In still another independent embodiment, $R^4$ is alkyl and $R^5$ is aryl. In another independent embodiment, $R^4$ and $R^5$ are aryl. In certain of the foregoing embodiments, (i) $R^C$ is H, (ii) Q is C—$R^3$ where $R^3$ is H or $C_1$-$C_5$ alkyl, (iii) m is 2, (iv) $R^B$ is H, (v) $R^E$ is H or $C_1$-$C_5$ alkoxy (e.g., methoxy), or any combination of (i), (ii), (iii), (iv), and (v). In some examples, (i) IV and $R^2$ are both H or are both the same $C_1$-$C_5$ alkyl, (ii) $R^4$ and $R^5$ are both the same $C_1$-$C_5$ alkyl, or both (i) and (ii). In some examples, (i) one of $R^1$ and $R^2$ is H and the other of $R^1$ and $R^2$ is $C_1$-$C_5$ alkyl, (ii) $R^4$ and $R^5$ are both the same $C_1$-$C_5$ alkyl, or both (i) and (ii). In any of the foregoing embodiments, each $R^7$ may be H. In some embodiments, if the compound has a structure according to formula IIIA, then at least one of $R^1$ and $R^2$ is other than H, or at least one of $R^B$, $R^C$, and $R^E$ is other than H, or Q is other than CH.

In some embodiments, the compound has a structure according to formula IV where (i) $R^1$ and $R^2$ independently are H or $C_1$-$C_5$ alkyl, (ii) Q is CH, (iii) $R^B$ and $R^E$ are H, (iv) Z is N(H), (v) m is 2, (vi) $R^4$ and $R^5$ independently are $C_1$-$C_5$ alkyl, or any combination of (i), (ii), (iii), (iv), (v), and (vi). In some examples, (i) $R^1$ and $R^2$ are both H or are both the same $C_1$-$C_5$ alkyl, (ii) $R^4$ and $R^5$ are both the same $C_1$-$C_5$ alkyl, or both (i) and (ii). In any of the foregoing embodiments, each $R^7$ may be H.

In some embodiments, a compound according to formula V has a structure according to formula VA, VB, or VC:

(VA)
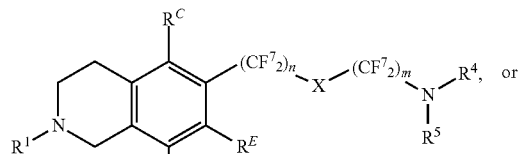

(VB)
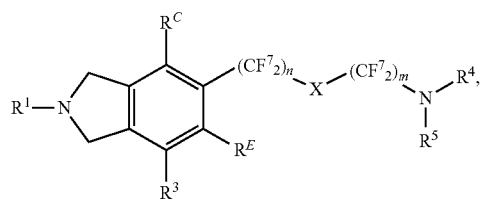

(VC)
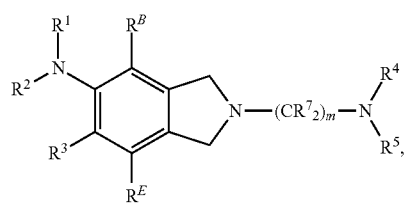

wherein IV, $R^3$-$R^5$, $R^7$, $R^C$, $R^E$, X, m, and n are as previously described. In certain embodiments, each $R^7$ is H. In some embodiments, $R^1$ is H or alkyl. In one embodiment, $R^1$ is alkyl, such as $C_1$-$C_{10}$ or $C_1$-$C_5$ alkyl. In one embodiment, $R^4$ and $R^5$ are H. In an independent embodiment, $R^4$ is H and $R^5$ is alkyl. In another independent embodiment, $R^4$ and $R^5$ are alkyl. In yet another independent embodiment, $R^4$ is H and $R^5$ is aryl. In still another independent embodiment, $R^4$ is alkyl and $R^5$ is aryl. In another independent embodiment, $R^4$ and $R^5$ are aryl. In still another independent embodiment, $R^1$ is H or alkyl, and (i) $R^4$ and $R^5$ are H or (ii) $R^4$ is H and $R^5$ is alkyl. When $R^4$ and/or $R^5$ is alkyl, the alkyl may be $C_1$-$C_{10}$ or $C_1$-$C_5$ alkyl. In any of the foregoing embodiments, the alkyl group may be straight, branched, or at least a part of the alkyl group may be cyclic. For instance, the alkyl group might be methyl, ethyl, propyl, isopropyl, cyclopropyl, n-butyl, sec-butyl, or t-butyl. In any of the foregoing embodiments, (i) $R^C$ may be H, (ii) X may be O or N(H), (iii) or both (i) and (ii). In some embodiments, $R^1$ is $C_1$-$C_5$ alkyl. In some of the foregoing embodiments, m is 2, or n is 1, or m is 2 and n is 1. In some embodiments, R' is $C_1$-$C_5$ alkyl, $R^4$ and $R^5$ independently are $C_1$-$C_5$ alkyl, $R^C$ is H, $R^E$ is H, $R^3$ is H, X is N(H), m is 2, and n is 1. In certain examples, $R^4$ and $R^5$ are the same $C_1$-$C_5$ alkyl. In any of the foregoing embodiments, each $R^7$ may be H.

In some embodiments, a compound according to formula VI has a structure according to formula VIA, VIB, or VIC:

VIA
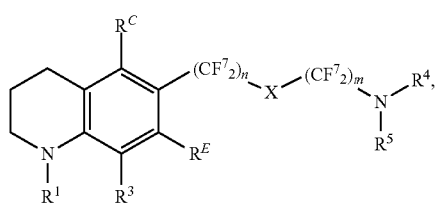

VIB
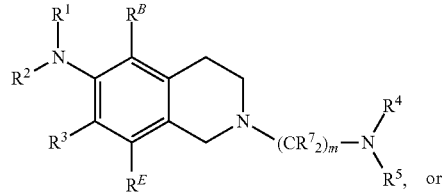

-continued

VIC

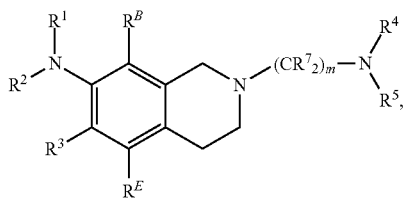

wherein $R^1$-$R^5$, $R^B$, $R^E$, and m are as previously defined. In certain embodiments, m is 2. In some embodiments, R' is H or alkyl and $R^2$ is H or alkyl. In some examples at least one of $R^1$ and $R^2$ is alkyl. In certain embodiments, $R^1$ and $R^2$ independently are alkyl. In some embodiments, the alkyl group includes 1-40 carbon atoms, such as 1-20 carbon atoms, 1-10 carbon atoms, or 1-5 carbon atoms. In some examples, $R^4$ and $R^5$ together with N form a heterocycloaliphatic ring. In some embodiments, $R^B$, $R^E$, and $R^3$ are H, one or $R^1$ and $R^2$ is H and the other of $R^1$ and $R^2$ is H or $C_1$-$C_5$ alkyl, m is 2, and $R^4$ and $R^5$ independently are $C_1$-$C_5$ alkyl or $R^4$ and $R^5$ together with N form a 5-membered heterocycloaliphatic ring. In certain examples, $R^4$ and $R^5$ are the same $C_1$-$C_5$ alkyl or $R^4$ and $R^5$ together with N form a 5-membered heterocycloaliphatic ring. In any of the foregoing embodiments, the alkyl group may be straight, branched, or at least a part of the alkyl group may be cyclic. For instance, the alkyl group might be methyl, ethyl, propyl, isopropyl, cyclopropyl, n-butyl, sec-butyl, or t-butyl. In any of the foregoing embodiments, each $R^7$ may be H. In some embodiments, if the compound has a structure according formula VIA, then at least one of $R^B$, $R^E$, or $R^3$ is other than H, or m is not 2, or if one of $R^1$ and $R^2$ is H, then the other of $R^1$ and $R^2$ is other than H or $CH_3$. In some embodiments, if the compound has a structure according to formula VIB, then at least one of $R^B$, $R^E$, or $R^3$ is other than H, or m is not 2, or at least one of $R^1$ and $R^2$ is other than H, or at least one of $R^4$ and $R^5$ is other than $-CH_3$.

In some embodiments, the compound has a structure according to formula VII where $R^D$ is $-(CH_2)_q SO_3 M$ where q and M are as previously defined. In certain embodiments, q is 1, M is Na, $R^1$ and $R^2$ independently are H or $C_1$-$C_5$ alkyl, $R^E$ is H or $C_1$-$C_5$ alkoxy (e.g., methoxy), and Q is C—$R^3$ where $R^3$ is $C_1$-$C_5$ alkoxy (e.g., methoxy) or H. In some examples, $R^1$ and $R^2$ are the same. In any of the foregoing embodiments, the alkyl group or alkyl portion of the alkoxy group may be straight, branched, or at least a part of the alkyl group or portion may be cyclic.

Some embodiments of the disclosed compounds have a formula:

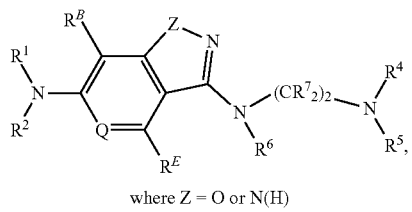

where Z = O or N(H)

-continued

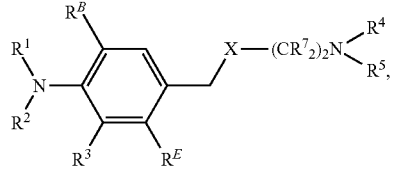

where X = O, N($R^6$), C(O), $SO_3$, or $PO_2OH$

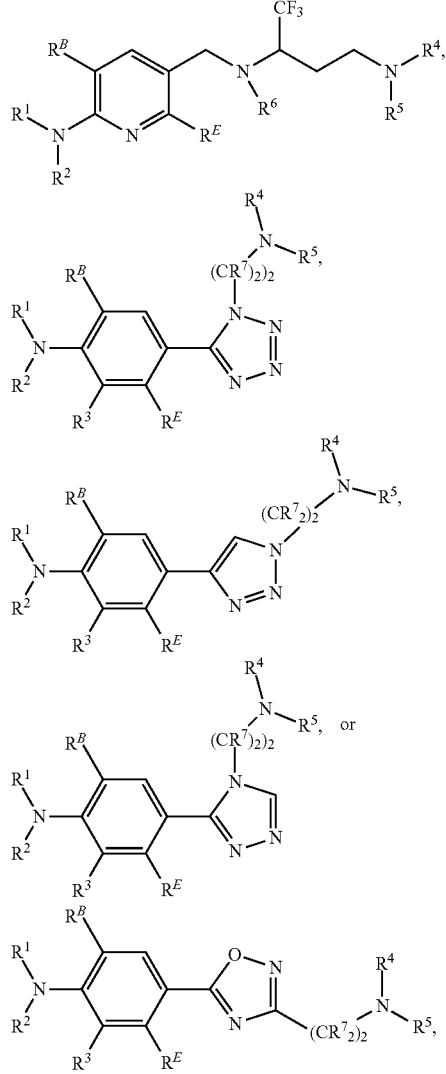

where $R^6$ and $R^7$ are as previously defined, optionally where $R^6$ and $R^7$ are H, and $R^1$-$R^5$, $R^B$, and $R^E$ are as follows:

|    | $R^1$ | $R^2$ | $R^3$ | $R^4$ | $R^5$ | $R^B$   | $R^E$   |
|----|-------|-------|-------|-------|-------|---------|---------|
| 1  | H     | H     | H     | alkyl | alkyl | H       | H       |
| 2  | H     | H     | H     | alkyl | alkyl | alkyl   | H       |
| 3  | H     | H     | H     | alkyl | alkyl | O-alkyl | H       |
| 4  | H     | H     | H     | alkyl | alkyl | halogen | H       |
| 5  | H     | alkyl | H     | alkyl | alkyl | H       | H       |
| 6  | H     | alkyl | H     | alkyl | alkyl | H       | alkyl   |
| 7  | H     | alkyl | H     | alkyl | alkyl | alkyl   | alkyl   |
| 8  | H     | alkyl | H     | alkyl | alkyl | O-alkyl | alkyl   |
| 9  | H     | alkyl | H     | alkyl | alkyl | halogen | alkyl   |
| 10 | alkyl | alkyl | H     | alkyl | alkyl | H       | H       |
| 11 | alkyl | alkyl | H     | alkyl | alkyl | H       | alkyl   |
| 12 | alkyl | alkyl | H     | alkyl | alkyl | alkyl   | alkyl   |

|    | R¹    | R²    | R³      | R⁴    | R⁵    | Rᴮ      | Rᴱ      |
|----|-------|-------|---------|-------|-------|---------|---------|
| 13 | alkyl | alkyl | H       | alkyl | alkyl | O-alkyl | alkyl   |
| 14 | alkyl | alkyl | H       | alkyl | alkyl | halogen | alkyl   |
| 15 | H     | H     | alkyl   | alkyl | alkyl | H       | H       |
| 16 | H     | H     | alkyl   | alkyl | alkyl | alkyl   | H       |
| 17 | H     | H     | alkyl   | alkyl | alkyl | O-alkyl | H       |
| 18 | H     | H     | alkyl   | alkyl | alkyl | halogen | H       |
| 19 | H     | alkyl | alkyl   | alkyl | alkyl | H       | H       |
| 20 | H     | alkyl | alkyl   | alkyl | alkyl | alkyl   | H       |
| 21 | H     | alkyl | alkyl   | alkyl | alkyl | O-alkyl | H       |
| 22 | H     | alkyl | alkyl   | alkyl | alkyl | halogen | H       |
| 23 | alkyl | alkyl | alkyl   | alkyl | alkyl | H       | H       |
| 24 | alkyl | alkyl | alkyl   | alkyl | alkyl | alkyl   | H       |
| 25 | alkyl | alkyl | alkyl   | alkyl | alkyl | O-alkyl | H       |
| 26 | alkyl | alkyl | alkyl   | alkyl | alkyl | halogen | H       |
| 27 | H     | H     | H       | alkyl | alkyl | H       | O-alkyl |
| 28 | H     | H     | H       | alkyl | alkyl | alkyl   | O-alkyl |
| 29 | H     | H     | H       | alkyl | alkyl | O-alkyl | O-alkyl |
| 30 | H     | H     | H       | alkyl | alkyl | halogen | O-alkyl |
| 31 | H     | alkyl | H       | alkyl | alkyl | H       | O-alkyl |
| 32 | H     | alkyl | H       | alkyl | alkyl | alkyl   | O-alkyl |
| 33 | H     | alky  | H       | alkyl | alkyl | O-alkyl | O-alkyl |
| 34 | H     | alkyl | H       | alkyl | alkyl | halogen | O-alkyl |
| 35 | alkyl | alkyl | H       | alkyl | alkyl | H       | O-alkyl |
| 36 | alkyl | alkyl | H       | alkyl | alkyl | alkyl   | O-alkyl |
| 37 | alkyl | alkyl | H       | alkyl | alkyl | O-alkyl | O-alkyl |
| 38 | alkyl | alkyl | H       | alkyl | alkyl | halogen | O-alkyl |
| 39 | H     | H     | O-alkyl | alkyl | alkyl | H       | H       |
| 40 | H     | H     | O-alkyl | alkyl | alkyl | alkyl   | H       |
| 41 | H     | H     | O-alkyl | alkyl | alkyl | O-alkyl | H       |
| 42 | H     | H     | O-alkyl | alkyl | alkyl | halogen | H       |
| 43 | H     | alkyl | O-alkyl | alkyl | alkyl | H       | H       |
| 44 | H     | alkyl | O-alkyl | alkyl | alkyl | H       | alkyl   |
| 45 | H     | alkyl | O-alkyl | alkyl | alkyl | alkyl   | alkyl   |
| 46 | H     | alkyl | O-alkyl | alkyl | alkyl | O-alkyl | alkyl   |
| 47 | H     | alkyl | O-alkyl | alkyl | alkyl | halogen | alkyl   |
| 48 | alkyl | alkyl | O-alkyl | alkyl | alkyl | H       | H       |
| 49 | alkyl | alkyl | O-alkyl | alkyl | alkyl | H       | alkyl   |
| 50 | alkyl | alkyl | O-alkyl | alkyl | alkyl | alkyl   | alkyl   |
| 51 | alkyl | alkyl | O-alkyl | alkyl | alkyl | O-alkyl | alkyl   |
| 52 | alkyl | alkyl | O-alkyl | alkyl | alkyl | halogen | alkyl   |
| 53 | H     | H     | O-alkyl | alkyl | alkyl | H       | H       |
| 54 | H     | H     | O-alkyl | alkyl | alkyl | alkyl   | H       |
| 55 | H     | H     | O-alkyl | alkyl | alkyl | O-alkyl | H       |
| 56 | H     | H     | O-alkyl | alkyl | alkyl | halogen | H       |
| 57 | H     | alkyl | O-alkyl | alkyl | alkyl | H       | H       |
| 58 | H     | alkyl | O-alkyl | alkyl | alkyl | alkyl   | H       |
| 59 | H     | alkyl | O-alkyl | alkyl | alkyl | O-alkyl | H       |
| 60 | H     | alkyl | O-alkyl | alkyl | alkyl | halogen | H       |
| 61 | alkyl | alkyl | O-alkyl | alkyl | alkyl | H       | H       |
| 62 | alkyl | alkyl | O-alkyl | alkyl | alkyl | alkyl   | H       |
| 63 | alkyl | alkyl | O-alkyl | alkyl | alkyl | O-alkyl | H       |
| 64 | alkyl | alkyl | O-alkyl | alkyl | alkyl | halogen | H       |
| 65 | H     | H     | O-alkyl | alkyl | alkyl | H       | O-alkyl |
| 66 | H     | H     | O-alkyl | alkyl | alkyl | alkyl   | O-alkyl |
| 67 | H     | H     | O-alkyl | alkyl | alkyl | O-alkyl | O-alkyl |
| 68 | H     | H     | O-alkyl | alkyl | alkyl | halogen | O-alkyl |
| 69 | H     | alkyl | O-alkyl | alkyl | alkyl | H       | O-alkyl |
| 70 | H     | alkyl | O-alkyl | alkyl | alkyl | alkyl   | O-alkyl |
| 71 | H     | alkyl | O-alkyl | alkyl | alkyl | O-alkyl | O-alkyl |
| 72 | H     | alkyl | O-alkyl | alkyl | alkyl | halogen | O-alkyl |
| 73 | alkyl | alkyl | O-alkyl | alkyl | alkyl | H       | O-alkyl |
| 74 | alkyl | alkyl | O-alkyl | alkyl | alkyl | alkyl   | O-alkyl |
| 75 | alkyl | alkyl | O-alkyl | alkyl | alkyl | O-alkyl | O-alkyl |
| 76 | alkyl | alkyl | O-alkyl | alkyl | alkyl | halogen | O-alkyl |
| 77 | H     | H     | H       | alkyl | alkyl | H       | S-alkyl |
| 78 | H     | H     | H       | alkyl | alkyl | alkyl   | S-alkyl |
| 79 | H     | H     | H       | alkyl | alkyl | O-alkyl | S-alkyl |
| 80 | H     | H     | H       | alkyl | alkyl | halogen | S-alkyl |
| 81 | H     | H     | H       | alkyl | alkyl | S-alkyl | H       |
| 82 | H     | H     | H       | alkyl | alkyl | S-alkyl | alkyl   |
| 83 | H     | H     | H       | alkyl | alkyl | S-alkyl | o-alkyl |
| 84 | H     | H     | H       | alkyl | alkyl | S-alkyl | halogen |
| 85 | H     | H     | S-alkyl | alkyl | alkyl | H       | H       |
| 86 | H     | H     | S-alkyl | alkyl | alkyl | alkyl   | H       |
| 87 | H     | H     | S-alkyl | alkyl | alkyl | O-alkyl | H       |
| 88 | H     | H     | S-alkyl | alkyl | alkyl | halogen | H       |
| 89 | H     | H     | S-alkyl | alkyl | alkyl | H       | alkyl   |
| 90  | H     | H     | S-alkyl | alkyl | alkyl | H       | O-alkyl |
| 91  | H     | H     | S-alkyl | alkyl | alkyl | H       | halogen |
| 92  | H     | alkyl | H       | alkyl | alkyl | H       | S-alkyl |
| 93  | H     | alkyl | H       | alkyl | alkyl | alkyl   | S-alkyl |
| 94  | H     | alkyl | H       | alkyl | alkyl | O-alkyl | S-alkyl |
| 95  | H     | alkyl | H       | alkyl | alkyl | halogen | S-alkyl |
| 96  | H     | alkyl | H       | alkyl | alkyl | S-alkyl | H       |
| 97  | H     | alkyl | H       | alkyl | alkyl | S-alkyl | alkyl   |
| 98  | H     | alkyl | H       | alkyl | alkyl | S-alkyl | O-alkyl |
| 99  | H     | alkyl | H       | alkyl | alkyl | S-alkyl | halogen |
| 100 | H     | alkyl | S-alkyl | alkyl | alkyl | H       | H       |
| 101 | H     | alkyl | S-alkyl | alkyl | alkyl | alkyl   | H       |
| 102 | H     | alkyl | S-alkyl | alkyl | alkyl | O-alkyl | H       |
| 103 | H     | alkyl | S-alkyl | alkyl | alkyl | halogen | H       |
| 104 | H     | alkyl | S-alkyl | alkyl | alkyl | H       | alkyl   |
| 105 | H     | alkyl | S-alkyl | alkyl | alkyl | H       | O-alkyl |
| 106 | H     | alkyl | S-alkyl | alkyl | alkyl | H       | halogen |
| 107 | alkyl | alkyl | H       | alkyl | alkyl | H       | S-alkyl |
| 108 | alkyl | alkyl | H       | alkyl | alkyl | alkyl   | S-alkyl |
| 109 | alkyl | alkyl | H       | alkyl | alkyl | O-alkyl | S-alkyl |
| 110 | alkyl | alkyl | H       | alkyl | alkyl | halogen | S-alkyl |
| 111 | alkyl | alkyl | H       | alkyl | alkyl | S-alkyl | H       |
| 112 | alkyl | alkyl | H       | alkyl | alkyl | S-alkyl | alkyl   |
| 113 | alkyl | alkyl | H       | alkyl | alkyl | S-alkyl | O-alkyl |
| 114 | alkyl | alkyl | H       | alkyl | alkyl | S-alkyl | halogen |
| 115 | alkyl | alkyl | S-alkyl | alkyl | alkyl | H       | H       |
| 116 | alkyl | alkyl | S-alkyl | alkyl | alkyl | alkyl   | H       |
| 117 | alkyl | alkyl | S-alkyl | alkyl | alkyl | O-alkyl | H       |
| 118 | alkyl | alkyl | S-alkyl | alkyl | alkyl | halogen | H       |
| 119 | alkyl | alkyl | S-alkyl | alkyl | alkyl | H       | alkyl   |
| 120 | alkyl | alkyl | S-alkyl | alkyl | alkyl | H       | O-alkyl |
| 121 | alkyl | alkyl | S-alkyl | alkyl | alkyl | H       | halogen |

In each of the above embodiments, each alkyl group or alkyl portion of an O-alkyl group or S-alkyl group independently may include 1-40 carbon atoms, such as 1-20 carbon atoms, 1-10 carbon atoms, or 1-5 carbon atoms. The alkyl portion may be straight or branched or at least a part of the alkyl portion may be cyclic. In certain embodiments, the alkyl group or alkyl portion of the O-alkyl group or S-alkyl group is —(CH$_2$)$_n$CF$_3$ where n is as previously defined.

Certain embodiments of the disclosed compounds have a formula:

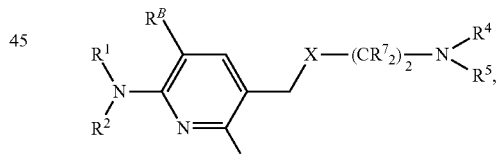

where X=O, N(R⁶) where R⁶ is H or aliphatic (e.g., unsubstituted alkyl or haloalkyl, such as fluoroalkyl), or SO₃; each R⁷ is as previously defined, optionally wherein R⁷ is H, and R¹, R², R⁴, R⁵, Rᴮ, and Rᴱ are as follows:

|     | R¹    | R²    | R⁴    | R⁵    | Rᴮ    | Rᴱ    |
|-----|-------|-------|-------|-------|-------|-------|
| 122 | H     | H     | alkyl | alkyl | H     | H     |
| 123 | H     | H     | H     | alkyl | H     | H     |
| 124 | H     | H     | H     | alkyl | H     | H     |
| 125 | H     | alkyl | alkyl | alkyl | alkyl | H     |
| 126 | H     | alkyl | alkyl | H     | alkyl | H     |
| 127 | H     | alkyl | H     | alkyl | alkyl | H     |
| 128 | alkyl | alkyl | alkyl | alkyl | alkyl | H     |
| 129 | alkyl | alkyl | alkyl | H     | alkyl | H     |
| 130 | alkyl | alkyl | H     | alkyl | alkyl | H     |

-continued

| | R¹ | R² | R⁴ | R⁵ | R$^B$ | R$^E$ |
|---|---|---|---|---|---|---|
| 131 | H | H | alkyl | alkyl | H | alkyl |
| 132 | H | H | alkyl | H | H | alkyl |
| 133 | H | H | H | alkyl | H | alkyl |
| 134 | H | alkyl | alkyl | alkyl | H | alkyl |
| 135 | H | alkyl | alkyl | H | H | alkyl |
| 136 | H | alkyl | H | alkyl | H | alkyl |
| 137 | alkyl | alkyl | alkyl | alkyl | H | alkyl |
| 138 | alkyl | alkyl | alkyl | H | H | alkyl |
| 139 | alkyl | alkyl | H | alkyl | H | alkyl |
| 140 | H | H | alkyl | alkyl | O-alkyl | H |
| 141 | H | H | alkyl | H | O-alkyl | H |
| 142 | H | H | H | alkyl | O-alkyl | H |
| 143 | H | alkyl | alkyl | alkyl | O-alkyl | H |
| 144 | H | alkyl | alkyl | H | O-alkyl | H |
| 145 | H | alkyl | H | alkyl | O-alkyl | H |
| 146 | alkyl | alkyl | alkyl | alkyl | O-alkyl | H |
| 147 | alkyl | alkyl | alkyl | H | O-alkyl | H |
| 148 | alkyl | alkyl | H | alkyl | O-alkyl | H |
| 149 | H | H | alkyl | alkyl | H | O-alkyl |
| 150 | H | H | alkyl | H | H | O-alkyl |
| 151 | H | H | H | alkyl | H | O-alkyl |
| 152 | H | alkyl | alkyl | alkyl | alkyl | O-alkyl |
| 53 | H | alkyl | alkyl | alkyl | H | alkyl | O-alkyl |
| 54 | H | alkyl | H | alkyl | alkyl | O-alkyl |
| 155 | alkyl | alkyl | alkyl | alkyl | alkyl | O-alkyl |
| 156 | alkyl | alkyl | alkyl | H | alkyl | O-alkyl |
| 157 | alkyl | alkyl | H | alkyl | alkyl | O-alkyl |
| 158 | H | alkyl | alkyl | alkyl | H | O-alkyl |
| 159 | H | alkyl | alkyl | H | H | O-alkyl |
| 160 | H | alkyl | H | alkyl | H | O-alkyl |
| 161 | alkyl | alkyl | alkyl | alkyl | H | O-alkyl |
| 162 | alkyl | alkyl | alkyl | H | H | O-alkyl |
| 163 | alkyl | alkyl | H | alkyl | H | O-alkyl |
| 164 | H | H | alkyl | alkyl | O-alkyl | O-alkyl |
| 165 | H | H | alkyl | H | O-alkyl | O-alkyl |
| 166 | H | H | H | alkyl | O-alkyl | O-alkyl |
| 167 | H | alkyl | alkyl | alkyl | O-alkyl | O-alkyl |
| 168 | H | alkyl | alkyl | H | O-alkyl | O-alkyl |
| 169 | H | alkyl | H | alkyl | O-alkyl | O-alkyl |
| 170 | alkyl | alkyl | alkyl | alkyl | O-alkyl | O-alkyl |
| 171 | alkyl | alkyl | alkyl | H | O-alkyl | O-alkyl |
| 172 | alkyl | alkyl | H | alkyl | O-alkyl | O-alkyl |
| 173 | H | H | alkyl | alkyl | H | S-alkyl |
| 174 | H | H | alkyl | H | S-alkyl | H |
| 175 | H | alkyl | alkyl | alkyl | H | S-alkyl |
| 176 | H | alkyl | alkyl | H | S-alkyl | H |
| 177 | alkyl | alkyl | alkyl | alkyl | H | S-alkyl |
| 178 | alkyl | alkyl | alkyl | H | S-alkyl | H |

In each of the above embodiments, each alkyl group or alkyl portion of an O-alkyl or S-alkyl group independently may include 1-40 carbon atoms, such as 1-20 carbon atoms, 1-10 carbon atoms, or 1-5 carbon atoms. The alkyl portion may be straight or branched or at least a part of the alkyl portion may be cyclic. In certain embodiments, the alkyl group or alkyl portion of the O-alkyl group or S-alkyl group is —(CH$_2$)—CF$_3$ where n is as previously defined.

Some embodiments of the disclosed compounds have a formula:

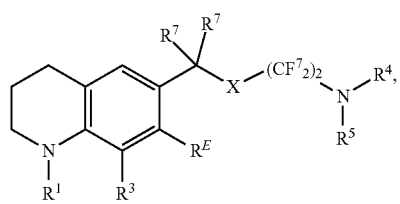

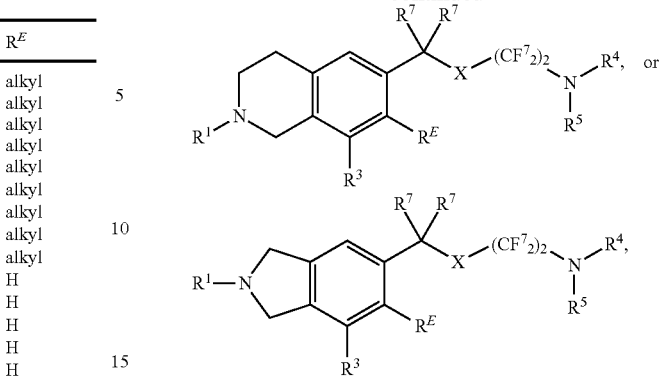

where X is O or N(R$^6$) where R$^6$ is H or aliphatic (e.g., unsubstituted alkyl or haloalkyl, such as fluoroalkyl); each R$^7$ independently is H, alkyl, or fluoro, optionally wherein R$^7$ is H; and R$^1$, R$^3$-R$^5$, and R$^E$ are as follows:

| | R¹ | R³ | R⁴ | R⁵ | R$^E$ |
|---|---|---|---|---|---|
| 179 | H | H | H | H | H |
| 180 | H | H | H | alkyl | H |
| 181 | H | alkyl | H | alkyl | H |
| 182 | H | H | H | alkyl | alkyl |
| 183 | H | alkyl | H | alkyl | alkyl |
| 184 | H | alkyl | H | alkyl | O-alkyl or S-alkyl |
| 185 | H | O-alkyl or S-alkyl | H | alkyl | alkyl |
| 186 | H | H | H | alkyl | halogen |
| 187 | H | halogen | H | alkyl | H |
| 188 | H | alkyl | H | alkyl | halogen |
| 189 | H | halogen | H | alkyl | alkyl |
| 190 | H | O-alkyl or S-alkyl | H | alkyl | H |
| 191 | H | H | H | alkyl | O-alkyl or S-alkyl |
| 192 | H | O-alkyl | H | alkyl | O-alkyl |
| 193 | H | H | alkyl | alkyl | H |
| 194 | H | alkyl | alkyl | alkyl | H |
| 195 | H | H | alkyl | alkyl | alkyl |
| 196 | H | alkyl | alkyl | alkyl | alkyl |
| 197 | H | alkyl | alkyl | alkyl | O-alkyl |
| 198 | H | O-alkyl or S-alkyl | alkyl | alkyl | alkyl |
| 199 | H | H | alkyl | alkyl | halogen |
| 200 | H | halogen | alkyl | alkyl | H |
| 201 | H | alkyl | alkyl | alkyl | halogen |
| 202 | H | halogen | alkyl | alkyl | alkyl |
| 203 | H | O-alkyl or S-alkyl | alkyl | alkyl | H |
| 204 | H | H | alkyl | alkyl | O-alkyl or S-alkyl |
| 205 | H | O-alkyl | alkyl | alkyl | O-alkyl |
| 206 | alkyl | H | alkyl | alkyl | H |
| 207 | alkyl | alkyl | alkyl | alkyl | H |
| 208 | alkyl | H | alkyl | alkyl | alkyl |
| 209 | alkyl | alkyl | alkyl | alkyl | alkyl |
| 210 | alkyl | alkyl | alkyl | alkyl | O-alkyl or S-alkyl |
| 211 | alkyl | O-alkyl or S-alkyl | alkyl | alkyl | alkyl |
| 212 | alkyl | H | alkyl | alkyl | halogen |
| 213 | alkyl | halogen | alkyl | alkyl | H |
| 214 | alkyl | alkyl | alkyl | alkyl | halogen |
| 215 | alkyl | halogen | alkyl | alkyl | alkyl |
| 216 | alkyl | O-alkyl or S-alkyl | alkyl | alkyl | H |
| 217 | alkyl | H | alkyl | alkyl | O-alkyl or S-alkyl |
| 218 | alkyl | O-alkyl | alkyl | alkyl | O-alkyl |

In each of the above embodiments, each alkyl group or alkyl portion of an O-alkyl or S-alkyl group independently may include 1-40 carbon atoms, such as 1-20 carbon atoms, 1-10 carbon atoms, or 1-5 carbon atoms. The alkyl portion may be straight or branched or at least a part of the alkyl portion may be cyclic. In certain embodiments, the alkyl group or alkyl portion of the O-alkyl group or S-alkyl group is —(CH$_2$)—CF$_3$ where n is as previously defined.

Additional nonlimiting examples of compounds according to Formula VII include:

-continued

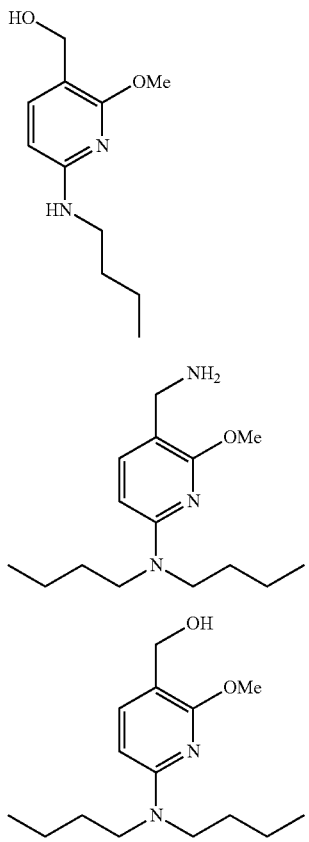

In any or all of the above embodiments, one or more H atoms may be replaced by deuterium atoms.

In some embodiments, the compound is:
$N^1$-(4-amino-2-methoxybenzyl)-$N^2$,$N^2$-diethylethane-1,2-diamine;
3-methoxy-4-(((2-(pyrrolidin-1-yl)ethyl)amino)methyl)aniline;
sodium (4-amino-2-methoxyphenyl)methanesulfonate;
N-butyl-2-(2-(diethylamino)ethyl)isoindolin-5-amine;
N-butyl-2-(2-(pyrrolidin-1-yl)ethyl)isoindolin-5-amine;
sodium (4-(dibutylamino)-3-methoxyphenyl)methanesulfonate;
sodium (4-amino-3-methoxyphenyl)methanesulfonate;
4-((2-(diethylamino)ethoxy)methyl)-2,3-dimethoxyaniline;
N-butyl-4-(3-((diethylamino)methyl)-1,2,4-oxadiazol-5-yl)-3-methoxyaniline;
N-butyl-4-(3-((dimethylamino)methyl)-1,2,4-oxadiazol-5-yl)-3-methoxyaniline;
N-butyl-4-(3-((dibutylamino)methyl)-1,2,4-oxadiazol-5-yl)-3-methoxyaniline;
N-butyl-4-(3-((dibutylamino)methyl)-1,2,4-oxadiazol-5-yl)-2-methylaniline;
N-butyl-5-((2-(diethylamino)ethoxy)methyl)pyridin-2-amine;
$N^1$-((1-butyl-1,2,3,4-tetrahydroquinolin-6-yl)methyl)-$N^2$,$N^2$-dimethylethane-1,2-diamine;
N-butyl-4-(1-(2-(dibutylamino)ethyl)-1H-tetrazol-5-yl)-2-methylaniline;
2-(2-(diethylamino)ethyl)-1,2,3,4-tetrahydroisoquinolin-6-amine;
$N^3$-(2-(diethylamino)ethyl)-1H-indazole-3,6-diamine;
$N^6$,$N^6$-dibutyl-$N^3$-(2-(diethylamino)ethyl)-1H-indazole-3,6-diamine;
$N^1$-((1-butyl-1,2,3,4-tetrahydroquinolin-6-yl)methyl)-$N^2$,$N^2$-diethylethane-1,2-diamine;
$N^1$-(4-amino-3-methylbenzyl)-$N^2$,$N^2$-diethylethane-1,2-diamine;
$N^1$-((6-aminopyridin-3-yl)methyl)-$N^2$,$N^2$-dibutylethane-1,2-diamine;
$N^1$-((6-(butylamino)pyridin-3-yl)methyl)-$N^2$,$N^2$-diethylethane-1,2-diamine;
N-butyl-5-(((2-(pyrrolidin-1-yl)ethyl)amino)methyl)pyridin-2-amine;
N-butyl-2-(2-(diethylamino)ethyl)-1,2,3,4-tetrahydroisoquinolin-6-amine; or
N-butyl-2-(2-(pyrrolidin-1-yl)ethyl)-1,2,3,4-tetrahydroisoquinolin-6-amine.

III. SYNTHESIS OF COMPOUNDS

FIGS. 1-15 show exemplary synthetic schemes useful for preparing embodiments of the disclosed compounds. A person of ordinary skill in the art of organic chemical synthesis will understand that alternative synthesis schemes also may be used to prepare the illustrated compounds as well as additional embodiments of compounds as disclosed herein.

Figure 8:
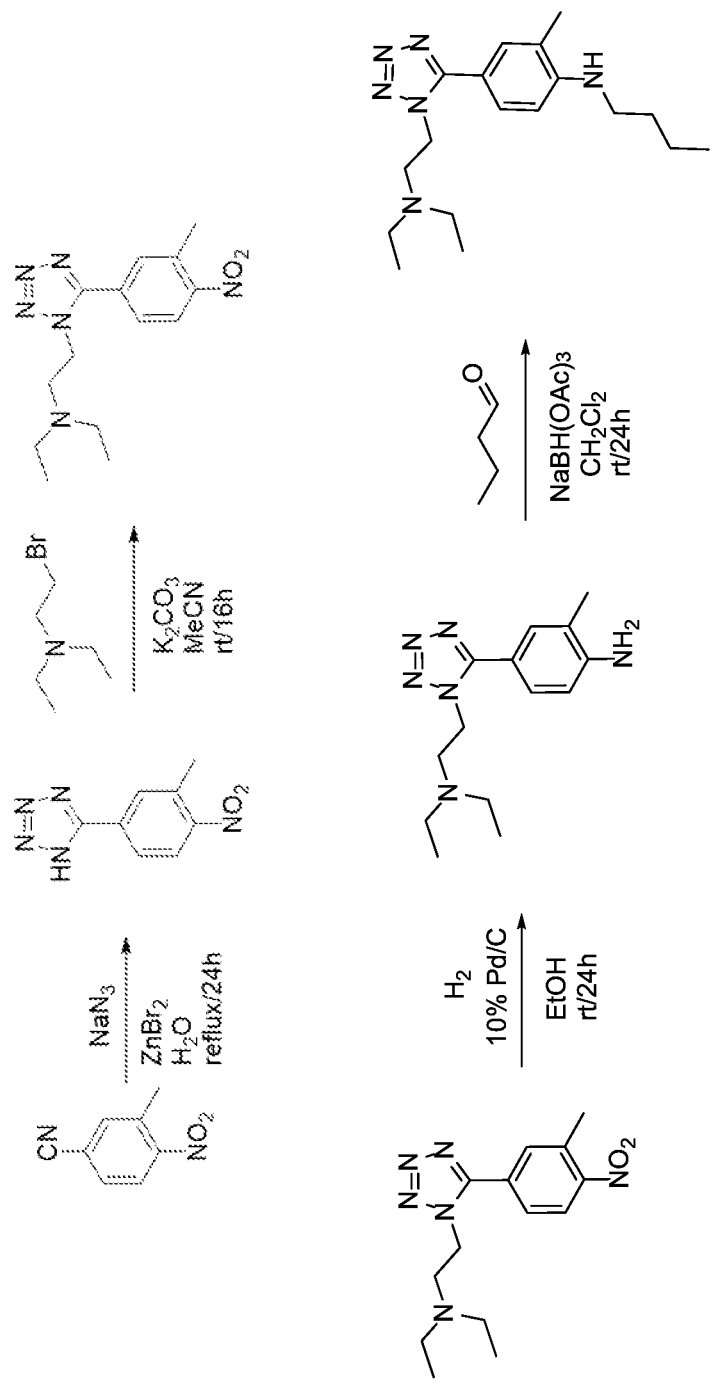
FIG. 8 an exemplary synthetic scheme for preparing compounds according to formula IIIA.
Figure 9:
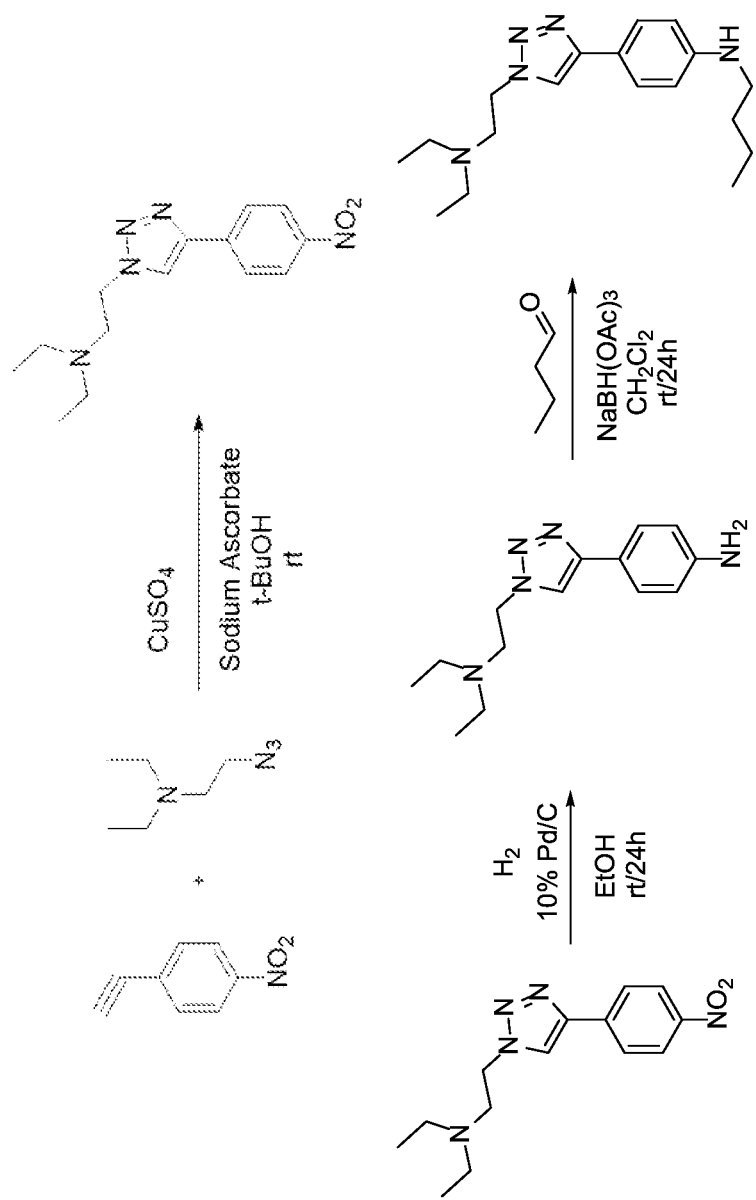
FIG. 9 is an exemplary synthetic scheme for preparing compounds according to formula IIIB.
Figure 10:
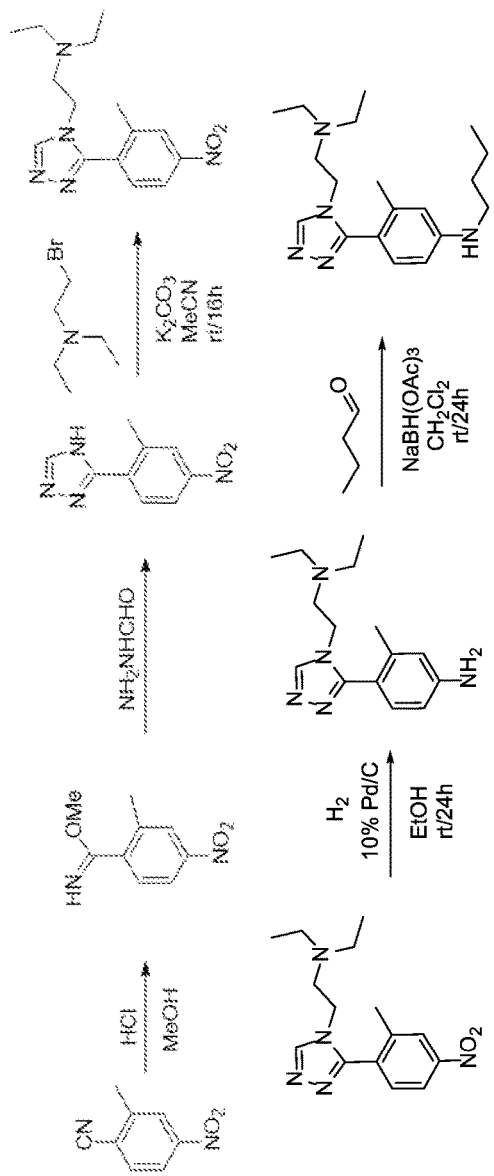
FIG. 10 is an exemplary synthetic scheme for preparing compounds according to formula IIIC.
Figure 11:
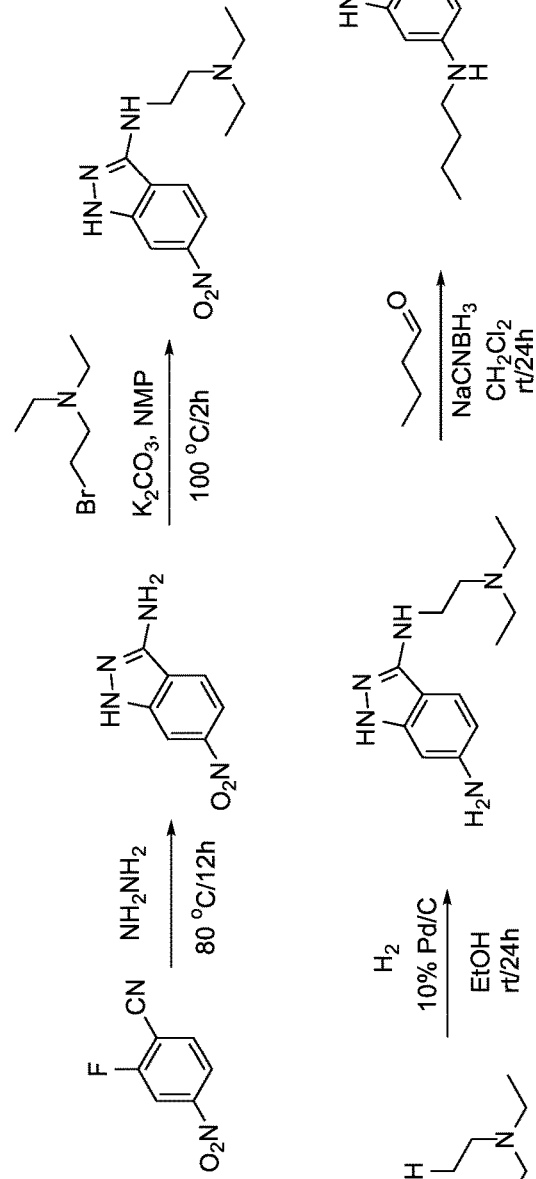
FIG. 11 is an exemplary synthetic scheme for preparing compounds according to formula IV, with the particular synthesis illustrating preparing an exemplary compound according to formula IV where Z is NH.
Figure 12:
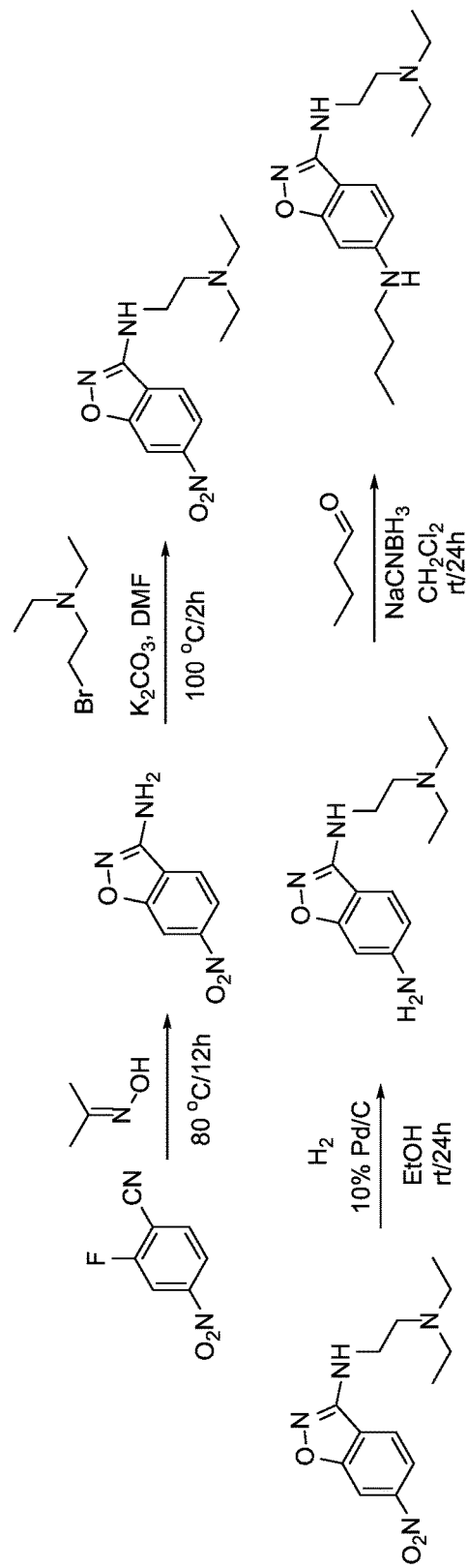
FIG. 12 is an exemplary synthetic scheme for preparing compounds according to formula IV, with the particular synthesis illustrating preparing an exemplary compound according to formula IV where Z is O.
Figure 13:
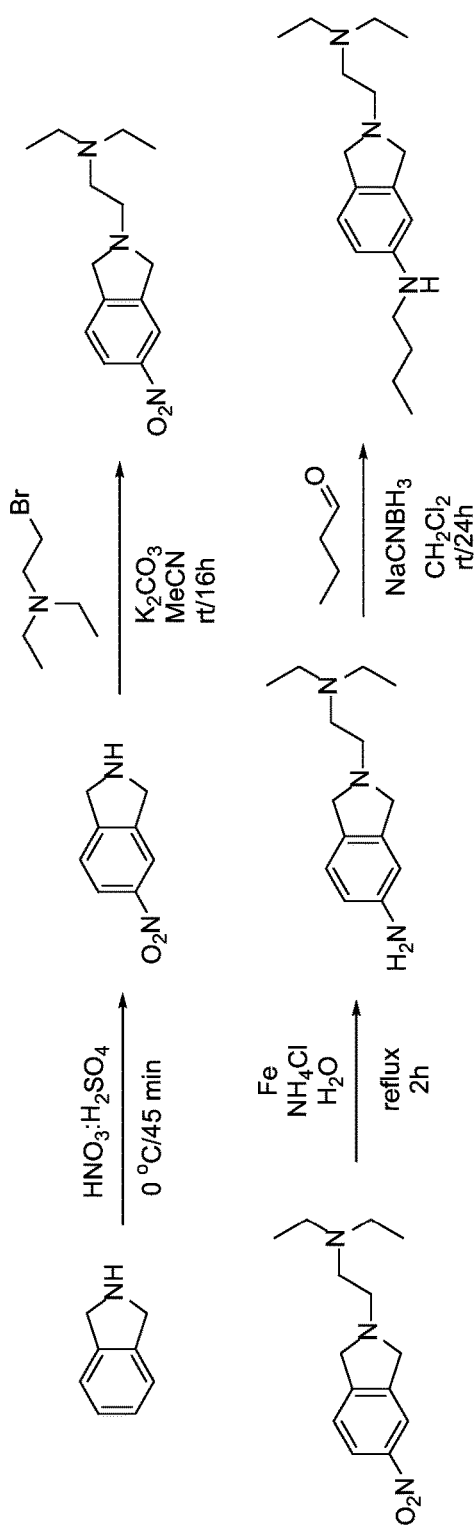
FIG. 13 is an exemplary synthetic scheme for preparing compounds according to formula VI, with the particular synthesis illustrating preparing an exemplary compound according to formula VI where $R^C$ and $R^D$ together form a 5-membered heteroaryl ring.
Figure 14:
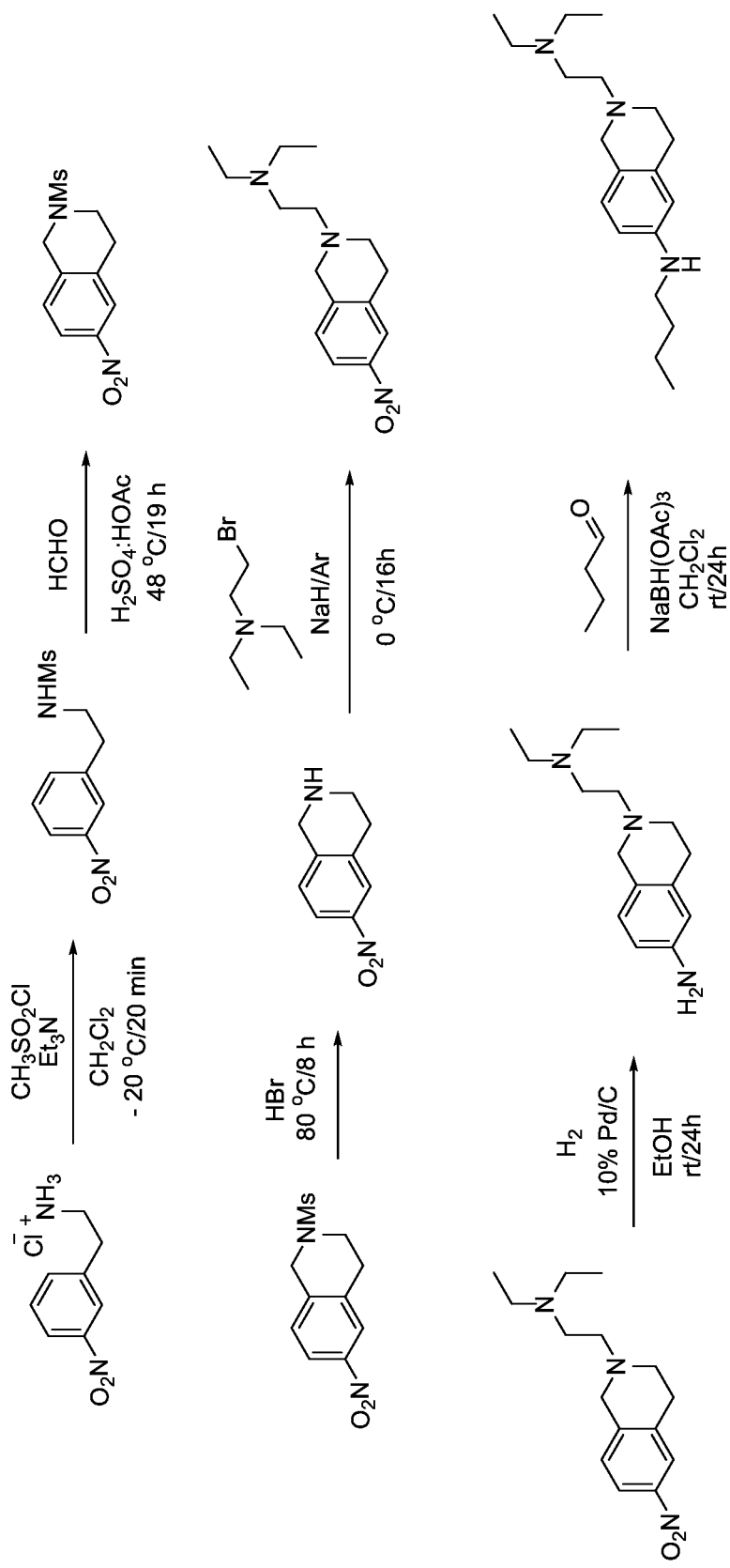
FIG. 14 is an exemplary synthetic scheme for preparing compounds according to formula VI, with the particular synthesis illustrating preparing an exemplary compound according to formula VI where $R^C$ and $R^D$ together form a 6-membered heteroaliphatic ring.
Figure 15:
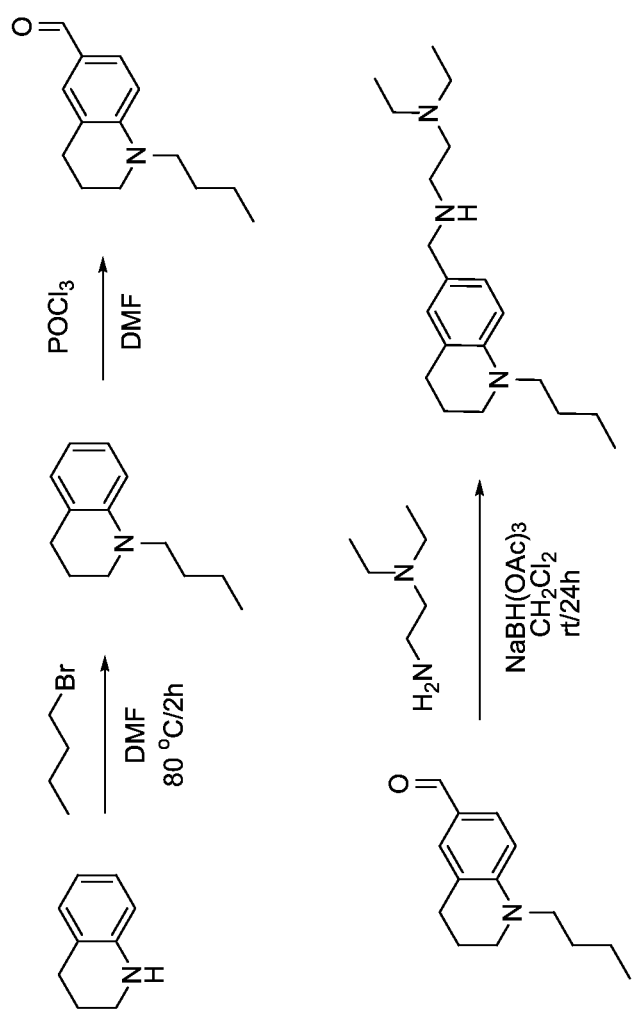
FIG. 15 is an exemplary synthetic scheme for preparing compounds according to formula V, with the particular synthesis illustrating preparing an exemplary compound according to formula V where $R^A$ and $R^B$ together form a 6-membered heteroaliphatic ring.

Certain compounds according to formula II where X is $SO_3$, $PO_2OH$, N(H), O, or —N(H)—C(H)($CF_3$)—, and Q is C(H) or N may be synthesized as shown by FIGS. 1-7. Certain compounds according to formulas IIIA-IIIC may be synthesized as shown by FIGS. 8-10. Certain compounds according to formula IV may be synthesized as shown by FIGS. 11 and 12. Certain compounds according to formula I where $R^C$ and $R^D$ together form a 5- or 6-membered heteroaliphatic or heteroaryl ring and X is absent may be synthesized as shown by FIGS. 13 and 14. An exemplary compound according to formula I where $R^A$ and $R^B$ together form a 6-membered heteroaliphatic ring may be synthesized as shown by FIG. 15.

IV. PHARMACEUTICAL COMPOSITIONS

Embodiments of the disclosed pharmaceutical compositions include a compound according to formula I, or a stereoisomer, tautomer, pharmaceutically acceptable salt, solvate, hydrate, or prodrug thereof, and at least one pharmaceutically acceptable additive such as pharmaceutically acceptable carriers, thickeners, diluents, buffers, preservatives, surface active agents and the like in addition to the molecule of choice. Pharmaceutical compositions can also include one or more additional active ingredients such as anti-arrhythmia agents, anti-hypertension agents, antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), for example, describes compositions and formulations suitable for pharmaceutical delivery of the compounds herein disclosed.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The compounds (hereinafter referred to as "the agents") disclosed herein can be administered to subjects by a variety of routes, including by intramuscular, subcutaneous, intravenous, intra-arterial, intra-articular, intraperitoneal, intracerebroventricular, parenteral, oral, rectal, intranasal, intrapulmonary, transdermal, or topical routes. In other alternative embodiments, the agents can be utilized ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, isotonizing agents (for example, sodium chloride, mannitol, sorbitol), adsorption inhibitors (for example, Tween® 80 polyethylene sorbitol ester or Miglyol® 812 triglycerides), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion from the vehicle, disintegration of the vehicle, or associated formation of water channels in the vehicle. In some circumstances, the agent is dispersed in microcapsules (microspheres) or nanocapsules (nanospheres) prepared from a suitable polymer, for example, cyanoacrylates, such as isobutyl 2-cyanoacrylate (see, for example, Michael et al., *J. Pharmacy Pharmacol.* 43:1-5, 1991, incorporated herein by reference), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, viscosity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be achieved by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, polymers such as poly(epsilon-caprolactone), poly(epsilon-caprolactone-CO-lactic acid), poly(epsilon-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978, incorporated herein by reference). Other useful formulations include controlled-release microcapsules (U.S. Pat. Nos. 4,652,441 and 4,917,893, incorporated herein by reference), lactic acid-glycolic acid copolymers useful in making microcapsules and other formulations (U.S. Pat. Nos. 4,677,191 and 4,728,721, incorporated herein by reference) and sustained-release compositions for water-soluble peptides (U.S. Pat. No. 4,675,189, incorporated herein by reference).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected disease or condition or one or more symptom(s) thereof.

The administration of the agents can be for either prophylactic or therapeutic purpose. When provided prophylactically, the agents are provided in advance of any symptom. The prophylactic administration of the agents serves to prevent or ameliorate any subsequent disease process. When provided therapeutically, the agents are provided at (or shortly after) the onset of an undesirable symptom, e.g., a cardiac arrhythmia.

For prophylactic and therapeutic purposes, the agents can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosages of the agents can be provided as repeated doses within a prolonged prophylaxis or treatment regimen to alleviate one or more symptoms or detectable conditions associated with a targeted condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosages of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of an agent within the methods and formulations of the disclosure is 0.001 mg/kg body weight to 100 mg/kg body weight, such as 0.01 mg/kg body weight to 20 mg/kg body weight, 0.05 mg/kg to 5 mg/kg body weight, or 0.2 mg/kg to 2 mg/kg body weight. Dosage can be varied by the attending clinician to maintain a desired concentration at a target site (for example, systemic circulation). Higher or lower concentrations can be selected based on the mode of delivery, for example, trans-epidermal or oral delivery versus intravenous or subcutaneous delivery. Dosage can also be adjusted based on the release rate of the administered formulation, for example, of sustained release oral versus injected particulate or transdermal delivery formulations, and so forth.

V. METHODS OF USE

Some embodiments of the disclosed compounds are useful for modulating the activity of calcium ion channels and/or for treating cardiac arrhythmias, such as ventricular arrhythmias. In certain embodiments, the disclosed compounds modulate and/or regulate the activity of one or more ryanodine receptors, particularly RyR2. Some embodiments of the disclosed compounds reduce the open probability of a RyR and/or reduce $Ca^{2+}$ release across a RyR (e.g., into the cytoplasm of a cell).

Ventricular arrhythmias that may be treated by embodiments of the disclosed compounds include, but are not limited to, ventricular tachycardia (or VT). VT is a type of tachycardia, or a rapid heartbeat that arises from improper electrical activity of the heart that presents as a rapid heart rhythm. VT is associated with the bottom chambers of the heart, called the ventricles, which are pumping chambers of the heart.

Catecholaminergic Polymorphic Ventricular Tachycardia (or CPVT) is an orphan disease that affects approximately $\frac{1}{10,000}$ humans. The condition is a severe genetic arrhythmogenic disorder characterized by adrenergically induced ventricular tachycardia (VT) that manifests as syncope and sudden death. As one example, a typical age of CPVT onset is between 7 and 9 years of age for both male and female genders. Syncopal spells, brought on by exercise or acute emotion, are frequently the first symptom observed, although sudden death can be the first manifestation of the disease for a subset of patients (10-20%). The three genes linked to CPVT are the cardiac ryanodine receptor (RyR2) gene, which is the cause of CPVT in approximately 55% to 65% of cases, and the cardiac calsequestrin (CASQ2) and triadin genes. Such genetic defects are associated with a disruption of normal $Ca^{2+}$ homeostasis in affected individuals (Pott et al., *Europace*. 13(6): p. 897-901).

In cardiomyocytes, calmodulin (CaM) is mainly bound to the cardiac ryanodine receptor (RyR2) (Wu et al. Cell Calcium 2007; 41:353-364), binding with high affinity (Balshaw et al., J Biol Chem 2001; 276:20144-20153; Guo et al., Biophys J 2011; 101:2170-2177) and stabilizing channel activity (Balshaw et al., Yamaguchi et al., J Biol Chem 2003; 278:23480-23486). Defective CaM-RyR2 interactions have been associated with increased $Ca^{2+}$ sparks (Ono et al., Cardiovasc Res 2010; 87:609-617), cardiac hypertrophy (Lavorato et al., J Muscle Res Cell Motil 2015; 36:205-214; Yamaguchi et al., J Clin Invest 2007; 117:1344-1353), ventricular arrhythmia (Yang et al., Circ Res 2014; 114:295-306), and a reduction in RyR2-bound CaM is often observed in failing hearts (Wu et al., Ono et al., Lavorato et al.). Many of the underlying factors contributing to heart failure are also associated with altered CaM-RyR2 interactions including: oxidative stress (Oda et al., J Mol Cell Cardiol 2015; 85:240-248), PKA phosphorylatrion (Fukuda et al., Biochem Biophys Res Commun 2014; 448:1-7), and CAMKII activity (Uchinoumi et al., J Mol Cell Cardiol 2016; 98:62-72).

CaM is known to play a critical role in several genetic disorders of the heart. Impaired CaM binding and regulation of RyR2 has been associated with the CPVT-linked RyR2 mutation R2474S (Fukuda et al.; Xu et al., Biochem Biophys Res Commun 2010; 394:660-666). Additionally, mutations in the CALM1 gene encoding CaM associated with CPVT have been linked to defective CaM regulation of RyR2 (Nyegaard et al., Am J Hum Genet 2012; 91:703-712; Vassilakopoulou et al., Biochim Biophys Acta BBA—Gen Subj 2015; 1850:2168-2176; Hwang et al., Circ Res 2014; 114:1114-1124). Mutations in the CALM1 and CALM2 genes have also been linked to long QT syndrome (LQTS) (Vassilakopoulou et al.; Crotti et al., Circulation 2013; 127:1009-1017; Limpitikul et al., J Mol Cell Cardiol 2014; 74:115-124; Hwang et al. Circ Res 2014; 114:1114-1124). However, the pathogenesis of LQTS resulting from these mutations in CaM does not appear to be related to regulation of RyR2 (Hwang et al.). Instead, these mutations result in impaired $Ca^{2+}$ binding to CaM (Crotti et al.), which is thought to disrupt interactions with the L-type $Ca^{2+}$ channel (Peterson et al., Neuron 1999; 22:549-558) resulting in a prolonged QT interval.

Certain embodiments of the disclosed compounds exhibit an inhibitory effect on the spark frequency of cells derived from a CPVT mouse model. $IC_{50}$ is a measure of the effectiveness of a substance in inhibiting a particular biological process or function. The quantitative value of $IC_{50}$ can be determined by identifying the concentration where half of the maximum biological response, such as the calcium spark response, is inhibited. In some embodiments, a compound as disclosed herein has a calcium spark response $IC_{50}$ value of from 5 nM to 200,000 nM, such as an $IC_{50}$ value of from 10 nM to 100,000 nM, from 10 nM to 10,000 nM, from 10 nM to 1,000 nM, 10 nM to 500 nM, or from 20 nM to 500 nM.

Figure 16:
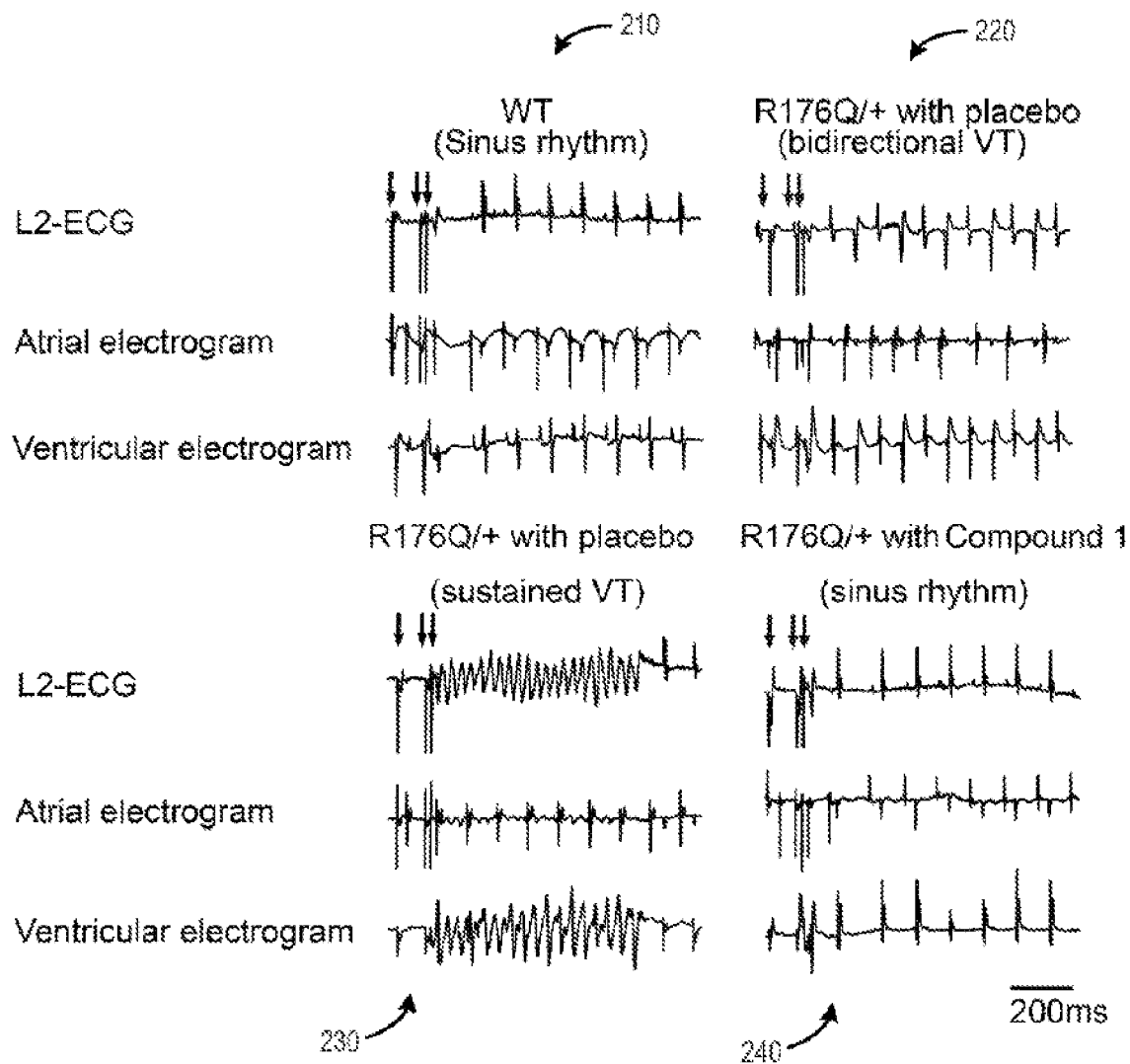
FIG. 16 (prior art) depicts the effects of an anti-arrhythmia drug on arrhythmias in CPVT (Catecholaminergic Polymorphic Ventricular Tachycardia) mice.
Figure 18B:
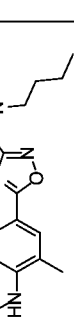
Figure 18B:
Figure 18B:
Figure 18B:
Figure 18B:
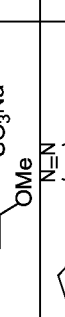
Figure 18B:
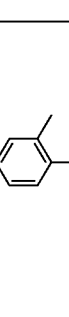
Figure 18C:
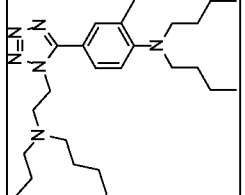
Figure 18C:
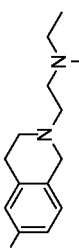
Figure 18C:
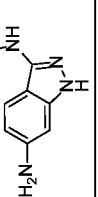
Figure 18C:
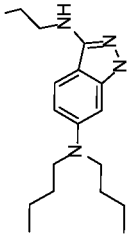
Figure 18E:
Figure 18E:
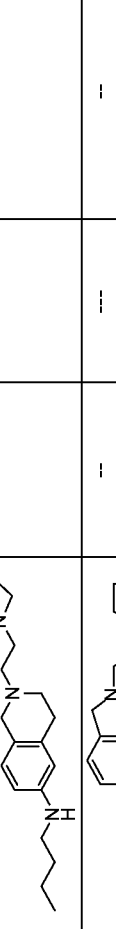
Figure 18E:
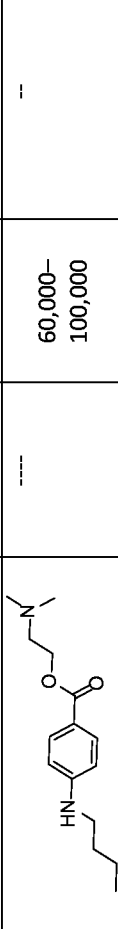
Figure 18E:
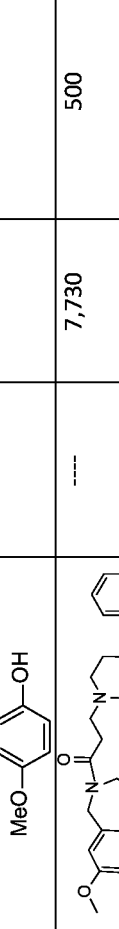
Figure 18E:
Figure 18E:
Figure 18E:

Efficacy also can be measured using electrical activity data (e.g., atrial and/or ventricular intracardiac electrocardiogram or EKG data) to visualize the effect on cardiac arrhythmias. The incidence of bidirectional VT and/or sustained polymorphic VT can be assessed. For instance, placebo-treated R176/+ mice develop bidirectional VT or sustained polymorphic VT following cardiac pacing. In contrast, R176Q/+ mice treated with some embodiments of the disclosed compounds are protected from arrhythmic development following pacing, and exhibit normal sinus rhythm. FIG. 16 shows example electrical activity data to illustrate the effect of a drug for treating cardiac arrhythmias using two different arrhythmogenic models. Therein, electrical signals for four different CPVT mice are shown. Wild type (or WT) signal 210 is provided for reference to illustrate a sinus rhythm (e.g., L2-ECG, lead 2 of the surface ECG). Atrial and ventricular intracardiac electrocardiogram signals are also provided for reference. Placebo-treated R176/+ mice developed bidirectional VT (signal 220) or sustained polymorphic VT (signal 230) following cardiac pacing (arrows). In contrast, R176Q/+ mice treated with a prior-art, anti-arrhythmia compound ("Compound 1") were protected from arrhythmic development following pacing, and exhibited normal sinus rhythm (signal 240). Certain embodiments of the disclosed compounds similarly exhibit anti-arrhythmia effects.

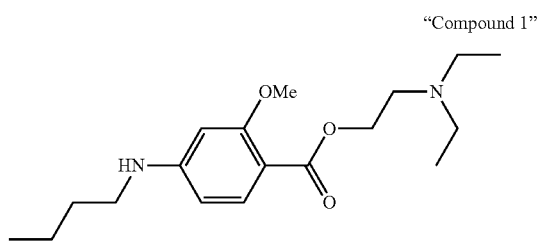

"Compound 1"

In some embodiments, administration of a therapeutically effective dose of a compound to a subject as disclosed herein reduces incidence of arrhythmia by at least 5%, at least 10%, at least 20%, at least 30%, at least 40%, at least 50%, at least 60%, at least 70%, at least 80%, or at least 90% relative to the incidence of arrhythmia in the absence of the compound. The subject may be a mammal. In certain embodiments, the subject is a human. In some embodiments, the therapeutically effective dose is within a range of from 0.1 µg/kg to 100 mg/kg body weight, such as within a range of from 1 µg/kg to 100 mg/kg, from 1 µg/kg to 10 mg/kg, from 1 µg/kg to 1 mg/kg, from 1 µg/kg to 500 µg/kg, or from 2 µg/kg to 250 µg/kg.

In some instances, advantages are realized by delivering the compound in a neutral, or non-salt, form of the compound. Charged ions may not interact as strongly with the ryanodine receptor, which may reduce a drug potency compared to a compound with a non-salt form. For this reason, the compound may be included within a pharmaceutical composition in a non-salt form.

A method for modulating activity of a calcium ion channel includes contacting the calcium ion channel with an effective amount of a compound as disclosed herein or a pharmaceutically acceptable salt thereof. In some embodiments, contacting the calcium ion channel with the compound inhibits activity of the calcium ion channel. The calcium ion channel may be a ryanodine receptor, such as RyR2.

Contacting the calcium ion channel may be performed in vivo. In some embodiments, contacting the calcium ion channel comprises administering the effective amount of the compound, or pharmaceutically acceptable salt, solvate, hydrate, or prodrug thereof, to a subject identified as having, or being at risk of having, a cardiac arrhythmia or heart failure. In certain embodiments, administering the effective amount of the compound, or pharmaceutically acceptable salt, solvate, hydrate, or prodrug thereof, comprises administering an amount of a pharmaceutical composition comprising the effective amount of the compound to the subject.

A method for ameliorating at least one sign or symptom of a cardiac arrhythmia or heart failure may include administering one or more therapeutically effective doses of a compound, or plurality of compounds, as disclosed herein or a pharmaceutically acceptable salt thereof over an effective period of time to a subject identified as having, or being at risk of having, a cardiac arrhythmia or heart failure, thereby ameliorating at least one sign or symptom of the cardiac arrhythmia or heart failure in the subject. In some embodiments, ameliorating at least one sign or symptom of cardiac arrhythmia includes reducing the incidence of cardiac arrhythmia, reducing the severity of the cardiac arrhythmia, and/or shortening the duration of an episode of cardiac arrhythmia. The subject may be a mammal, particularly a human. In some embodiments, administering the therapeutically effective dose of the compound, or pharmaceutically acceptable salt, solvate, hydrate, or prodrug thereof, comprises administering an amount of a pharmaceutical composition comprising the therapeutically effective dose of the compound to the subject. Administering may be performed by an oral, parenteral, transmucosal, or transdermal route. In certain embodiments, administering is performed by an oral, intramuscular, subcutaneous, intravenous, or intra-arterial route.

In some embodiments, the therapeutically effective dose is administered on a daily basis or a weekly basis. The therapeutically effective dose may be administered as a single dose, or may be administered in two or more divided doses at intervals throughout a day. Amelioration of the at least one sign or symptom of the cardiac arrhythmia or heart failure in the subject may be realized after administration of a single therapeutically effective dose or after administration of two or more therapeutically effective doses over a period of time.

In any or all of the above embodiments, a compound as disclosed herein may be co-administered with an additional therapeutic agent. Suitable additional therapeutic agents include, but are not limited to, anti-arrhythmia agents, anti-hypertension agents, antimicrobial agents, anti-inflammatory agents, anesthetics, and the like. The compound and the additional therapeutic agent may be co-administered simultaneously or sequentially in any order. If administered simultaneously, the compound and the additional therapeutic agent may be administered together in a single pharmaceutical composition, or the compound and additional therapeutic agent may be administered in separate pharmaceutical compositions by the same or different routes of administration.

V. REPRESENTATIVE EMBODIMENTS

Certain embodiments are described below in the following numbered clauses:

1. A compound according to formula I or a stereoisomer, tautomer, or pharmaceutically acceptable salt thereof:

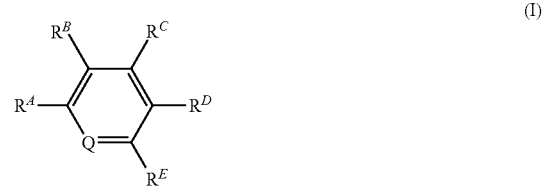

(I)

wherein $H_2N(R^1)$— and $R^A$ together with $R^B$ forms a 5- or 6-membered heteroaliphatic or heteroaryl ring; $R^C$ is H, aliphatic, or —O—C(O)-aliphatic, and $R^D$ is substituted aliphatic or —Y—X—$(CH_2)_m$—$N(R^4)R^5$, or $R^C$ and $R^D$ together form a 5- or 6-membered heteroaliphatic or heteroaryl ring; $R^E$ is H, aliphatic, —O-aliphatic, or —O—C(O)-aliphatic; Q is N or C—$R^3$; $R^1$ and $R^2$ independently are H or aliphatic; $R^3$ is H, aliphatic, or —O-aliphatic; $R^4$ and $R^5$ independently are H, aliphatic, or aryl; X is absent, N(H), O, C(O), —S($O_2$)O—, —OS($O_2$)—, —P(O)(OH)O—, —OP(O)(OH)—, —N(H)—C(H)($CF_3$)— or —C(H)($CF_3$)—N(H)—; Y is —$(CH_2)_n$— or a divalent azole ring; and m and n independently are integers from 1 to 10, wherein if X is absent, then Y is not —$(CH_2)_n$—.

2. The compound according to clause 1, wherein $R^D$ is —Y—X—$(CH_2)_m$—$N(R^4)R^5$.

3. The compound according to clause 1, wherein the compound has a structure according to one of formulas II, III, IV, or V:

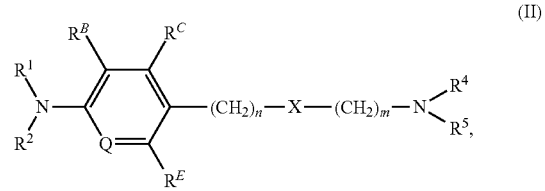

(II)

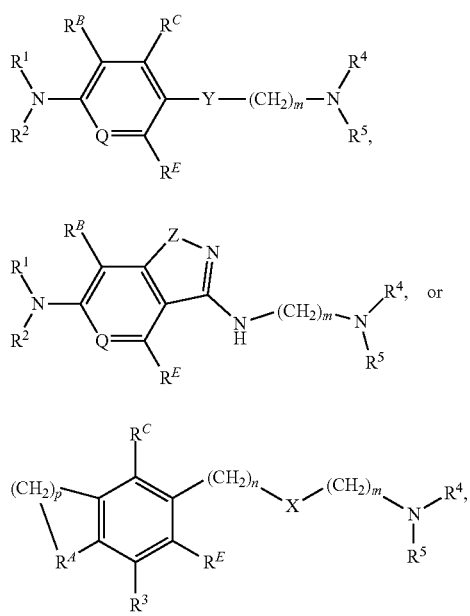

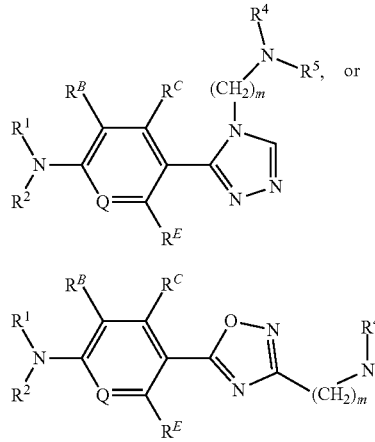

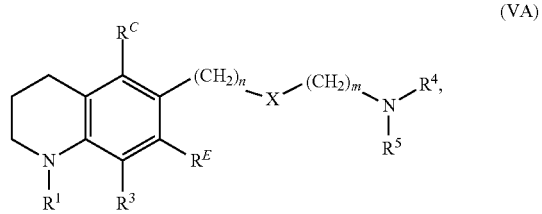

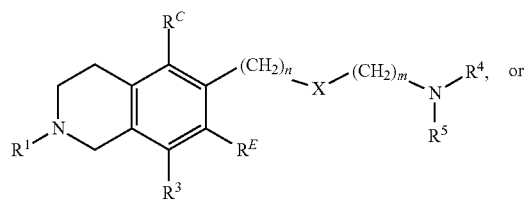

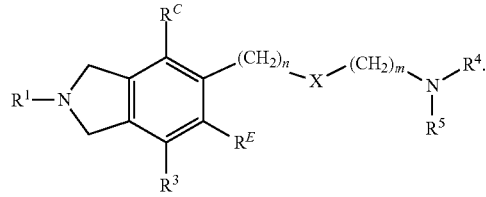

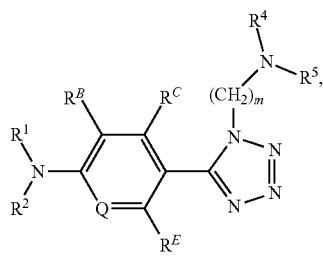

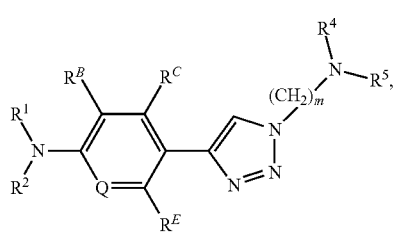

wherein $R^A$ is $N(R^1)$ or —$CH_2N(R^1)$—; $R^B$ is H, aliphatic, —O-aliphatic, or halogen; $R^C$ is H or aliphatic; X is N(H), O, C(O), —$S(O_2)O$—, —$OS(O_2)$—, —$P(O)(OH)O$—, —$OP(O)(OH)_3$, —N(H)—C(H)(CF_3)— or —C(H)(CF_3)—N(H)—; Y is an azole; Z is O, N(H), or CH_2; and p is 1, 2, or 3 when $R^A$ is $N(R^1)$, or p is 1 or 2 when $R^A$ is —$CH_2N(R^1)$—.

4. The compound of clause 3, wherein the compound has a structure according to formula III, and Y is an imidazolyl, pyrazolyl, triazolyl, tetrazolyl, oxazolyl, isoxazolyl, oxadiazolyl, furazanyl, thiazolyl, isothiazolyl, or thiadiazolyl group.

5. The compound of clause 3, wherein the compound has a structure according to one of formulas IIIA, IIIB, IIIC, or IIID:

6. The compound of any one of clauses 1-5, wherein Q is C—$R^3$.

7. The compound of clause 3, wherein the compound has a structure according to one of formulas VA, VB, or VC:

8. The compound according to clause 7, wherein $R^1$ is H or alkyl and: (i) $R^4$ and $R^5$ are H; or (ii) $R^4$ is H and $R^5$ is alkyl.

9. The compound according to any one of clauses 1-7, wherein $R^4$ and $R^5$ are alkyl.

10. The compound of any one of clauses 3-9, wherein $R^C$ is H.

11. The compound according to any one of clauses 2-10, wherein m is 2.

12. The compound according to any one of clauses 2-11, wherein n is 1.

13. The compound according to any one of clauses 2-12, wherein X is N(H), O, C(O), —$S(O_2)O$—, —OS (O₂)—, —P(O)(OH)O—, —OP(O)(OH)₃, —N(H)—C(H)(CF₃)—, or —C(H)(CF₃)—N(H)—.
14. The compound according to any one of clauses 2-12, wherein X is N(H), O, C(O), —S(O₂)O—, or —P(O)(OH)O—.
15. The compound according to any one of clauses 2-12, wherein X is N(H), O, or —S(O₂)O—.
16. The compound according to clause 1, wherein: $R^A$ is —N(R¹)R² where R¹ is H or aliphatic and R² is H or aliphatic; $R^B$ is H, aliphatic, —O-aliphatic, —O—C(O)-aliphatic, or halogen; $R^C$ is H, aliphatic, or —O—C(O)-aliphatic; and $R^D$ is substituted aliphatic.
17. The compound according to clause 16, wherein $R^D$ is aminoalkyl, hydroxyalkyl, or —(CH₂)$_q$SO₃M where q is an integer from 1 to 10 and M is a monatomic cation.
18. The compound according to clause 16, wherein $R^D$ is —CH₂SO₃M, —CH₂NH₂, or —CH₂OH.
19. A pharmaceutical composition, comprising: a therapeutically effective amount of at least one compound according to any one of clauses 1-18 or a pharmaceutically acceptable salt thereof; and at least one pharmaceutically acceptable additive.
20. A method for modulating activity of a calcium ion channel, comprising: contacting the calcium ion channel with an effective amount of a compound according to any one of clauses 1-18 or a pharmaceutically acceptable salt thereof.
21. The method of clause 20, wherein contacting the calcium ion channel with the compound inhibits activity of the calcium ion channel
22. The method of clause 20 or clause 21, wherein the calcium ion channel is a ryanodine receptor.
23. The method of clause 22, wherein the ryanodine receptor is RyR2.
24. The method of any one of clauses 20-23, wherein contacting the calcium ion channel is performed in vivo.
25. The method of clause 24, wherein contacting the calcium ion channel comprises administering the effective amount of the compound or pharmaceutically acceptable salt thereof to a subject identified as having, or being at risk of having, a cardiac arrhythmia or heart failure.
26. The method of clause 25, wherein administering the effective amount of the compound or pharmaceutically acceptable salt thereof comprises administering an amount of a pharmaceutical composition comprising the effective amount of the compound to the subject.
27. A method for ameliorating at least one sign or symptom of a cardiac arrhythmia or heart failure, the method comprising: administering one or more therapeutically effective doses of a compound according to any one of clauses 1-18 or a pharmaceutically acceptable salt thereof over an effective period of time to a subject identified as having, or being at risk of having, a cardiac arrhythmia or heart failure, thereby ameliorating at least one sign or symptom of the cardiac arrhythmia or heart failure.
28. The method of clause 27, wherein administering the therapeutically effective dose of the compound or pharmaceutically acceptable salt thereof comprises administering an amount of a pharmaceutical composition comprising the therapeutically effective dose of the compound to the subject.
29. The method of clause 27 or clause 28, wherein administering is performed by an oral, parenteral, transmucosal, or transdermal route.
30. The method of any one of clauses 27-29, wherein administering is performed by an oral, intramuscular, subcutaneous, intravenous, or intra-arterial route.

VI. EXAMPLES

Example 1

Synthesis of Representative Compounds

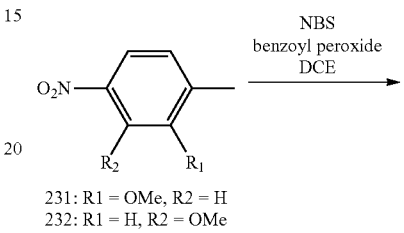

231: R1 = OMe, R2 = H
232: R1 = H, R2 = OMe

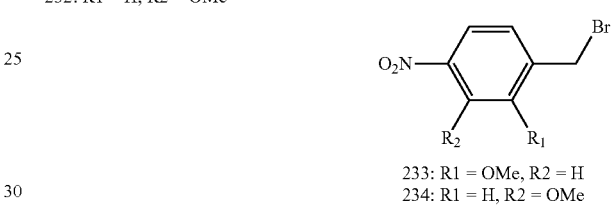

233: R1 = OMe, R2 = H
234: R1 = H, R2 = OMe

Synthesis of 1-(bromomethyl)-2-methoxy-4-nitrobenzene, (233). 2-methoxy-1-methyl-4-nitrobenzene (20.2 g, 118 mmol) was dissolved in 500 ml of anhydrous DCE, Ar was bubbled through the mixture for 5 min. N-bromosuccinimide (23.2 g, 129 mmol) was added to the flask and stirred for 5 min Benzoyl peroxide (1.89 g, 5.85 mmol) was added to the flask and stirred for 5 min. The flask was heated to 90° C. and a lamp was angled toward the flask for direct illumination. The reaction mixture was stirred for 24 h under Ar. The mixture was then cooled to room temperature. The mixture was poured into a one liter separatory funnel and washed with H₂O (100 ml). The aqueous layer was extracted with CH₂Cl₂ (3×50 ml). The combined organic extracts were washed with brine (250 ml), dried over Na₂SO₄, filtered, and concentrated under vacuum. The crude mixture was separated by flash column chromatography on silica gel using a EtOAc:Hexanes gradient from 0% EtOAc to 10% EtOAc. Yield 13.1 g (45%). ¹H NMR (400 MHz, Chloroform-d) δ 7.82 (dd, J=8.3, 2.2 Hz, 1H), 7.74 (d, J=2.1 Hz, 1H), 7.49 (d, J=8.3 Hz, 1H), 4.54 (s, 2H), 4.00 (s, 3H).

Synthesis of 4-(bromomethyl)-2-methoxy-1-nitrobenzene, (234). A solution of 2-methoxy-4-methyl-1-nitrobenzene (25 g, 149.6 mmols), N-bromosuccinimide (29.28 g, 164.5 mmols) and benzoyl peroxide (3.62 g, 14.96 mmols) in 1,2-dichloroethane (120 ml) under Ar atmosphere was heated under reflux for 16 h. The mixture was allowed to cool down to room temperature, then placed on an ice bath at 0° C. The precipitate formed was filtered, the filtrate was evaporated under vacuum to leave a yellow solid. The crude solid was purified by recrystallization using a mixture of EtOAc:Hexanes 9:1. Yield 36 g (97%). ¹H NMR (400 MHz, CDCl₃) δ 7.82 (d, J=8.3 Hz, 1H), 7.10 (d, J=1.6 Hz, 1H), 7.09-7.02 (m, 1H), 4.46 (s, 2H), 3.98 (s, 3H).

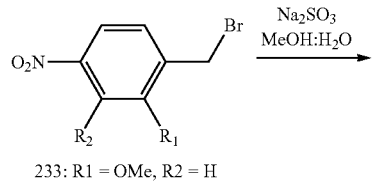

233: R1 = OMe, R2 = H
234: R1 - H, R2 = OMe

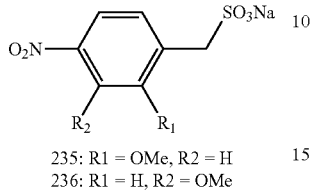

235: R1 = OMe, R2 = H
236: R1 = H, R2 = OMe

Synthesis of sodium (2-methoxy-4-nitrophenyl)methanesulfonate, (235). 1-(bromomethyl)-2-methoxy-4-nitrobenzene (10 g, 40.6 mmols) and sodium sulfite (5.63 g, 44.7 mmols) were dissolved in 20 ml of a mixture methanol:water 1:1. The solution was heated at 100° C. for 16 h. Additional 100 mg of sodium sulfite were added and heating continued for additional 10 h. The solvent was removed under vacuum. Ethanol (20 ml) was added, the precipitate formed was filtered and dried. The crude product was used as is without further purification. Yield 8.5 g (78%). $^1$H NMR (400 MHz, D$_2$O) δ 7.88 (dt, J=3.6, 2.1 Hz, 2H), 7.59 (d, J=8.2 Hz, 1H), 4.36 (s, 2H), 3.97 (s, 3H).

Synthesis of sodium (3-methoxy-4-nitrophenyl)methanesulfonate, (236). The title compound was prepared as described above for compound 235. 4-(bromomethyl)-2-methoxy-1-nitrobenzene (15 g, 60.96 mmols) and sodium sulfite (8.45 g, 67 mmols) were dissolved in 60 ml of a mixture methanol:water 1:1. The crude product was used as is without further purification. Yield 12.7 g (77%). NMR (400 MHz, DMSO) δ 7.77 (d, J=8.3 Hz, 1H), 7.29 (d, J=1.1 Hz, 1H), 7.05 (dd, J=8.3, 1.4 Hz, 1H), 3.89 (d, J=6.2 Hz, 3H), 3.83 (s, 2H).

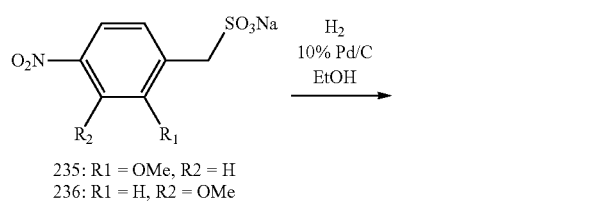

235: R1 = OMe, R2 = H
236: R1 = H, R2 = OMe

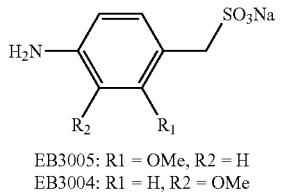

EB3005: R1 = OMe, R2 = H
EB3004: R1 = H, R2 = OMe

Synthesis of sodium (4-amino-2-methoxyphenyl)methanesulfonate (EB3005). Sodium (2-methoxy-4-nitrophenyl)methanesulfonate (4.3 g, 15.97 mmols) was dissolved in 40 ml of a mixture ethanol:water 3:1 under Ar atmosphere. The solution was flushed with Ar for 5 min, then 10% Pd/C (400 mg) was added in one portion. The mixture was flushed with H$_2$ and the mixture stirred at room temperature for 24 h under H$_2$ at atmospheric pressure. The mixture was filtered through a Celite® diatomaceous earth pad, the filtrate was evaporated under vacuum. The crude mixture was separated by flash column chromatography on silica gel using EtOAc:MeOH 55:45 for elution. The fraction containing the target product is further purified by preparative silica TLC using a mixture EtOAc:MeOH 60:40 for elution. Yield 2.1 g (54%). $^1$H NMR (400 MHz, D$_2$O) δ 7.08 (d, J=5.4 Hz, 1H), 6.41 (d, J=23.7 Hz, 2H), 4.04 (s, 2H), 3.73 (s, 3H). $^{13}$C NMR (101 MHz, D$_2$O) δ 158.49, 147.91, 132.64, 110.45, 108.43, 100.17, 55.68, 50.34.

Synthesis of Sodium (4-amino-3-methoxyphenyl)methanesulfonate, (EB3004). The title compound was prepared as described above for compound EB3005. Sodium (3-methoxy-4-nitrophenyl)methanesulfonate (6 g, 22.3 mmols) was dissolved in ethanol (400 ml) and water (2 ml) 500 mg of 10% Pd/C were used. Yield 5.08 g (95%). $^1$H NMR (400 MHz, D$_2$O) δ 7.01 (d, J=1.2 Hz, 1H), 6.96-6.78 (m, 2H), 4.09 (s, 2H), 3.89 (s, 3H). $^{13}$C NMR (101 MHz, MeOD) δ 148.74, 136.99, 124.38, 124.14, 116.21, 113.77, 58.46, 56.09, 49.00.

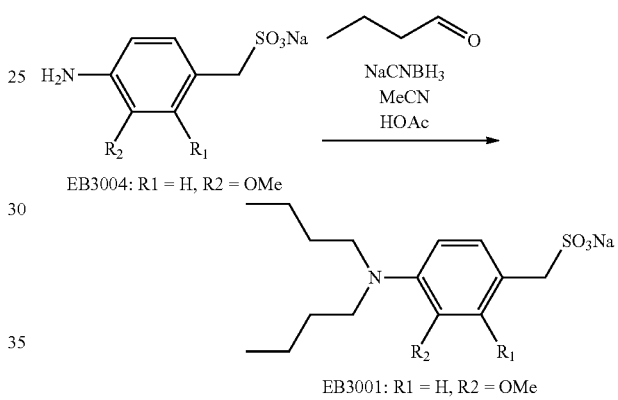

EB3004: R1 = H, R2 = OMe

EB3001: R1 = H, R2 = OMe

Synthesis of sodium (4-(dibutylamino)-3-methoxyphenyl)methanesulfonate, (EB3001).

Sodium (4-amino-3-methoxyphenyl)methanesulfonate, EB3004 (360 mg, 1.5 mmols) and butyraldehyde (142.6 mg, 1.66 mmol), were dissolved in 4 ml of a mixture water:methanol 1:3. Sodium cyano borohydride (104 mg, 1.66 mmols) was added in one portion. The reaction mixture was stirred at room temperature overnight. The solvent was evaporated under vacuum, the crude mixture was separated by flash column chromatography on silica gel using EtOAc:MeOH 70:30 for elution. The isolated fraction containing the title compound was further purified by preparative silica TLC using EtOAc:MeOH 70:30 for elution. Yield 51 mg (9.6%). $^1$H NMR (400 MHz, MeOD) δ 7.06 (s, 1H), 6.95 (d, J=2.6 Hz, 2H), 4.02 (s, 2H), 3.86 (s, 3H), 3.12-2.93 (m, 4H), 1.44-1.16 (m, 8H), 0.87 (t, J=7.3 Hz, 6H). $^{13}$C NMR (101 MHz, MeOD) δ 155.19, 123.96, 123.32, 123.06, 122.91, 115.47, 58.23, 55.94, 54.45, 30.19, 21.50, 14.33.

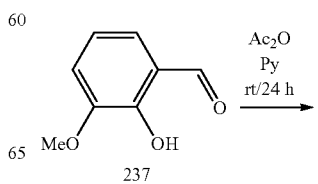

237

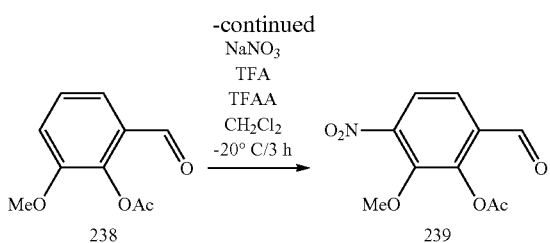

Synthesis of 2-formyl-6-methoxyphenyl acetate, (238). 2-hydroxy-3-methoxy benzaldehyde, 237 (50 g, 328.6 mmols) was dissolved in 150 ml of pyridine under Ar atmosphere. Acetic anhydride (39.96 g, 391.42 mmols) was added dropwise. The reaction mixture was stirred at room temperature for 24 h. The reaction mixture was poured onto ice (1 kg), allowed to warm to room temperature and extracted with $CH_2Cl_2$ (2000 ml), washed with 4.0 M HCl (1×2000 ml) and brine (1×2000 ml). The organic layer was dried over $Na_2SO_4$, filtered and the solvent evaporated under vacuum. Trituration of the crude with hexanes affords the target product containing residual pyridine. Residual pyridine was removed by washing the precipitate with water followed by drying under vacuum. Yield 45.1 g (71%). $^1$H NMR (400 MHz, $CDCl_3$) δ 10.12 (s, 1H), 7.45 (dd, J=7.8, 1.5 Hz, 1H), 7.30-7.28 (m, 1H), 7.21 (dd, J=8.2, 1.4 Hz, 1H), 3.86 (s, 93H), 2.39 (s, 3H).

Synthesis of 6-formyl-2-methoxy-3-nitrophenyl acetate, (239). In a one liter three neck flask 2-formyl-6-methoxyphenyl acetate, 238 (26 g, 133.9 mmols) was suspended in 110 ml of anhydrous $CH_2Cl_2$ under Ar atmosphere. $NaNO_3$ (15 g, 176.5 mmols) was added in one portion. The suspension was cooled to −20° C. using a dry ice/acetone bath. Trifluoro acetic acid (44.7 g, 392 mmols) was added dropwise over a period of 30 min while keeping the temperature at −20° C. Trifluoro acetic anhydride (171.35 g, 815.8 mmols) was added dropwise over a period of 30 min, while keeping the temperature at −20° C. The mixture was stirred at −20° C. for 2 h, then at −10° C. for 2 h. 500 ml of water were added to quench the reaction at −10° C., then the mixture was allowed to warm to room temperature and diluted with 500 ml of $CH_2Cl_2$. Phases were separated, the organic layer was washed with saturated $NaHCO_3$ (2×250 ml), brine (2×250 ml), dried over $Na_2SO_4$, filtered and the solvent evaporated under vacuum to leave a yellow residue. The title compound was purified by flash column chromatography on silica gel using EtOAc:Hexanes 1:1 for elution. Yield 10.1 g (32%). $^1$H NMR (400 MHz, $CDCl_3$) δ 10.18 (m, 1H), 7.84-7.77 (m, 1H), 7.72 (d, J=8.5 Hz, 1H), 3.99 (s, 3H), 2.47 (s, 3H).

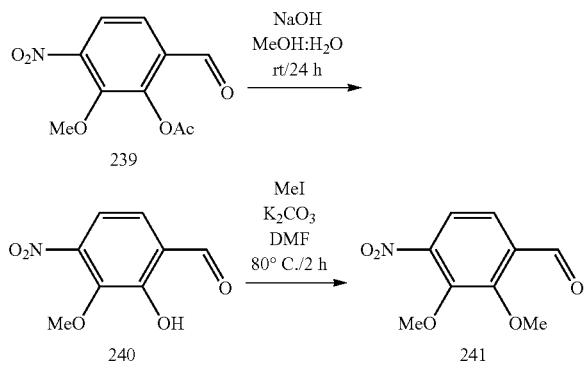

Synthesis of 2-hydroxy-3-methoxy-4-nitrobenzaldehyde, (240). 6-formyl-2-methoxy-3-nitrophenyl acetate, 239 (25 g, 104.5 mmols) was dissolved in 50 ml of MeOH. 20 ml of 2N NaOH were added. The mixture was stirred at room temperature overnight. The organic solvent was evaporated under vacuum. The aqueous residue was cooled down on an ice bath and acidified with conc. HCl to pH 2-3. The precipitate obtained was filtered, washed with cold water, and dried under vacuum to afford the title compound. Yield 18.1 g (88%). $^1$H NMR (400 MHz, $CDCl_3$) δ 11.38 (s, 1H), 9.98 (s, 1H), 7.43 (d, J=8.5 Hz, 1H), 7.28 (d, J=8.4 Hz, 1H), 4.07 (s, 3H). Synthesis of 4-Nitro-2,3-dimethoxybenzaldehyde, (241). 2-hydroxy-3-methoxy-4-nitrobenzaldehyde, 240 (7.5 g, 38 mmols) was dissolved in 30 ml of anhydrous DMF under Ar; $K_2CO_3$ (8.41 g, 60.85 mmols) was added in one portion, followed by the addition of methyl iodide (8.64 g, 60.9 mmols). The reaction mixture was heated at 80° C. for 2 h, allowed to cool down to room temperature and then poured into ice (40 g). The mixture was extracted with EtOAc (2×200 ml), the organic layers were combined, dried over $Na_2SO_4$, filtered and the solvent evaporated under vacuum. The crude product was consistent with the title compound and used as is without further purification. Yield 7.0 g (87%). $^1$H NMR (400 MHz, $CDCl_3$) δ 10.38 (d, J=0.8 Hz, 1H), 7.64 (d, J=8.6 Hz, 1H), 7.50 (dd, J=8.6, 0.8 Hz, 1H), 4.07 (s, 3H), 4.02 (s, 3H).

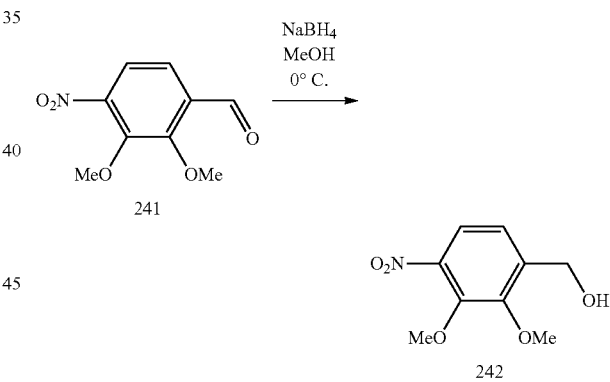

Synthesis of (2,3-dimethoxy-4-nitrophenyl)methanol, (242). 4-Nitro-2,3-dimethoxybenzaldehyde, 241 (7 g, 33.15 mmols) was dissolved in anhydrous methanol (50 ml) under Ar. The solution was cooled at 0° C. in an ice bath. $NaBH_4$ (1.25 g, 33.15 mmols) was added portion-wise. The mixture was stirred at 0° C. for 4 h. The mixture was allowed to warm to room temperature and the solvent evaporated under vacuum. The residue was dissolved in water (10 ml) and extracted with ethyl acetate (3×15 ml). The organic phases were combined, dried over $Na_2SO_4$, filtered and the solvent evaporated under vacuum to give the title compound. Yield 4.5 g (64%). $^1$H NMR (400 MHz, $CDCl_3$) δ 7.55 (d, J=8.5 Hz, 1H), 7.25 (d, J=5.1 Hz, 1H), 4.75 (d, J=6.1 Hz, 2H), 3.99 (s, 3H), 3.95 (s, 3H), 2.10 (t, J=6.1 Hz, 1H).

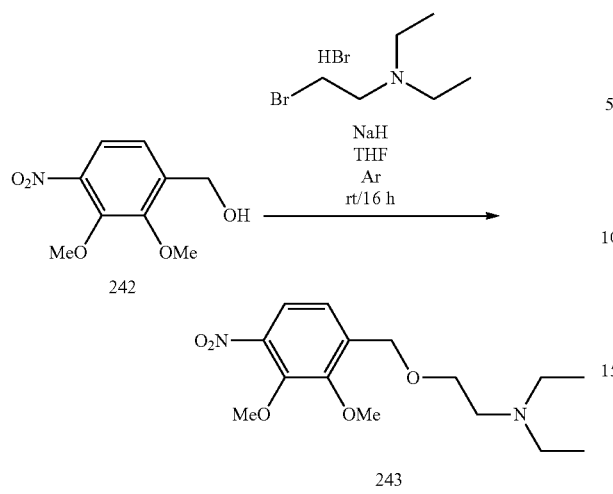

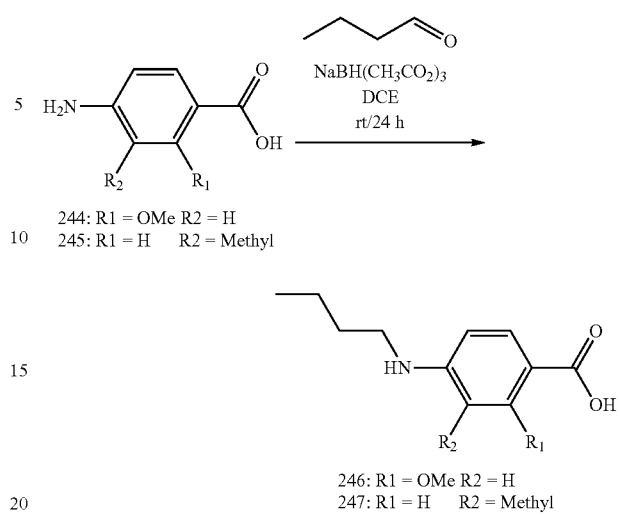

Synthesis of 2-((2,3-dimethoxy-4-nitrobenzyl)oxy)-N,N-diethylethanamine, (243). (2,3-dimethoxy-4-nitrophenyl)methanol, 242 (800 mg, 3.75 mmols) was dissolved in 10 ml of anhydrous THF under Ar. 2-bromo-N,N-diethylethanamine hydrobromide (979 mg, 3.75 mmols) was added in one portion followed by portion wise addition of 60% NaH (450.3 mg, 11.26 mmols). The mixture was stirred at room temperature for 16 h. Water (10 ml) was added slowly to quench the reaction. The mixture was extracted with ethyl acetate (3×15 ml). The organic phases were combined, dried over $Na_2SO_4$, filtered and the solvent evaporated under to get the title product. Yield 500 mg (43%). $^1H$ NMR (400 MHz, Chloroform-d) δ 7.55 (d, J=8.6 Hz, 1H), 7.49 (d, J=8.6 Hz, 1H), 4.40 (t, J=6.3 Hz, 2H), 4.02 (s, 3H), 3.97 (s, 3H), 2.83 (t, J=6.3 Hz, 2H), 2.61 (q, J=7.1 Hz, 4H), 1.05 (t, J=7.1 Hz, 6H).

Synthesis of 4-(butylamino)-2-methoxybenzoic acid, (246). 4-amino-2-methoxybenzoic acid, 244 (4.8 g, 28.7 mmols) and butyraldehyde (2.07 g, 28.7 mmols) were dissolved in 96 ml of anhydrous 1,2-dichloroethane under Ar atm. Sodium triacetoxyborohydride (9.13 g, 43.1 mmols) was added in one portion followed by the addition of acetic acid (1.725 g, 28.7 mmols). The mixture was stirred at room temperature overnight. The solution was diluted with 300 ml of EtOAc; 300 ml of saturated $NaHCO_3$ were added and the mixture stirred 15 min at room temperature. Phases were separated, the organic phase was washed with saturated solution of $NaHCO_3$ (2×300 ml). The organic phase was dried over $Na_2SO_4$, filtered and the solvent evaporated under vacuum. The precipitate obtained was triturated with hexanes (300 ml), EtOAc:Hex 5:95 (100 ml); EtOAc:Hex 10:90 (100 ml), and then dried under vacuum. Yield 3.64 g (57%). $^1H$ NMR (400 MHz, $CDCl_3$) δ 7.93 (d, J=8.7 Hz, 1H), 6.27 (dd, J=8.7, 2.1 Hz, 1H), 6.09 (d, J=2.1 Hz, 1H), 4.00 (d, J=2.5 Hz, 3H), 3.17 (t, J=7.1 Hz, 2H), 1.62 (ddd, J=12.4, 8.4, 6.5 Hz, 2H), 1.43 (dq, J=14.4, 7.3 Hz, 2H), 0.96 (dd, J=8.2, 6.5 Hz, 3H). $^{13}C$ NMR (101 MHz, $CDCl_3$) δ 166.57, 160.59, 154.75, 135.82, 106.66, 105.93, 94.51, 56.78, 43.60, 31.81, 20.73, 14.36.

Synthesis of 4-amino-3-methylbenzoic acid, (247). The title compound was prepared as described above for compound 246. 4-Amino-3-methylbenzoic acid, 245 (4.9 g, 32.41 mmols), butyraldehyde (3.51 g, 48.62 mmols), sodium triacetoxyborohydride (10.31 g, 48.62 mmols), acetic acid (1.95 g, 32.41 mmols). Anhydrous 1,2-dichloroethane (90 ml). Yield 5.3 g (79%). $^1H$ NMR (400 MHz, $CDCl_3$) δ 7.91 (dd, J=8.5, 2.0 Hz, 1H), 7.80 (d, J=1.2 Hz, 1H), 6.58 (d, J=8.6 Hz, 1H), 3.23 (t, J=7.1 Hz, 1H), 2.15 (s, 1H), 1.73-1.60 (m, 1H), 1.46 (dq, J=14.5, 7.3 Hz, 1H), 0.99 (t, J=7.3 Hz, 2H). $^{13}C$ NMR (101 MHz, $CDCl_3$) δ 172.71, 151.01, 132.27, 130.85, 120.62, 116.55, 108.32, 43.31, 31.57, 20.42, 17.34, 14.01.

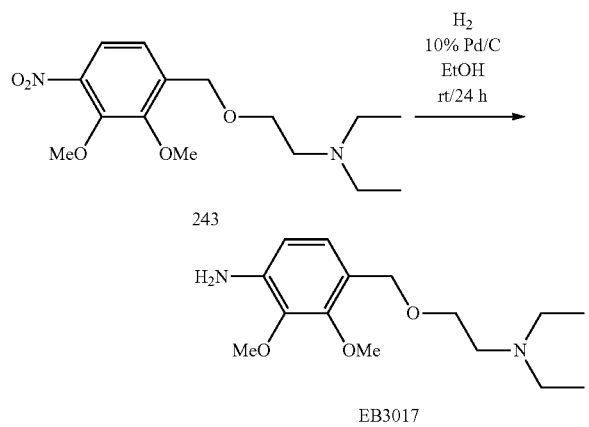

Synthesis of 4-((2-(diethylamino)ethoxy)methyl)-2,3-dimethoxyaniline, (EB3017). The title compound was prepared as described above for compound EB3005. 2-((2,3-dimethoxy-4-nitrobenzyl)oxy)-N,N-diethylethanamine, 243 (150 mg, 0.48 mmols) was dissolved in 10 ml of ethanol, glacial acetic acid (0.1 ml) was added in one portion. 50 mg of 10% Pd/C were used. Yield 59 mg, (44%). $^1H$ NMR (400 MHz, Chloroform-d) δ 6.85 (d, J=8.2 Hz, 1H), 6.46 (d, J=8.1 Hz, 1H), 4.41 (s, 2H), 3.85 (s, 3H), 3.84 (s, 3H), 3.65 (t, J=6.0 Hz, 2H), 2.87 (t, J=5.9 Hz, 2H), 2.77 (q, J=7.2 Hz, 4H), 1.10 (t, J=7.2 Hz, 6H).

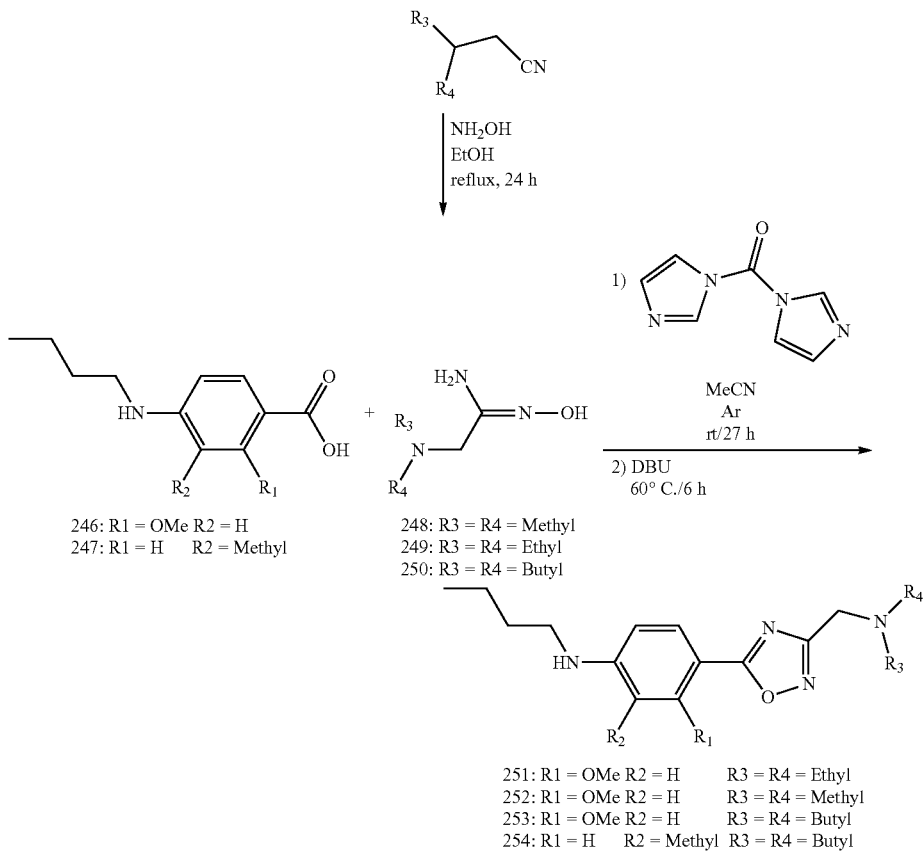

Synthesis of N-butyl-4-(3-((diethylamino)methyl)-1,2,4-oxadiazol-5-yl)-3-methoxyaniline, (251). Under Ar atmosphere, 4-(butylamino)-2-methoxybenzoic acid, 246 (121 mg, 0.542 mmols) was added to a solution of di(1H-imidazol-1-yl)methanone (88 mg, 0.542 mmols) in acetonitrile (2 ml). The mixture was stirred for 3 h at room temperature. 2-(diethylamino)-N'-hydroxyacetimidamide, 249 (75 mg, 0.516 mmols) was added to the reaction mixture and stirred for additional 24 h at room temperature. 1,8-Diazabicyclo[5.4.0]undec-7-ene (157 mg, 1.03 mmols) was added in one portion, and the reaction mixture heated at 60° C. for 6 h. The mixture was cooled to room temperature and diluted with water (50 ml). The aqueous phase was extracted with EtOAc (3×25 ml). The organic layers were combined, washed with saturated NaHCO$_3$ (50 ml), dried over Na$_2$SO$_4$, filtered and the solvent evaporated under vacuum. The crude mixture was separated on a SP1 Biotage® system on a 25 g SNAP KP-Sil cartridge using a EtOAc:MeOH gradient from 1% MeOH to 20% MeOH. Yield 43 mg (25%). $^1$H NMR (400 MHz, CDCl$_3$) δ 7.93 (d, J=8.7 Hz, 1H), 6.27-6.21 (m, 1H), 6.12 (d, J=2.1 Hz, 1H), 4.14 (d, J=20.5 Hz, 1H), 3.98-3.84 (m, 5H), 3.24-3.12 (m, 2H), 2.73 (s, 4H), 1.64 (dt, J=19.8, 7.3 Hz, 2H), 1.45 (dq, J=14.4, 7.3 Hz, 2H), 1.17 (s, 6H), 1.02-0.92 (m, 3H). $^{13}$C NMR (101 MHz, CDCl$_3$) δ 160.58, 153.63, 133.25, 105.22, 94.90, 55.88, 47.55, 43.24, 31.54, 20.36, 14.00, 11.87.

Synthesis of N-butyl-4-(3-((dimethylamino)methyl)-1,2,4-oxadiazol-5-yl)-3-methoxyaniline, (252). The title compound was prepared as described for compound 251. 4-(butylamino)-2-methoxybenzoic acid, 246 (150 mg, 0.672 mmols), di(1H-imidazol-1-yl)methanone (109 mg, 0.672 mmols), 2-(dimethylamino)-N'-hydroxyacetimidamide, 248 (75 mg, 0.64 mmols), 1,8-Diazabicyclo[5.4.0]undec-7-ene (194 mg, 1.28 mmols) in acetonitrile (2 ml). Yield 90 mg (46%). $^1$H NMR (400 MHz, CDCl$_3$) δ 7.95 (d, J=8.7 Hz, 1H), 6.24 (dd, J=8.7, 2.1 Hz, 1H), 6.12 (d, J=2.1 Hz, 1H), 4.17 (s, 1H), 3.93 (s, 3H), 3.67 (d, J=5.9 Hz, 2H), 3.19 (dd, J=10.9, 7.1 Hz, 2H), 2.39 (s, 6H), 1.63 (ddd, J=12.4, 8.4, 6.4 Hz, 2H), 1.45 (dq, J=14.4, 7.3 Hz, 2H), 0.98 (t, J=7.3 Hz, 3H). $^{13}$C NMR (101 MHz, CDCl$_3$) δ 175.82, 167.26, 160.57, 153.62, 133.30, 105.17, 102.02, 94.87, 55.87, 54.14, 45.46, 43.23, 31.54, 20.35, 13.98.

Synthesis of N-butyl-4-(3-((dibutylamino)methyl)-1,2,4-oxadiazol-5-yl)-3-methoxyaniline (253). The title compound was prepared as described for compound 251. 4-(butylamino)-2-methoxybenzoic acid, 246 (249 mg, 1.12 mmols) was added to a solution of di(1H-imidazol-1-yl)methanone (181 mg, 1.12 mmols), 2-(dibutylamino)-N'-hydroxyacetimidamide, 250 (225 mg, 1.12 mmols), 1,8-Diazabicyclo[5.4.0]undec-7-ene (340 mg, 2.24 mmols) in acetonitrile (4 ml). Yield 129 mg (30%). $^1$H NMR (400 MHz, Chloroform-d) δ 7.91 (d, J=8.7 Hz, 1H), 6.24 (dd, J=8.7, 2.1 Hz, 1H), 6.12 (d, J=2.1 Hz, 1H), 4.17 (s, 1H), 3.93 (s, 3H), 3.88 (s, 2H), 3.19 (q, J=7.0 Hz, 2H), 2.60 (s, 4H), 1.67-1.60 (m, 2H), 1.54 (s, 4H), 1.49-1.43 (m, 2H), 1.31 (dp, J=13.7, 7.0, 6.5 Hz, 4H), 0.98 (t, J=7.3 Hz, 3H), 0.91 (t, J=7.3 Hz, 6H). $^{13}$C NMR (101 MHz, CDCl$_3$) δ 160.54, 153.58, 133.16, 105.21, 94.93, 55.86, 53.92, 43.24, 31.54, 20.72, 20.36, 14.16, 13.99.

Synthesis of N-butyl-4-(3-((dibutylamino)methyl)-1,2,4-oxadiazol-5-yl)-2-methylaniline, (254). The title compound was prepared as described for compound 251. 4-(butylamino)-3-methylbenzoic acid, 247 (243 mg, 1.17 mmols) was added to a solution of di(1H-imidazol-1-yl)methanone (190 mg, 1.17 mmols), 2-(dibutylamino)-N-hydroxy-acetimidamide, 250 (225 mg, 1.12 mmols), 1,8-Diazabicyclo[5.4.0]undec-7-ene (340 mg, 2.24 mmols) in acetonitrile (4 ml). Yield 156 mg (62%). $^1$H NMR (400 MHz, CDCl$_3$) δ 7.90 (dd, J=8.5, 2.0 Hz, 1H), 7.82 (d, J=1.2 Hz, 1H), 6.64 (d, J=8.6 Hz, 1H), 3.96 (s, 1H), 3.84 (s, 2H), 3.24 (dd, J=12.3, 7.1 Hz, 2H), 2.58 (s, 4H), 2.17 (s, 3H), 1.74-1.41 (m, 8H), 1.39-1.23 (m, 4H), 0.99 (t, J=7.3 Hz, 3H), 0.91 (t, J=7.3 Hz, 6H). $^{13}$C NMR (101 MHz, CDCl$_3$) δ 176.20, 165.96, 162.88, 150.14, 130.09, 128.38, 121.49, 108.98, 53.96, 43.35, 31.58, 29.32, 20.74, 20.43, 17.33, 14.18, 14.02.

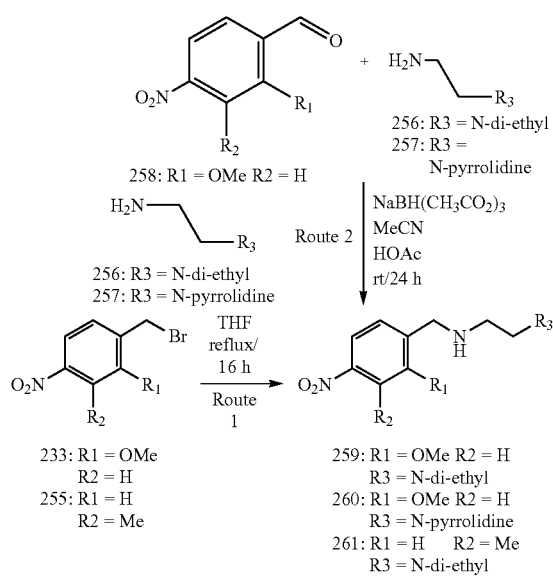

$N^1,N^1$-diethyl-$N^2$-(2-methoxy-4-nitrobenzyl)ethane-1,2-diamine, (259); Route 1. A 250 mL, round-bottomed flask equipped with a magnetic stir bar and a reflux condenser was charged with 1-(bromomethyl)-2-methoxy-4-nitrobenzene, 233 (6.7 g, 27 mmol) in 80 ml THF. $N^1,N^1$-diethylethane-1,2-diamine (16.1 g, 136 mmol) was added to the solution. The mixture was heated to 70° C. and stirred for 21 h. The flask was cooled to room temperature and concentrated under vacuum to remove the THF. The crude mixture was diluted to 75 ml with CH$_2$Cl$_2$ and 60 ml of 0.7 M NaOH was added. Phases were separated and the aqueous layer was extracted with CH$_2$Cl$_2$ (3×25 ml). The combined organic layers were washed with brine (100 ml), dried over Na$_2$SO$_4$, filtered, and concentrated under reduced pressure to give a dark red solution. The excess of amine in the crude material was removed by loading the crude onto a basic alumina column and eluted with a CH$_2$Cl$_2$:EtOH gradient from 1% EtOH to 5% EtOH. The fractions free of $N^1,N^1$-diethyl-ethane-1,2-diamine were combined and concentrated under reduced pressure for further purification by flash column chromatography on silica gel and eluted with a CH$_2$Cl$_2$:MeOH gradient from 1% MeOH to 70% MeOH. The fractions containing the title compound (R$_f$=0.6; NH$_4$OH basified plate 10% MeOH/CH$_2$Cl$_2$) were combined and concentrated under reduced pressure to give the title compound as a dark red oil (3.8 g, 50%). $^1$H NMR (400 MHz, Chloroform-d) δ 7.83 (d, J=8.2 Hz, 1H), 7.69 (s, 1H), 7.46 (d, J=8.2 Hz, 1H), 3.93 (s, 3H), 3.86 (s, 2H), 2.66 (t, J=6.0 Hz, 2H), 2.58 (t, J=6.0 Hz, 2H), 2.50 (q, J=7.2 Hz, 4H), 1.00 (t, J=7.1 Hz, 6H).

Synthesis of $N^1,N^1$-diethyl-$N^2$-(2-methoxy-4-nitrobenzyl)ethane-1,2-diamine, (259); Route 2. Under Ar, 2-Methoxy-4-nitrobenzaldehyde, 258 (242 mg, 1.34 mmols) was dissolved in 10 ml of anhydrous MeCN followed by the addition of N,N-diethylethyldiamine (156 mg, 1.34 mmols), 100 mg of 4 Å molecular sieves and sodium triacetoxyborohydride (284 mg, 1.34 mmols). The mixture was stirred for 10 min Acetic acid (80 mg, 1.34 mmols) was added in one portion, then the mixture stirred at room temperature for 24 h. The mixture was filtered, the solid was washed with MeCN (10 ml) and the filtrate evaporated under vacuum. The residue was dissolved in EtOAc (20 ml) and partitionated with water (20 ml). The organic layer was washed with 1N HCl (3×20 ml), the combined aqueous layers were basified with NaOH to pH 12-13 and extracted with CH$_2$Cl$_2$ (3×20 ml). The combined organic layers were washed with brine (15 ml), dried over Na$_2$SO$_4$, filtered and the solvent evaporated under vacuum. The residue obtained is consistent with the title compound.

Synthesis of N-(2-methoxy-4-nitrobenzyl)-2-(pyrrolidin-1-yl)ethan-1-amine, (260). 1-(bromomethyl)-2-methoxy-4-nitrobenzene, 233 (1.6 g, 6.50 mmols) was dissolved in 24 ml of THF. 1-(2-Aminoethyl)pyrrolidine (3.71 g, 32.5 mmols) was added in one portion. The mixture was refluxed overnight. The solvent was evaporated under vacuum. The residue was dissolved in 50 ml of DI water and 1 ml of 4N NaOH was added. The mixture was extracted with CHCl$_3$ (3×100 ml). The organic extracts were combined, dried over Na$_2$SO$_4$, filtered and the solvent evaporated under vacuum. The crude mixture was separated by flash column chromatography on a 50G KPSil SNAP cartridge, using a CH$_2$Cl$_2$:MeOH gradient from 2% to 20% MeOH on a SP1 Biotage system. Yield 1.18 g (65%). $^1$H NMR (400 MHz, CDCl$_3$) δ 7.82 (dd, J=8.2, 2.1 Hz, 1H), 7.69 (d, J=2.1 Hz, 1H), 7.46 (d, J=8.2 Hz, 1H), 3.92 (d, J=2.6 Hz, 3H), 3.87 (s, 2H), 2.72 (dd, J=9.5, 3.3 Hz, 2H), 2.61 (dd, J=9.6, 3.3 Hz, 2H), 2.50-2.43 (m, 4H), 1.79-1.72 (m, 4H).

Synthesis of $N^1,N^1$-diethyl-$N^2$-(3-methyl-4-nitrobenzyl)ethane-1,2-diamine, (261). 4-(bromomethyl)-2-methyl-1-nitrobenzene, 255 (991 mg, 4.31 mmols) was dissolved in 15 mL THF. $N^1,N^1$-diethylethane-1,2-diamine (2.5 g, 21.54 mmols) was added in one portion. The mixture was refluxed overnight at 80° C. The solvent was evaporated under vacuum. The title compound was isolated by flash column chromatography on a 50G KPSil SNAP cartridge, using a CH$_2$Cl$_2$:MeOH gradient from 2% to 20% MeOH on a SP1 Biotage® system. Yield 654 mg (57%). $^1$H NMR (400 MHz, CDCl$_3$) δ 7.95 (d, J=8.1 Hz, 1H), 7.29 (dd, J=9.6, 0.9 Hz, 2H), 3.84 (s, 2H), 2.70-2.64 (m, 2H), 2.63-2.59 (m, 5H), 2.59-2.52 (m, 4H), 1.07-1.00 (m, 6H).

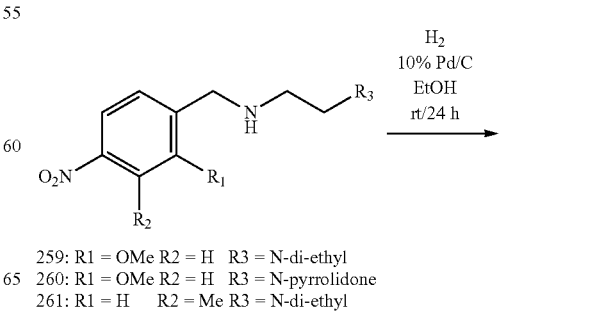

259: R1 = OMe R2 = H   R3 = N-di-ethyl
260: R1 = OMe R2 = H   R3 = N-pyrrolidone
261: R1 = H    R2 = Me R3 = N-di-ethyl

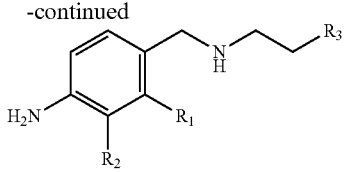

EB3019: R1 = OMe R2 = H R3 = N-di-ethyl
EB3021: R1 = OMe R2 = H R3 = N-pyrrolidone
EB3025: R1 = H R2 = Me R3 = N-di-ethyl Synthesis of $N^1$-(4-amino-2-methoxybenzyl)-$N^2$,$N^2$-diethylethane-1,2-diamine, (EB3019). $N^1$,$N^1$-diethyl-$N^2$-(2-methoxy-4-nitrobenzyl)ethane-1,2-diamine, 259 (5.1 g, 18.1 mmol) was dissolved in 600 ml of EtOH. Argon is bubbled through the solution for 15 min. 10% Palladium on carbon (1.93 g), was added in one portion, the mixture was flushed with $H_2$ and stirred under $H_2$ at atmospheric pressure at room temperature for 24 h. The suspension was filtered through a Celite® pad and the filtrate concentrated under reduced pressure to give an orange oil. The crude mixture was separated by flash column chromatography on a 100 g basic alumina SNAP cartridge on a SP1 Biotage® system and using a $CH_2Cl_2$:EtOH gradient from 0% EtOH to 10% EtOH. Yield 3.04 g (67%). $^1$H NMR (400 MHz, Chloroform-d) δ 6.99 (d, J=8.5 Hz, 1H), 6.22 (d, J=6.3 Hz, 2H), 3.77 (s, 3H), 3.69 (s, 2H), 3.63 (s, 1H), 2.64 (t, J=6.4 Hz, 2H), 2.55 (t, J=6.3 Hz, 2H), 2.47 (q, J=7.1 Hz, 4H), 0.97 (t, J=7.1 Hz, 6H). $^{13}$C NMR (101 MHz, CDCl$_3$) δ 158.79, 148.09, 131.83, 106.96, 98.26, 55.31, 51.31, 48.33, 46.70, 45.09, 11.71.

Synthesis of 3-methoxy-4-(((2-(pyrrolidin-1-yl)ethyl)amino)methyl)aniline, (EB3021). The title compound was prepared as described for compound EB3019. N-(2-methoxy-4-nitrobenzyl)-2-(pyrrolidin-1-yl)ethan-1-amine, 260 (1.18 g, 4.22 mmols) was dissolved in 75 ml of EtOH, 674.3 mg of 10% Pd/C were used. The crude mixture was purified by flash column chromatography on basic alumina using EtOAc, EtOAc:MeOH 9:1 for elution. Yield 189 mg (18%). $^1$H NMR (400 MHz, CDCl$_3$) δ 6.98 (d, J=8.5 Hz, 1H), 6.23 (dd, J=6.4, 2.1 Hz, 2H), 3.77 (s, 3H), 3.71 (s, 2H), 3.63 (s, 1H), 2.71 (t, J=6.3 Hz, 2H), 2.60 (t, J=6.2 Hz, 2H), 2.47-2.41 (m, 4H), 1.76-1.71 (m, 4H). $^{13}$C NMR (101 MHz, CDCl$_3$) δ 158.64, 146.94, 131.03, 106.63, 98.32, 55.65, 55.08, 54.05, 48.92, 47.33, 23.47.

Synthesis of $N^1$-(4-amino-3-methylbenzyl)-$N^2$,$N^2$-diethylethane-1,2-diamine, (EB3025). The title compound was prepared as described for compound EB3019. $N^1$,$N^1$-diethyl-$N^2$-(3-methyl-4-nitrobenzyl)ethane-1,2-diamine, 261 (650 mg, 2.45 mmols) was dissolved in 100 ml of EtOH. 391 mg of 10% Pd/C were used. The title compound was isolated by flash column chromatography on basic alumina using $CH_2Cl_2$, $CH_2Cl_2$:MeOH 99:1 for elution. Yield 294 mg (61%). 41 NMR (400 MHz, CDCl$_3$) δ 7.01 (s, 1H), 6.97 (dd, J=7.9, 1.7 Hz, 1H), 6.63 (d, J=7.9 Hz, 1H), 3.66 (s, 2H), 3.54 (s, 2H), 2.67 (dd, J=9.6, 3.3 Hz, 2H), 2.55 (dd, J=9.5, 3.3 Hz, 2H), 2.49 (q, J=7.1 Hz, 4H), 2.16 (s, 3H), 0.99 (t, J=7.1 Hz, 6H). $^{13}$C NMR (101 MHz, CDCl$_3$) δ 143.47, 130.86, 130.64, 126.97, 122.47, 115.01, 53.83, 52.81, 47.16, 47.00, 17.49, 11.96.

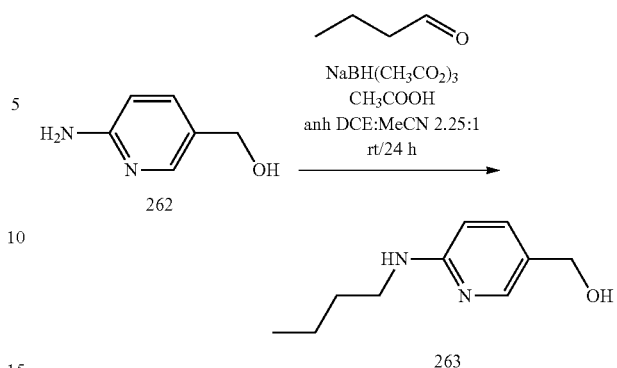

Synthesis of (6-(butylamino)pyridin-3-yl)methanol, (263). 2-Aminopyridine-5-methanol, 262 (766 mg, 6.17 mmols) and butyraldehyde (445 mg, 6.17 mmmols) were dissolved in 45 ml of anhydrous 1,2-dichloroethane and 20 ml of anhydrous MeCN. Sodium tri-acetoxyborohydride (1.31 g, 6.17 mmols) was added in one portion, followed by the addition of acetic acid (370 mg, 6.17 mmols). The mixture was stirred at room temperature 24 h. The mixture was diluted with 50 ml of EtOAc and then saturated solution of NaHCO$_3$ (60 ml) was added; the mixture was stirred 15 min. Phases were separated, the organic phase was dried over Na$_2$SO$_4$, filtered and the solvent evaporated under vacuum. Crude yield, 0.80439 g (72% yield), was consistent with the title compound and was used as is without further purification. $^1$H NMR (400 MHz, CDCl$_3$) δ 7.98 (d, J=2.0 Hz, 1H), 7.47 (dd, J=8.5, 2.4 Hz, 1H), 6.37 (d, J=8.5 Hz, 1H), 4.53 (m, 3H), 3.24 (td, J=7.1, 5.8 Hz, 2H), 1.64-1.54 (m, 2H), 1.42 (dq, J=14.4, 7.3 Hz, 2H), 0.95 (t, J=7.3 Hz, 3H). $^{13}$C NMR (101 MHz, CDCl$_3$) δ 158.85, 147.69, 137.82, 125.01, 106.38, 63.04, 42.21, 31.75, 20.32, 13.99.

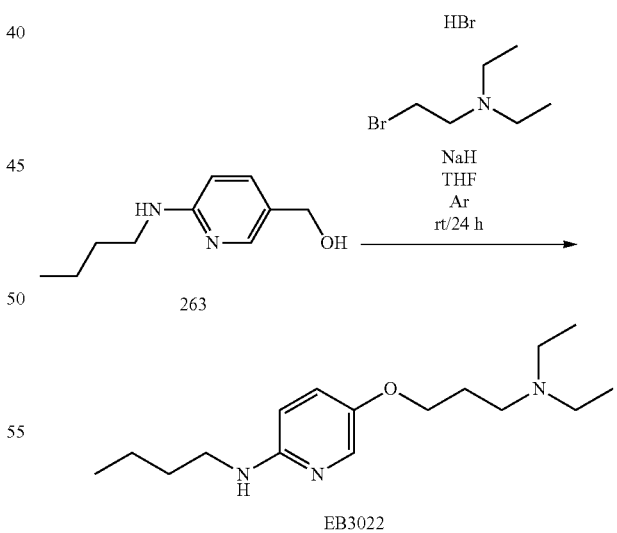

Synthesis of N-butyl-5-((2-(diethylamino)ethoxy)methyl)pyridin-2-amine, EB3022. (6-(butylamino)pyridin-3-yl)methanol, 263 (300 mg, 1.66 mmols) and 2-bromo-N,N-diethylethanamine hydrobromide (434 mg, 1.66 mmols) were dissolved in 10 ml of anh THF under Ar, at room temperature. 60% NaH (199.7 mg, 4.99 mmols) was added in one portion. The mixture was stirred at room temperature for 24 h. The mixture was quenched with 20 ml of cold water, then extracted with ethyl acetate (3×50 ml). The organic phases were combined, dried over $Na_2SO_4$, filtered and the solvent evaporated under vacuum. The crude mixture was separated by flash column chromatography on a 25G KPSil SNAP cartridge on a SP1 Biotage® system using a $CH_2Cl_2$:MeOH gradient from 7% MeOH to 60% MeOH. Yield 115 mg (25% yield). $^1$H NMR (400 MHz, $CDCl_3$) δ 8.01 (d, J=2.0 Hz, 1H), 7.43 (dd, J=8.5, 2.3 Hz, 1H), 6.36 (d, J=8.5 Hz, 1H), 4.54-4.46 (m, 1H), 4.36 (s, 2H), 3.52 (t, J=6.3 Hz, 2H), 3.25 (dt, J=12.8, 6.4 Hz, 2H), 2.67 (t, J=6.3 Hz, 2H), 2.57 (q, J=7.1 Hz, 4H), 1.59 (dd, J=8.6, 6.1 Hz, 2H), 1.42 (dd, J=15.1, 7.4 Hz, 2H), 1.02 (t, J=7.1 Hz, 6H), 0.95 (t, J=7.3 Hz, 3H). $^{13}$C NMR (101 MHz, $CDCl_3$) δ 158.86, 148.34, 138.22, 122.26, 106.28, 70.92, 68.21, 52.44, 47.67, 42.21, 31.79, 20.33, 14.00, 11.74.

washed with 10 ml of 1 N NaOH. The filtrate was treated with 20 ml of 3 N HCl; the precipitated tetrazole was filtered, washed with 3 N HCl (2×20 ml) and dried under vacuum. Yield 1.6 g (84%). $^1$H NMR (400 MHz, $CDCl_3$) δ 8.02 (d, J=8.3 Hz, 1H), 7.68 (s, 1H), 2.63 (s, 3H).

Synthesis of N,N-diethyl-2-(5-(3-methyl-4-nitrophenyl)-1H-tetrazol-1-yl)ethan-1-amine, (266). 5-(3-methyl-4-nitrophenyl)-1H-tetrazole, 265 (0.8 g, 3.9 mmols) was dissolved in 10 ml of MeCN; 2-bromo-N,N-diethylethan-1-amine hydrobromide (1.02 g, 3.90 mmols) and triethylamine (1.18 g, 11.7 mmols) were added. The mixture was stirred at room temperature for 16 h. $K_2CO_3$ (0.53 g, 3.9 mmols) was added and stirring continued for additional 16 h. The organic solvent was removed under vacuum, the aqueous residue was poured into ice; the precipitate formed was filtered and dried under vacuum to afford the title compound. Yield 460 mg (39%). $^1$H NMR (400 MHz, $CDCl_3$) δ 8.17 (d, J=0.6 Hz, 1H), 8.15-8.05 (m, 2H), 4.73 (t, J=6.8 Hz, 2H), 3.11 (t, J=6.8 Hz, 2H), 2.69 (s, 3H), 2.58 (q, J=7.1 Hz, 4H), 1.00 (t, J=7.1 Hz, 6H).

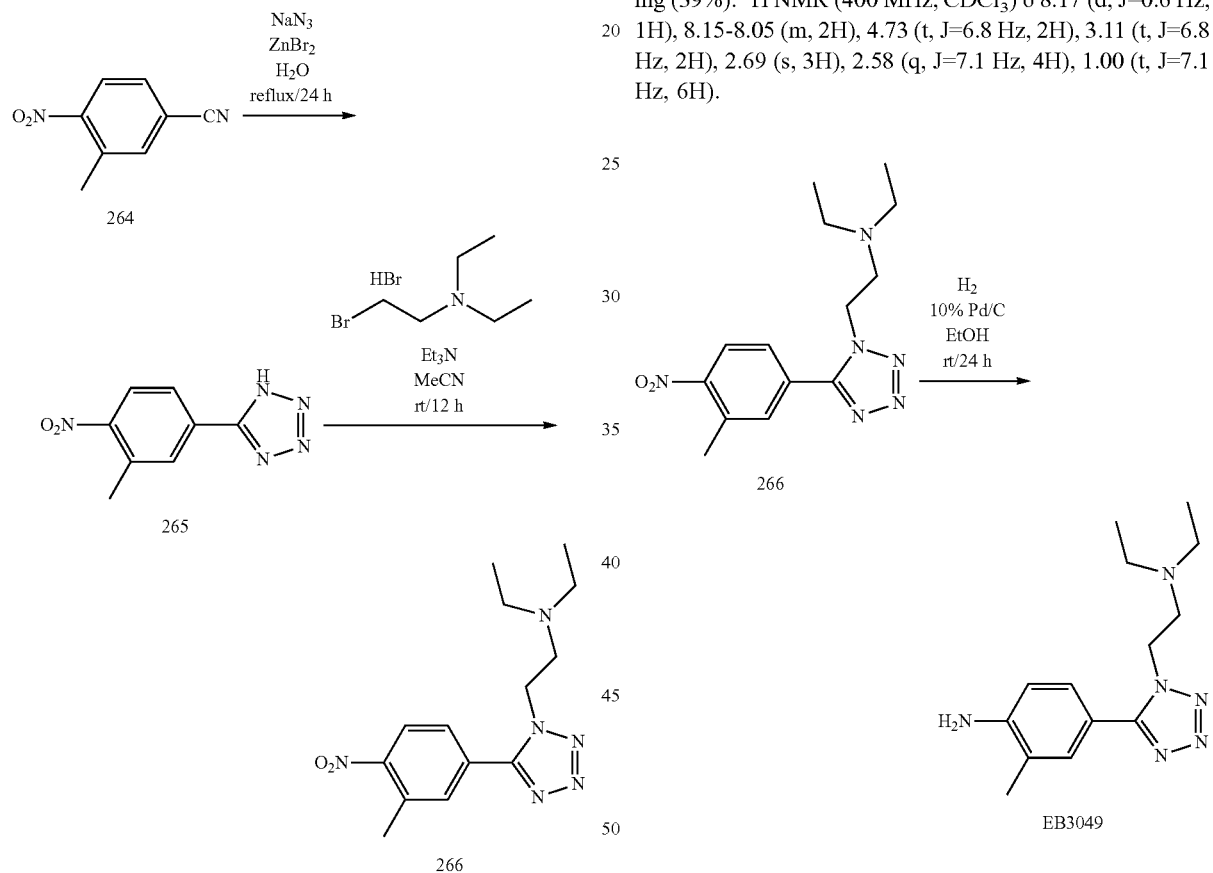

Synthesis of 5-(3-methyl-4-nitrophenyl)-1H-tetrazole, 265. 4-Cyano-3-methylnitrobenzene, 264 (1.5 g, 9.25 mmols) was suspended in 20 ml of water, sodium azide (0.661 g, 10.18 mmols) and zinc bromide (2.08 g, 9.25 mmols) were added. The reaction mixture was refluxed for 24 h with vigorous stirring. 15 ml of 3N HCl and ethyl acetate (50 ml) were added, vigorous stirring was continued until no solid was present and the aqueous layer had a pH of 1. Phases were separated and the aqueous layer extracted with EtOAc (2×50 ml). The combined organic layers were evaporated under vacuum. The residue was dissolved in 100 ml of 0.25 N NaOH, and the mixture stirred for 30 min, until the original precipitate dissolved and a suspension of zinc hydroxide formed. The suspension was filtered, and the solid Synthesis of 4-(1-(2-(diethylamino)ethyl)-1H-tetrazol-5-yl)-2-methylaniline, (EB3049). The title compound was prepared as described above for compound EB3005. N,N-diethyl-2-(5-(3-methyl-4-nitrophenyl)-1H-tetrazol-1-yl)ethan-1-amine, 266 (460 mg, 1.51 mmols) was dissolved in 15 ml of ethanol, 75 mg 10% Pd/C were used. The crude mixture was separated by flash column chromatography on silica gel using EtOAc:Hexanes 70:30 for elution. Yield 320 mg (77%). $^1$H NMR (400 MHz, $CDCl_3$) δ 7.85 (s, 1H), 7.81 (dd, J=8.2, 1.9 Hz, 1H), 6.74 (d, J=8.2 Hz, 1H), 4.69-4.63 (m, 2H), 3.83 (s, 2H), 3.11-3.05 (m, 2H), 2.58 (q, J=7.1 Hz, 4H), 2.23 (s, 3H), 1.01 (t, J=7.1 Hz, 6H). $^{13}$C NMR (101 MHz, $CDCl_3$) δ 165.53, 146.70, 129.19, 126.03, 122.38, 117.80, 114.90, 51.99, 51.55, 47.52, 17.41, 12.23.

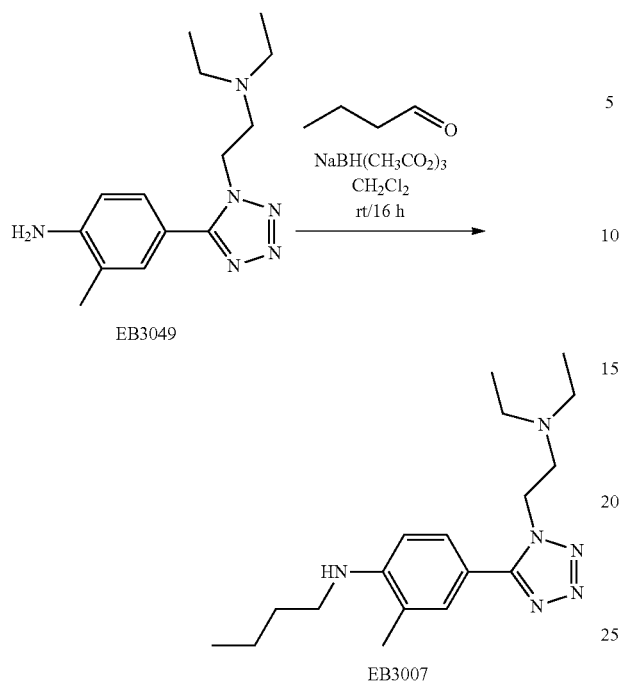

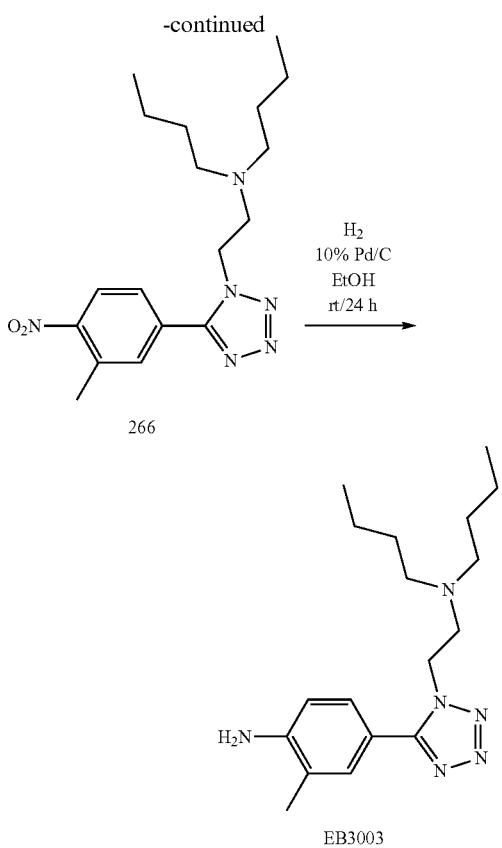

Synthesis of $N^1$-((1-butyl-1,2,3,4-tetrahydroquinolin-6-yl)methyl)-$N^2$,$N^2$-dimethylethane-1,2-diamine, (EB3007). To a solution of 4-(1-(2-(diethylamino)ethyl)-1H-tetrazol-5-yl)-2-methylaniline, EB3049 (117 mg, 0.426 mmols) in 2 ml of anhydrous $CH_2Cl_2$ was added butyraldehyde (36.7 mg, 0.426 mmols), under Ar atmosphere. Sodium tri-acetoxyborohydride (90.4 mg, 0.426 mmols) was added portionwise. The mixture was stirred at room temperature for 16 h, diluted with water and extracted with ethyl acetate (3×20 ml). The organic extracts were combined, washed with water (20 ml), dried over $Na_2SO_4$, filtered and the solvent evaporated under vacuum. The title compound was isolated by flash column chromatography on silica gel using EtOAc:hexanes 1:9 for elution. Yield 62 mg (44%). $^1$H NMR (400 MHz, $CDCl_3$) δ 7.90 (dd, J=8.4, 1.9 Hz, 1H), 7.83 (d, J=1.1 Hz, 1H), 6.67 (d, J=8.4 Hz, 1H), 4.69-4.60 (m, 2H), 3.71 (s, 1H), 3.22 (t, J=7.1 Hz, 2H), 3.13-3.06 (m, 2H), 2.58 (q, J=7.1 Hz, 4H), 2.19 (s, 3H), 1.67 (dd, J=14.7, 7.3 Hz, 2H), 1.47 (dd, J=15.0, 7.4 Hz, 2H), 1.00 (dt, J=10.2, 7.2 Hz, 9H). $^{13}$C NMR (101 MHz, $CDCl_3$) δ 165.75, 148.18, 128.65, 126.29, 121.75, 115.62, 109.40, 51.98, 51.50, 47.52, 43.57, 31.73, 20.48, 17.47, 14.06, 12.23.

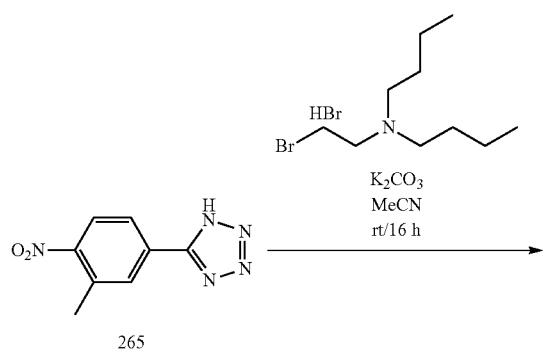

Synthesis of N-butyl-N-(2-(5-(3-methyl-4-nitrophenyl)-1H-tetrazol-1-yl)ethyl)butan-1-amine, (266). 5-(3-methyl-4-nitrophenyl)-1H-tetrazole, 265 (0.9 g, 4.39 mmols) was dissolved in 15 ml of MeCN; N-(2-bromoethyl)-N-butylbutan-1-amine hydrobromide (1.04 g, 4.39 mmols) and $K_2CO_3$ (0.606 g, 3.9 mmols) were added. The mixture was stirred at room temperature for 16 h. The organic solvent was removed under vacuum and the aqueous residue was poured into ice; the precipitate formed was filtered and dried under vacuum to afford the title compound. Yield 935 mg (59%). $^1$H NMR (400 MHz, $CDCl_3$) δ 8.16 (d, J=0.6 Hz, 1H), 8.14-8.03 (m, 2H), 4.71 (t, J=6.6 Hz, 2H), 3.09 (t, J=6.6 Hz, 2H), 2.69 (s, 3H), 2.57-2.35 (m, 4H), 1.34 (ddd, J=8.5, 7.6, 4.0 Hz, 4H), 1.23 (dt, J=15.3, 6.1 Hz, 4H), 0.85 (t, J=7.3 Hz, 6H).

Synthesis of 4-(1-(2-(dibutylamino)ethyl)-1H-tetrazol-5-yl)-2-methylaniline, (EB3003). The title compound was prepared as described for compound EB3005. N-butyl-N-(2-(5-(3-methyl-4-nitrophenyl)-1H-tetrazol-1-yl)ethyl)butan-1-amine, 266 (935 mg, 2.59 mmols) was dissolved in 15 ml of EtOH. 200 mg of 10% Pd/C were used. The title compound was isolated by flash column chromatography on silica gel using EtOAc:Hex 7:3 for elution. Yield 300 mg (35%). $^1$H NMR (400 MHz, $CDCl_3$) δ 7.83 (s, 1H), 7.79 (dd, J=8.2, 1.9 Hz, 1H), 6.71 (d, J=8.2 Hz, 1H), 4.62 (t, J=6.8 Hz, 2H), 3.85 (s, 2H), 3.05 (t, J=6.8 Hz, 2H), 2.46-2.40 (m, 4H), 2.20 (s, 3H), 1.34 (ddd, J=8.6, 7.6, 4.0 Hz, 4H), 1.27-1.18 (m, 4H), 0.85 (t, J=7.3 Hz, 6H). $^{13}$C NMR (101 MHz, $CDCl_3$) δ 165.46, 146.66, 129.15, 125.99, 122.33, 117.80, 114.86, 54.20, 53.19, 51.55, 29.65, 20.53, 17.38, 14.15.

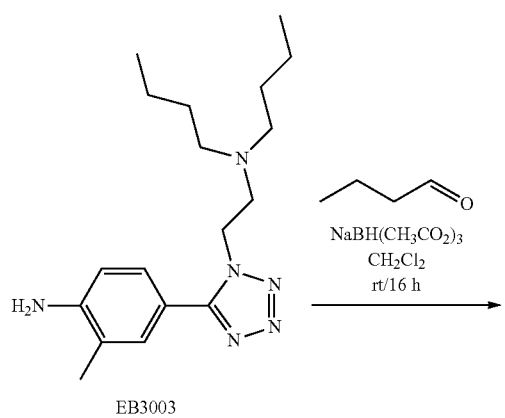

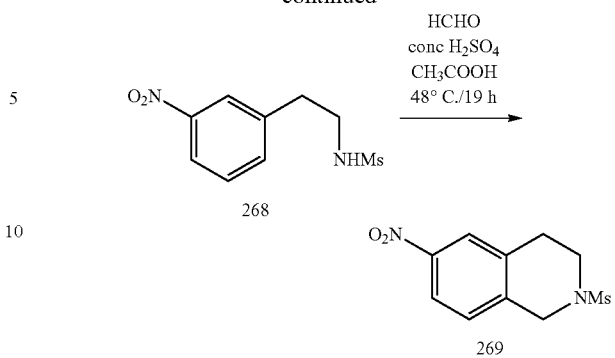

Synthesis of N-butyl-4-(1-(2-(dibutylamino)ethyl)-1H-tetrazol-5-yl)-2-methylaniline (EB3008). The title compound was prepared as described for compound EB3007. 4-(1-(2-(dibutylamino)ethyl)-1H-tetrazol-5-yl)-2-methylaniline, EB3003 (121 mg, 0.366 mmols), butyraldehyde (63 mg, 0.732 mmols), sodium tri-acetoxyborohydride (155 mg, 0.732 mmols), 3 ml of anh $CH_2Cl_2$ were used. The title compound was isolated by flash column chromatography on silica gel using EtOAc:Hexanes 1:9 for elution. Yield 58 mg (36%). $^1$H NMR (400 MHz, $CDCl_3$) δ 7.94 (d, J=1.7 Hz, 1H), 7.88 (dd, J=8.3, 2.0 Hz, 1H), 7.13 (d, J=8.3 Hz, 1H), 4.65 (t, J=6.8 Hz, 2H), 3.07 (t, J=6.8 Hz, 2H), 3.01-2.92 (m, 4H), 2.51-2.40 (m, 4H), 2.34 (s, 3H), 1.46-1.33 (m, 8H), 1.31-1.19 (m, 8H), 0.86 (td, J=7.2, 0.9 Hz, 12H). $^{13}$C NMR (101 MHz, $CDCl_3$) δ 165.27, 152.68, 134.75, 129.62, 124.71, 122.05, 121.68, 54.18, 53.22, 53.14, 51.60, 29.65, 29.44, 20.54, 18.67, 14.13, 14.09.

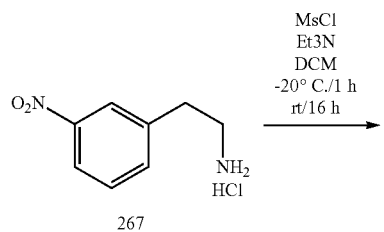

Synthesis of N-(3-nitrophenethyl)methanesulfonamide, (268). In a two neck 500 ml RBF, equipped with an addition funnel, a thermometer and under Ar, 1-(3-nitrophenyl)-2-propanamine hydrochloride, 267 (4.85 g, 23.93 mmols) was dissolved in 250 ml of anhydrous $CH_2Cl_2$ at room temperature. Triethylamine (7.27 g, 71.8 mmols) was added in one portion. The solution was cooled to -20° C. in a dry ice acetone bath. Methanesulfonyl chloride (3.3 g, 28.72 mmols) was dissolved in 10 ml of anhydrous $CH_2Cl_2$; the methanesulfonyl chloride solution was added dropwise to the cooled mixture, keeping the temperature at -10° C. After addition is complete, the mixture was stirred at -2.0° C. for a additional 20 min, then allowed to warm to room temperature and stirred for 16 h. 0.5M HCl (250 ml) was added, the mixture was stirred for 5 min and phases were separated. The organic phase was washed with saturated $NaHCO_3$ (1×250 ml), dried over $Na_2SO_4$, filtered and the solvent evaporated under reduced pressure to give the tide compound. Yield 5.85 g (100%). $^1$H NMR (400 MHz, DMSO) δ 8.18-8.02 (m, 2H), 7.72 (d, J=7.6 Hz, 1H), 7.60 (t, J=7.9 Hz, 1H), 3.24 (t, J=7.1 Hz, 2H), 2.91 (t, J=7.1 Hz, 2H), 2.84 (s, 3H).

Synthesis of 2-(methylsulfonyl)-6-nitro-1,2,3,4-tetrahydroisoquinoline, (269). Glacial acetic acid (16 ml) was cooled to 0° C., concentrated sulfuric acid (24 ml) was added dropwise to the glacial acetic acid at 0° C. The cooled acetic acid:sulfuric mixture was added dropwise to N-(3-nitrophenethyl)methanesulfonamide, 268 (2.5 g, 10.23 mmols). After addition of the acid mixture was completed, paraformaldehyde (0.307 g, 10.23 mmols) was added in one portion. The mixture was stirred at 0° C. for 30 min; then heated at 45° C. for 20 h. The mixture was allowed to cool down to room temperature and then poured into 100 ml of ice-water. The precipitate formed was filtered, washed with cold water (3×100 ml), then air dried. The product obtained was consistent with the title compound and was used as is without further purification. Yield 2 g (76%). $^1$H NMR (400 MHz, $CDCl_3$) δ 8.07 (dd, J=4.2, 1.9 Hz, 2H), 7.28 (s, 1H), 4.55 (s, 2H), 3.61 (dd, J=7.0, 4.9 Hz, 3H), 3.10 (t, J=6.0 Hz, 4H), 2.90 (s, 3H).

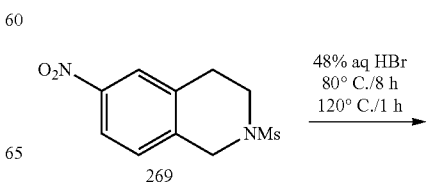

Hz, 1H), 3.75 (s, 2H), 2.99 (t, J=5.8 Hz, 2H), 2.82 (t, J=5.9 Hz, 2H), 2.73 (s, 4H), 2.56 (s, 4H), 1.83-1.75 (m, 4H).

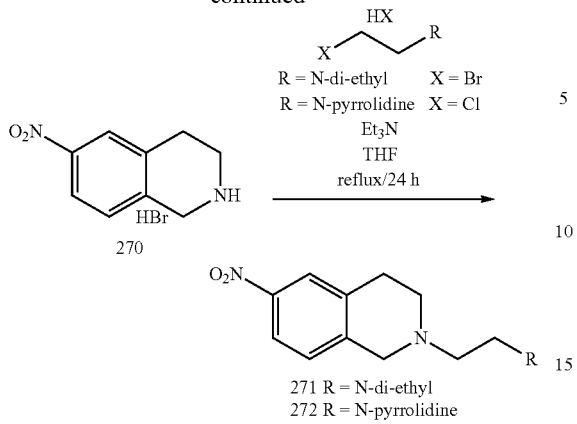

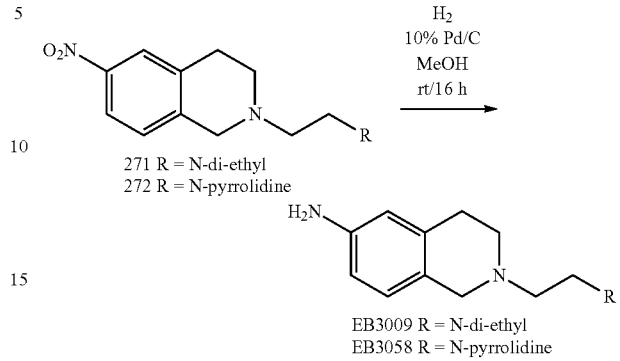

Synthesis of 6-nitro-1,2,3,4-tetrahydroisoquinoline, (270). 2-(methylsulfonyl)-6-nitro-1,2,3,4-tetrahydroisoquinoline, 269 (2 g, 7.8 mmols) was suspended in 15 ml of 48% aqueous HBr. The mixture was heated at 80° C. overnight, then at 120° C. for 2 h. The mixture was allowed to cool down to room temperature and diluted with 50 nil of water. The aqueous mixture was extracted with EtOAc (2×100 ml). The aqueous phase was basified with 6M NaOH and extracted with $CH_2Cl_2$ (3×100 ml). The organic extracts were pooled, dried over $Na_2SO_4$, filtered and the solvent evaporated under vacuum. The crude mixture was purified by flash column chromatography on silica gel using $CH_2Cl_2$:MeOH 9:1 for elution. Yield 650 mg (47%). $^1$H NMR (400 MHz, MeOD) δ 8.24-8.11 (m, 2H), 7.49 (d, J=8.5 Hz, 1H), 4.50 (s, 2H), 3.57 (t, J=6.4 Hz, 2H), 3.25 (t, J=6.4 Hz, 2H).

N,N-diethyl-2-(6-nitro-3,4-dihydroisoquinolin-2(1H)-yl)ethan-1-amine, (271). 6-nitro-1,2,3,4-tetrahydroisoquinoline, 270 (300 mg, 1.68 mmols) and 2-(Diethylamino)ethyl Bromide Hydrobromide (2.24 g, 8.42 mmols) were suspended in 25 ml of THF. Triethylamine (1.7 g, 16.84 mmols) was added in one portion. The mixture was stirred and heated under reflux conditions for 24 h. The solvent was evaporated under vacuum, the residue was dissolved in water (50 ml) and extracted with $CH_2Cl_2$ (3×50 ml). The organic layer was dried over $Na_2SO_4$, filtered, and the solvent removed under reduced pressure. The crude mixture was separated by flash column chromatography on basic alumina using $CH_2Cl_2$, $CH_2Cl_2$:MeOH 98:2 for elution. Yield 250 mg (54%). $^1$H NMR (400 MHz, CDCl$_3$) δ 7.92 (d, J=6.9 Hz, 2H), 7.16 (d, J=9.1 Hz, 1H), 3.80 (s, 2H), 3.14-3.07 (m, 4H), 2.97 (t, J=5.8 Hz, 2H), 2.84 (t, J=5.7 Hz, 2H), 1.37 (dd, J=7.3, 3.9 Hz, 6H).

Synthesis of 6-nitro-2-(2-(pyrrolidin-1-yl)ethyl)-1,2,3,4-tetrahydroisoquinoline, (272). 6-nitro-1,2,3,4-tetrahydroisoquinoline, 270 (700 mg, 3.93 mmols) and 1-(2-chloroethyl)pyrrolidine hydrochloride (1.34 g, 7.86 mmols) were suspended in 25 ml of MeCN. Finely ground $K_2CO_3$ (2.17 g, 15.71 mmols) was added. The mixture was vigorously stirred and heated under reflux conditions for 24 h. The solvent was evaporated under vacuum, the residue was dissolved in water (50 ml) and extracted with EtOAc (3×50 ml). The organic layer was dried over $Na_2SO_4$, filtered, and the solvent removed under reduced pressure. The crude mixture was separated by flash column chromatography on silica on a 50 KPSil SNAP cartridge on a SP1 Biotage® system and using a $CH_2Cl_2$:MeOH gradient from 5% MeOH to 60% MeOH. Yield 157.4 mg (14.5%). $^1$H NMR (400 MHz, Chloroform-d) δ 7.97 (d, J=9.5 Hz, 2H), 7.16 (d, J=8.2

Synthesis of 2-(2-(diethylamino)ethyl)-1,2,3,4-tetrahydroisoquinolin-6-amine, (EB3009). The title compound was prepared as described for compound EB3005. N,N-diethyl-2-(6-nitro-3,4-dihydroisoquinolin-2(1H)-yl)ethanamine, 271 (250 mg, 0.901 mmols) was dissolved in 40 ml of EtOH. 144 mg of 10% Pd/C (144 mg) were used. Yield 205 mg (93%). $^1$H NMR (400 MHz, CDCl$_3$) δ 6.80 (d, J=8.1 Hz, 1H), 6.51-6.45 (m, 1H), 6.43 (d, J=2.2 Hz, 1H), 3.55 (s, 2H), 3.50 (s, 2H), 2.81 (t, J=5.6 Hz, 2H), 2.74-2.66 (m, 4H), 2.64-2.55 (m, 6H), 1.05 (t, J=7.1 Hz, 6H). $^{13}$C NMR (101 MHz, CDCl$_3$) δ 144.59, 135.23, 127.53, 125.24, 114.95, 113.42, 56.64, 56.35, 51.73, 50.87, 47.67, 29.29, 11.93.

Synthesis of 2-(2-(pyrrolidin-1-yl)ethyl)-1,2,3,4-tetrahydroisoquinolin-6-amine, (EB3058) The title compound was prepared as described above for compound EB3005. 6-nitro-2-(2-(pyrrolidin-1-yl)ethyl)-1,2,3,4-tetrahydroisoquinoline, 272 (150 mg, 0.545 mmols) was dissolved in 15 ml of EtOH. 87 mg of 10% Pd/C were used. Yield 133 mg (99%) was consistent with the title compound and was used as is without further purification. $^1$H NMR (400 MHz, Chloroform-d) δ 6.80 (d, J=8.1 Hz, 1H), 6.47 (d, J=8.2 Hz, 1H), 6.43 (s, 1H), 3.56 (s, 2H), 3.47 (s, 3H), 2.81 (t, J=5.8 Hz, 2H), 2.76-2.65 (m, 6H), 2.56 (s, 4H), 1.78 (s, 4H).

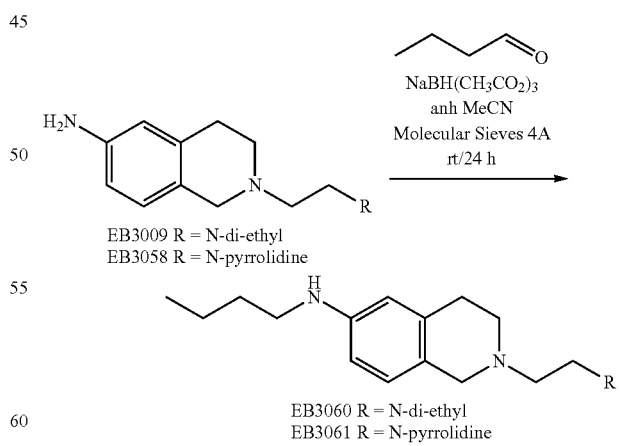

Synthesis of N-butyl-2-(2-(diethylamino)ethyl)-1,2,3,4-tetrahydroisoquinolin-6-amine, (EB3060). Under Ar, butyraldehyde (29 mg, 0.404 mmols) was dissolved in 5 ml of anhydrous MeCN followed by the addition of 2-(2-(diethylamino)ethyl)-1,2,3,4-tetrahydroisoquinolin-6-amine, EB3009 (100 mg, 0.404 mmols), 60 mg of 4 Å molecular sieves and sodium triacetoxyborohydride (86 mg, 0.404 mmols) were added. The mixture was stirred for 10 min Acetic acid (24.3 mg, 0.404 mmols) was added in one portion, then the mixture stirred at room temperature for 24 h. The mixture was filtered, the solid was washed with MeCN (10 ml) and the filtrate evaporated under vacuum. The residue was dissolved in EtOAc (20 ml) and partitionated with water (20 ml). The organic layer was washed with 1N HCl (3×20 ml), the combined aqueous layers were basified with NaOH and extracted with $CH_2Cl_2$ (3×20 ml). The combined organic layers were washed with brine (15 ml), dried over $Na_2SO_4$, filtered and the solvent evaporated under vacuum. The crude mixture was separated by flash column on basic alumina using a $CH_2Cl_2$:EtOH gradient from 1% EtOH to 5% EtOH for elution. The isolated fraction containing the title compound was further separated by reversed phase on a 50G C18 SNAP cartridge on a SP1 Biotage® system and using a MeOH:water gradient from 5% MeOH to 100% MeOH. Yield 44 mg (36%). $^1$H NMR (400 MHz, Chloroform-d) δ 6.81 (d, J=8.2 Hz, 1H), 6.41 (dd, J=8.2, 2.3 Hz, 1H), 6.34 (d, J=2.1 Hz, 1H), 3.55 (s, 2H), 3.07 (t, J=7.1 Hz, 2H), 2.82 (t, J=5.8 Hz, 2H), 2.75-2.65 (m, 4H), 2.64-2.54 (m, 6H), 1.58 (dt, J=14.7, 7.1 Hz, 2H), 1.45-1.36 (m, 4H), 1.05 (t, J=7.1 Hz, 6H), 0.94 (t, J=7.3 Hz, 3H). $^{13}$C NMR (101 MHz, CDCl$_3$) δ 147.07, 135.07, 127.40, 123.79, 112.30, 111.43, 56.67, 56.34, 51.85, 51.01, 50.89, 47.68, 44.12, 31.86, 29.49, 28.58, 20.45, 14.08, 11.96.

Synthesis of N-butyl-2-(2-(pyrrolidin-1-yl)ethyl)-1,2,3,4-tetrahydroisoquinolin-6-amine, (EB3061). The title compound was prepared as described above for compound EB3060. Butyraldehyde (35 mg, 0.485 mmols) was dissolved in 6 ml of anhydrous MeCN, 2-(2-(pyrrolidin-1-yl)ethyl)-1,2,3,4-tetrahydroisoquinolin-6-amine, EB3058 (120 mg, 0.485 mmols), 60 mg of 4 Å molecular sieves, sodium triacetoxyborohydride (102 mg, 0.485 mmols), and acetic acid (29 mg, 0.485 mmols) were added. The crude mixture was separated by flash column chromtography on basic alumina using a $CH_2Cl_2$:EtOH gradient from 1% EtOH to 5% EtOH for elution. Yield 44 mg (30%). $^1$H NMR (400 MHz, Chloroform-d) δ 6.81 (d, J=8.2 Hz, 1H), 6.41 (d, J=8.3 Hz, 1H), 6.34 (s, 1H), 3.56 (s, 2H), 3.49 (s, 2H), 3.42 (s, 1H), 3.07 (s, 2H), 2.81 (d, J=5.4 Hz, 2H), 2.76-2.64 (m, 6H), 2.55 (s, 4H), 1.78 (s, 4H), 1.58-1.53 (m, 2H), 1.41 (q, J=7.3 Hz, 2H), 0.94 (t, J=7.2 Hz, 3H).

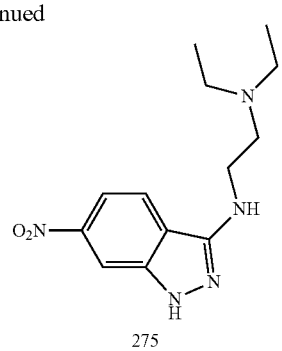

Synthesis of 6-nitro-1H-indazol-3-amine, (274). To a solution of 2-fluoro-4-nitrobenzonitrile, 273 (5 g, 30.1 mmols) in ethanol (50 ml) was added hydrazine hydrate (15 ml). The resulting solution was heated at 80° C. for 12 h. The reaction mixture was poured into water. The solid formed, consistent with the title compound was filtered and dried. Yield 2.1 g (39 qv). $^1$H NMR (400 MHz, DMSO) δ 8.13 (d, J=1.9 Hz, 1H), 7.91 (d, J=8.8 Hz, 1H), 7.72 (dd, J=8.8, 2.0 Hz, 1H).

Synthesis of $N^1,N^1$-diethyl-$N^2$-(6-nitro-1H-indazol-3-yl)ethane-1,2-diamine, (275). To a solution of 6-nitro-1H-indazol-3-amine, 274 (1 g, 5.61 mmols), 2-(diethylamino)ethyl bromide hydrobromide (1.47 g, 5.61 mmols) in NMP (6 ml) was added $K_2CO_3$ (1.55 g, 11.23 mmols). The mixture was heated in a sealed tube at 100° C. for 2 h. The mixture was allowed to cool down to room temperature and then poured into ice. The mixture was extracted with ethyl acetate (3×30 ml). The organic layers were combined, washed with water (100 ml), dried over $Na_2SO_4$, filtered and the solvent evaporated under vacuum. The title compound was isolated by flash column chromatography on silica gel using $CH_2Cl_2$:MeOH for elution. Yield 450 mg (29%). $^1$H NMR (400 MHz, CDCl$_3$) δ 8.41-8.23 (m, 1H), 7.48 (t, J=1.4 Hz, 3H), 4.38-4.26 (m, 3H), 2.87-2.81 (m, 2H), 2.49-2.41 (m, 4H), 0.86 (t, J=7.2 Hz, 6H).

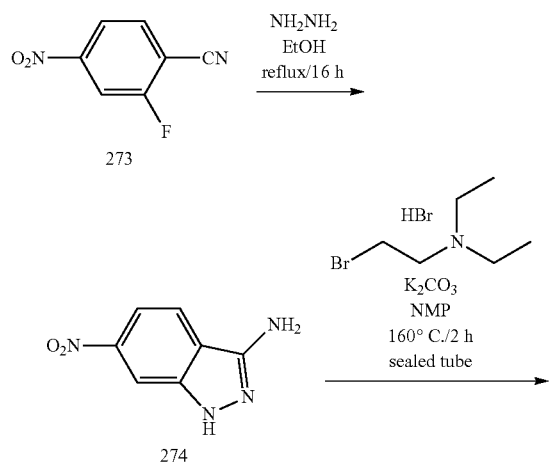

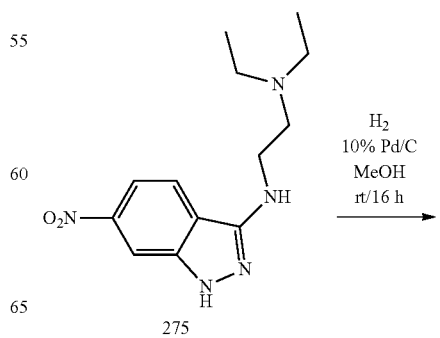

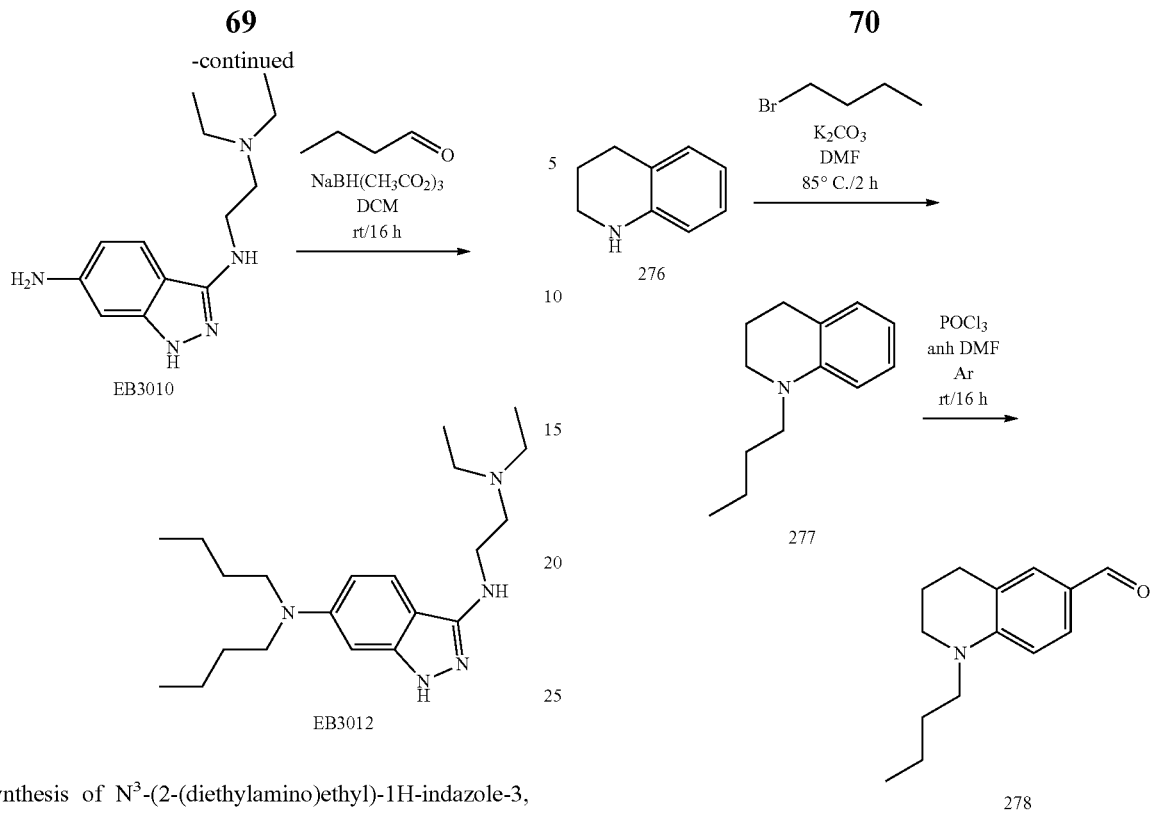

Synthesis of N³-(2-(diethylamino)ethyl)-1H-indazole-3,6-diamine, (EB3010). The title compound was prepared as described above for compound EB3005. N¹,N¹-diethyl-N²-(6-nitro-1H-indazol-3-yl)ethane-1,2-diamine, 275 (500 mg, 1.8 mmols) is dissolved in 10 ml of methanol, 100 mg of 10% Pd/C were used. The crude mixture was separated by flash column chromatography on a 25G KPSil SNAP cartridge on a SP1 Biotage® system using a CH$_2$Cl$_2$:MeOH gradient from 10% MeOH to 100% MeOH. Yield 290 mg (65%). $^1$H NMR (400 MHz, CDCl$_3$) δ 7.20 (dd, J=8.8, 0.6 Hz, 1H), 6.54 (dd, J=1.8, 0.6 Hz, 1H), 6.33 (dd, J=8.8, 1.9 Hz, 1H), 5.28 (s, 2H), 4.28-4.22 (m, 2H), 3.60 (s, 2H), 2.85-2.81 (m, 2H), 2.52 (q, J=7.1 Hz, 4H), 0.94 (t, J=7.1 Hz, 6H). $^{13}$C NMR (101 MHz, CDCl$_3$) δ 149.02, 145.31, 140.14, 120.18, 112.09, 105.46, 96.26, 54.99, 49.13, 47.96, 11.78.

Synthesis of N⁶,N⁶-dibutyl-N³-(2-(diethylamino)ethyl)-1H-indazole-3,6-diamine, (EB3012). The title compound was prepared as described above for compound EB3007. N³-(2-(diethylamino)ethyl)-1H-indazole-3,6-diamine, EB3010 (128 mg, 0.517 mmols), butyraldehyde (44.6 mg, 0.517 mmols), sodium triacetoxyborohydride (221.5 mg, 1.04 mmols), in 5 ml of CH$_2$Cl$_2$. The crude mixture was separated by flash column chromatography on a 25G KPSil SNAP cartridge on a SP1 Biotage® system using a CH$_2$Cl$_2$:MeOH gradient from 0% MeOH to 50% MeOH. Yield 13 mg (7%). $^1$H NMR (400 MHz, CDCl$_3$) δ 7.24 (d, J=9.4 Hz, 1H), 6.54 (dd, J=9.2, 2.1 Hz, 1H), 6.40 (d, J=1.9 Hz, 1H), 4.40-4.35 (m, 2H), 3.30-3.25 (m, 4H), 3.02-2.98 (m, 2H), 2.64 (t, J=7.0 Hz, 4H), 2.03 (s, 1H), 1.61-1.55 (m, 4H), 1.37-1.31 (m, 4H), 1.04 (t, J=7.2 Hz, 6H), 0.94 (d, J=7.3 Hz, 6H). $^{13}$C NMR (101 MHz, CDCl$_3$) δ 149.74, 148.24, 140.51, 119.74, 110.57, 103.58, 92.58, 54.09, 51.48, 47.72, 47.66, 29.70, 20.54, 14.17, 11.08.

Synthesis of 1-butyl-1,2,3,4-tetrahydroquinoline, (277). To a solution of 1,2,3,4-Tetrahydroquinoline, 276 (15 g, 112.6 mmols) and bromo butane (18.52 g, 135.14 mmols) in 150 ml of DMF, potassium carbonate (18.86 g, 135.14 mmols) was added in one portion. The mixture was heated at 85° C. for 2 h. The mixture was allowed to cool down to room temperature and diluted with 500 ml of water. The reaction mixture was extracted with EtOAc (3×500 ml). The combined organic layers were washed with water (1000 ml) and brine (1000 ml), dried over Na$_2$SO$_4$, filtered and the solvent evaporated under vacuum. The title compound was obtained by trituration of the crude mixture with hexanes. Yield 14.5 g (68%). $^1$H NMR (400 MHz, Chloroform-d) δ 7.04 (t, J=7.8 Hz, 1H), 6.94 (d, J=6.8 Hz, 1H), 6.64-6.52 (m, 2H), 3.30-3.20 (m, 4H), 2.75 (t, J=6.4 Hz, 2H), 1.95 (p, J=6.2 Hz, 2H), 1.58 (p, J=7.6 Hz, 2H), 1.37 (dq, J=14.6, 7.3 Hz, 2H), 0.95 (t, J=7.3 Hz, 3H).

Synthesis of 1-butyl-1,2,3,4-tetrahydroquinoline-6-carbaldehyde, (278). 1-butyl-1,2,3,4-tetrahydroquinoline, 277 (15 g, 79.24 mmols) was dissolved in 12 ml of anhydrous DMF tinder Ar. The solution was cooled to 0° C. POCl$_3$ (14.58 g, 95.1 mmols) was added dropwise. After addition of POCl$_3$ was completed, the mixture was allowed to warm to room temperature and stirred overnight. The reaction mixture was poured into ice, then extracted with Et$_2$O (3×100 ml). The combined organic layers were dried over Na$_2$SO$_4$ filtered and the solvent evaporated under vacuum. The title compound was isolated by flash column chromatography on silica gel using a EtOAc:Hexanes gradient from 0% to 20% EtOAc. Yield 17.1 g (99%). $^1$H NMR (400 MHz, CDCl$_3$) δ 9.65 (s, 1H), 7.53 (dd, J=8.6, 2.0 Hz, 1H), 7.45 (d, J=0.8 Hz, 1H), 6.58 (d, J=8.6 Hz, 1H), 3.45-3.27 (m, 4H), 2.78 (t, J=6.3 Hz, 2H), 1.95 (td, J=11.5, 6.0 Hz, 2H), 1.70-1.54 (m, 2H), 1.38 (dd, J=15.1, 7.5 Hz, 2H), 0.97 (t, J=7.3 Hz, 3H).

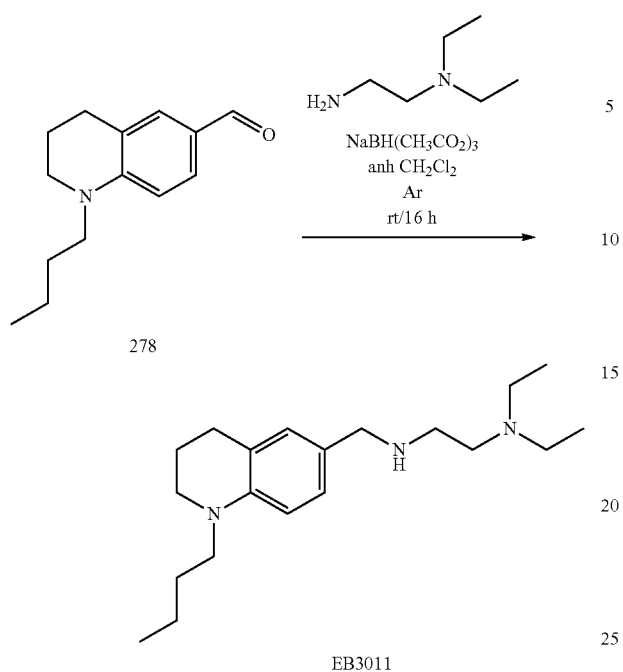

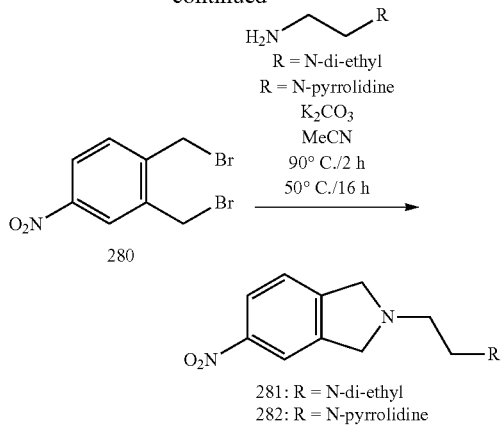

Synthesis of N¹-((1-butyl-1,2,3,4-tetrahydroquinolin-6-yl)methyl)-N²,N²-diethylethane-1,2-diamine, (EB3011). To a solution of 1-butyl-1,2,3,4-tetrahydroquinoline-6-carbaldehyde 278 (850 mg, 3.91 mmols) and N¹,N¹-diethylethane-1,2-diamine (454 mg, 3.91 mmols) in 10 ml of anhydrous CH$_2$Cl$_2$ under Ar atmosphere was added sodium tri-acetoxy-borohydride (1.66 g, 7.82 mmols) portion wise. The mixture was stirred at room temperature for 16 h, diluted with water and extracted with EtOAc (3×20 ml). The combined organic layers were washed with water (100 ml), dried over Na$_2$SO$_4$, filtered and the solvent evaporated under vacuum. The title compound was isolated by flash column chromatography on silica gel basified with 5 ml of triethyl amine and EtOAc: Hexanes 1:9 for elution. Yield 42 mg (3.4%). ¹H NMR (400 MHz, CDCl$_3$) δ 6.96 (dd, J=8.3, 2.1 Hz, 1H), 6.89 (d, J=1.8 Hz, 1H), 6.51 (d, J=8.3 Hz, 1H), 3.63 (s, 2H), 3.27-3.19 (m, 4H), 2.71 (dt, J=18.9, 6.2 Hz, 4H), 2.57-2.47 (m, 6H), 1.95-1.90 (m, 2H), 1.60-1.52 (m, 2H), 1.35 (dd, J=15.0, 7.5 Hz, 2H), 0.97 (dt, J=20.3, 7.2 Hz, 9H). ¹³C NMR (101 MHz, CDCl$_3$) δ 144.49, 129.36, 127.14, 127.08, 122.26, 110.48, 53.79, 52.80, 51.43, 49.57, 47.14, 47.05, 28.47, 28.31, 22.45, 20.59, 14.17, 11.93.

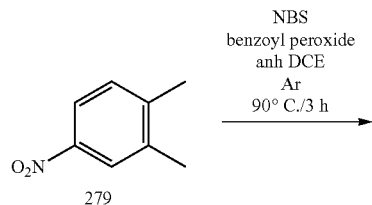

Synthesis of 1,2-bis(bromomethyl)-4-nitrobenzene, (280). 1,2-dimethyl-4-nitrobenzene, 279 (25 g, 165 mmol) was dissolved in 300 ml of anhydrous DCE. Ar was bubbled through the mixture for 15 min. N-bromosuccinimide (58.7 g, 330.76 mmol) was added and the mixture stirred for 5 min. Benzoyl peroxide (625 mg) was added in one portion. The mixture was heated to 90° C. for 3 h, then cooled to room temperature. The mixture was washed with H$_2$O (4×250 ml). The organic phase was dried over Na$_2$SO$_4$, filtered, and the solvent evaporated under vacuum. The title compound was isolated by flash column chromatography on silica gel on a KPSil SNAP cartridge on a SP1 Biotage® system and using a EtOAc:Hex gradient from 2% EtOAc to 20% EtOAc. Yield 14.7 g (29%). ¹H NMR (400 MHz, DMSO-d$_6$) δ 8.40 (s, 1H), 8.20 (d, J=8.5 Hz, 1H), 7.78 (d, J=8.6 Hz, 1H), 4.93 (d, J=17.0 Hz, 4H).

Synthesis of N,N-diethyl-2-(5-nitroisoindolin-2-yl)ethan-1-amine, (281). 1,2-bis(bromomethyl)-4-nitrobenzene, 280 (1.5 g, 4.86 mmols) and N¹,N¹-diethylethane-1,2-diamine (0.57 g, 4.86 mmols) were suspended in 50 ml of MeCN. Finely ground K$_2$CO$_3$ (1.48 g, 10.68 mmols) was added. The mixture was vigorously stirred and heated under reflux conditions for 2 h, then at 50° C. overnight. The mixture was allowed to cool down to room temperature, then diluted with water (200 ml). The mixture was extracted with EtOAc (3×250 ml). The combined organic layers were washed with water (250 ml), brine (250 ml), dried over Na$_2$SO$_4$, filtered, and the solvent removed under reduced pressure. The crude mixture was separated by flash column chromatography on silica on a 50G KPSil SNAP cartridge on a SP1 Biotage® system and using a CH$_2$Cl$_2$:MeOH gradient from 2% MeOH to 40% MeOH. Yield 723 mg (57%) ¹H NMR (400 MHz, Chloroform-d) δ 8.10 (dd, J=8.2, 2.1 Hz, 1H), 8.05 (d, J=1.9 Hz, 1H), 7.33 (d, J=8.2 Hz, 1H), 4.05 (s, 4H), 2.99 (t, J=7.0 Hz, 2H), 2.76 (dt, J=14.0, 7.0 Hz, 6H), 1.14 (t, J=7.2 Hz, 6H).

Synthesis of 5-nitro-2-(2-(pyrrolidin-1-yl)ethyl)isoindoline, (282). 1,2-bis(bromomethyl)-4-nitrobenzene, 280 (500 mg, 1.62 mmols) and 2-(pyrrolidin-1-yl)ethan-1-amine (188 mg, 1.62 mmols) were suspended in 10 ml of MeCN. Finely ground K$_2$CO$_3$ (447 mg, 3.24 mmols) was added. The mixture was vigorously stirred and heated under reflux conditions for 2 h. The solvent was evaporated under vacuum, the residue was dissolved in water (20 ml) and extracted with EtOAc (3×50 ml). The organic layers were combined; washed with water (50 ml), brine (50 ml), dried over Na$_2$SO$_4$, filtered, and the solvent removed under reduced pressure. The crude mixture was separated by flash column chromatography on silica on a 25 KPSil SNAP cartridge on a SP1 Biotage® system and using a $CH_2Cl_2$:MeOH gradient from 7% MeOH to 60% MeOH. Yield 105.4 mg (25%). $^1$H NMR (400 MHz, Chloroform-d) δ 8.10 (d, J=8.2 Hz, 1H), 8.05 (s, 1H), 7.32 (d, J=8.2 Hz, 1H), 4.05 (s, 4H), 2.98 (t, J=7.0 Hz, 2H), 2.75 (t, J=7.0 Hz, 2H), 2.66 (s, 4H), 1.84 (s, 4H)

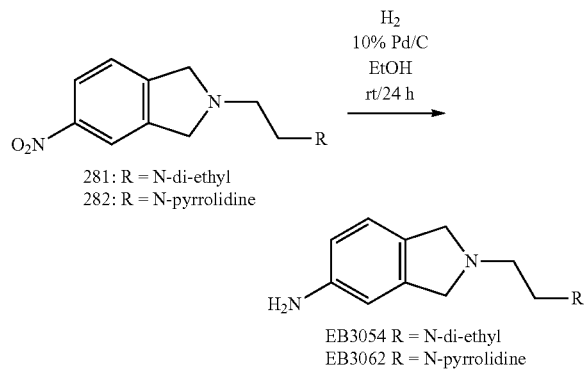

Synthesis of 2-(2-(diethylamino)ethyl)isoindolin-5-amine, (EB3054). The title compound was prepared as described above for compound EB3005. N,N-diethyl-2-(5-nitroisoindolin-2-yl)ethan-1-amine, 281 (80 mg, 0.304 mmols) was dissolved in 15 ml of EtOH. 48.5 mg of 10% Pd/C were used. Yield 57 mg (81%) was consistent with the target product and was used as is without further purification. $^1$H NMR (400 MHz, CDCl$_3$) δ 6.91 (d, J=8.5 Hz, 1H), 6.57-6.43 (m, 2H), 4.74 (s, 2H), 3.86 (d, J=5.2 Hz, 4H), 2.94 (dd, J=8.1, 6.1 Hz, 2H), 2.76 (ddd, J=19.5, 11.0, 6.4 Hz, 6H), 1.12 (t, J=7.2 Hz, 6H). $^{13}$C NMR (101 MHz, CDCl$_3$) δ 145.69, 140.82, 129.44, 122.82, 113.93, 109.14, 59.51, 58.91, 53.22, 51.18, 47.39, 10.90.

Synthesis of 2-(2-(pyrrolidin-1-yl)ethyl)isoindolin-5-amine (EB3062). 5-nitro-2-(2-(pyrrolidin-1-yl)ethyl)isoindoline, 282 (100 mg, 3.82 mmols) was dissolved in 20 ml of EtOH. 61 mg of 10% Pd/C are used. Yield 80 mg (91%). $^1$H NMR (400 MHz, Chloroform-d) δ 6.98 (d, J=7.8 Hz, 1H), 6.55 (dd, J=10.3, 2.5 Hz, 2H), 3.90 (d, J=6.2 Hz, 4H), 3.50 (s, 2H), 2.94 (dd, J=8.8, 6.1 Hz, 2H), 2.75 (dd, J=8.8, 6.1 Hz, 2H), 2.65 (s, 4H), 1.88-1.78 (m, 4H). $^{13}$C NMR (101 MHz, CDCl$_3$) δ 145.49, 141.41, 130.25, 122.92, 113.94, 109.34, 59.69, 59.07, 55.49, 55.36, 54.72, 23.57.

Synthesis of N-butyl-2-(2-(diethylamino)ethyl)isoindolin-5-amine, EB3059. The title compound was prepared as described above for compound EB3060. Butyraldehyde (188 mg, 2.6 mmols) was dissolved in 40 ml of anhydrous MeCN followed by the addition of 2-(2-(diethylamino)ethyl)isoindolin-5-amine, EB3054 (607 mg, 2.6 mmols), 360 mg of 4 Å molecular sieves, sodium tri-acetoxyborohydride (552 mg, 2.6 mmols) and acetic acid (156 mg, 2.6 mmols). The crude mixture was separated by flash column on a 50G KPSil SNAP cartridge on a SP1 Biotage® system and using $CH_2Cl_2$:MeOH gradient from 2% MeOH to 60% MeOH for elution. Yield 263 mg (35%). $^1$H NMR (400 MHz, Chloroform-d) δ 6.97 (d, J=7.9 Hz, 1H), 6.45 (d, J=8.4 Hz, 2H), 3.87 (d, J=10.4 Hz, 4H), 3.08 (t, J=7.1 Hz, 2H), 2.84 (dd, J=8.9, 6.1 Hz, 2H), 2.68 (dd, J=9.0, 6.1 Hz, 2H), 2.61 (q, J=7.1 Hz, 4H), 1.59 (dt, J=14.6, 7.2 Hz, 2H), 1.47-1.36 (m, 2H), 1.07 (t, J=7.1 Hz, 6H), 0.95 (t, J=7.3 Hz, 3H). $^{13}$C NMR (101 MHz, CDCl$_3$) δ 148.00, 141.27, 128.71, 122.83, 111.88, 106.71, 59.91, 59.12, 54.42, 51.96, 47.62, 44.26, 31.81, 20.45, 14.06, 11.78.

N-butyl-2-(2-(pyrrolidin-1-yl)ethyl)isoindolin-5-amine, (EB3064). The title compound was prepared as described above for compound EB3060. Butyraldehyde (156 mg, 2.16 mmols) was dissolved in 30 ml of anhydrous MeCN followed by the addition of 2-(2-(pyrrolidin-1-yl)ethyl)isoindolin-5-amine, EB3062 (500 mg, 2.16 mmols), 300 mg of 4 Å molecular sieves, sodium tri-acetoxyborohydride (458 mg, 2.16 mmols) and acetic acid (130 mg, 2.16 mmols). The crude mixture was separated by flash column on a 50G KPSil SNAP cartridge on a SP1 Biotage® system and using a $CH_2Cl_2$:MeOH gradient from 7% MeOH to 60% MeOH for elution. Yield 267 mg (43%). $^1$H NMR (400 MHz, Chloroform-d) δ 6.97 (d, J=7.9 Hz, 1H), 6.44 (d, J=9.2 Hz, 2H), 3.87 (d, J=10.1 Hz, 4H), 3.48 (s, 1H), 3.08 (t, J=7.1 Hz, 2H), 2.88 (dd, J=9.1, 6.0 Hz, 2H), 2.69 (dd, J=9.1, 6.0 Hz, 2H), 2.57 (s, 4H), 1.79 (t, J=3.2 Hz, 4H), 1.59 (p, J=7.2 Hz, 2H), 1.42 (dt, J=14.7, 7.3 Hz, 2H), 0.95 (t, J=7.3 Hz, 3H). $^{13}$C NMR (101 MHz, CDCl$_3$) δ 147.98, 141.39, 128.86, 122.83, 111.84, 106.73, 59.92, 59.13, 55.72, 55.69, 54.77, 44.28, 31.82, 23.59, 20.46, 14.07.

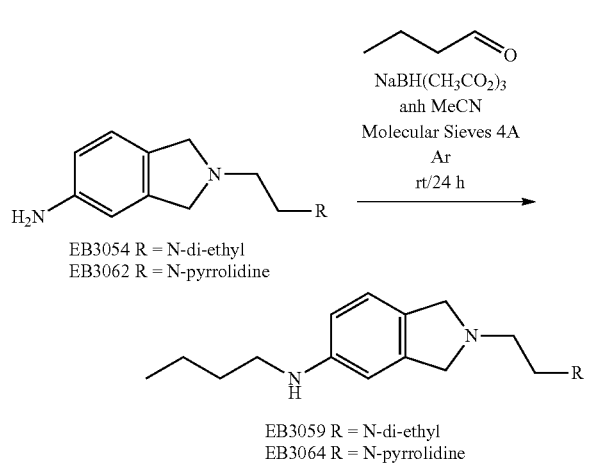

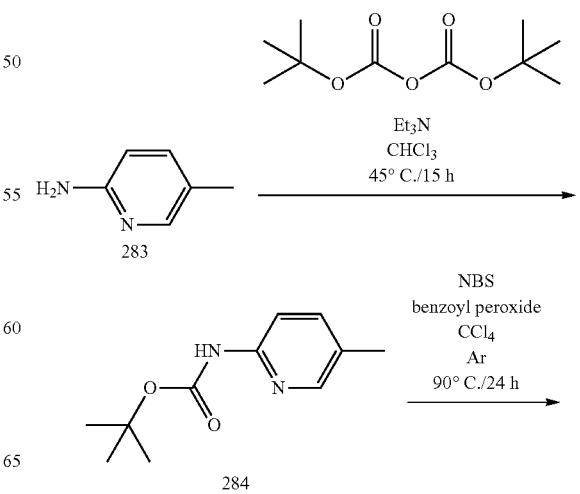

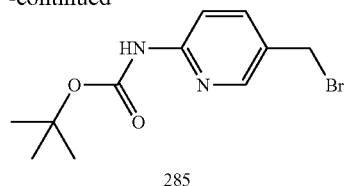

285

Synthesis of tert-butyl (5-methylpyridin-2-yl)carbamate, (284). 5-methylpyridin-2-amine, 283 (4.98 g, 46 mmols) was dissolved in 135 ml of CH$_2$Cl$_2$. Triethyamine (5.59 g, 55.26 mmols) was added in one portion. Boc$_2$O (12.1 g, 55.26 mmols) was added in one portion. The mixture was heated and stirred at 45° C. under Ar for 16 h. The mixture was allowed to cool down to room temperature, then 200 ml of water were added and the mixture stirred for 15 min Phases were separated, the organic phase was washed with saturated NaHCO$_3$ (2×200 ml), dried over Na$_2$SO$_4$, filtered and the solvent evaporated under vacuum. The crude mixture was separated by flash column chromatography on SiO$_2$ using EtOAc:Hexanes 1:1 for elution. Yield 3.31 g (35%). $^1$H NMR (400 MHz, CDCl$_3$) δ 8.06 (dd, J=1.6, 0.7 Hz, 1H), 7.82 (d, J=8.5 Hz, 1H), 7.47 (dd, J=8.5, 2.4 Hz, 2H), 2.26 (s, 3H), 1.53 (d, J=0.8 Hz, 9H).

Synthesis of tert-butyl (5-(bromomethyl)pyridin-2-yl)carbamate, (285). tert-butyl (5-methylpyridin-2-yl)carbamate, 284 (5 g, 26 mmols) was dissolved in 150 ml of anhydrous CCl$_4$. The solution was flushed with Ar for 15 min N-bromosuccinimide (5.09 g, 28.61 mmols) was added in one portion followed by the addition of 250 mg of benzoyl peroxide. The mixture was heated under reflux for 24 h, then allowed to cool down to room temperature. The precipitate formed was filtered. The filtrate was evaporated under vacuum and the residue dissolved in 150 ml of CH$_2$Cl$_2$. The mixture was washed with brine (2×150 ml), dried over anhydrous Na$_2$SO$_4$, filtered and the solvent evaporated under vacuum. The crude mixture was separated by flash column chromatography on silica gel using CH$_2$Cl$_2$:EtOAc 95:5 for elution, Yield 1.144 g, (16%). NMR (400 MHz, CDCl$_3$) δ 8.28 (d, J=2.2 Hz, 1H), 7.97 (d, J=8.7 Hz, 1H), 7.72 (dd, J=8.7, 2.4 Hz, 1H), 7.59 (s, 1H), 4.47 (s, 2H), 1.56 (s, 9H).

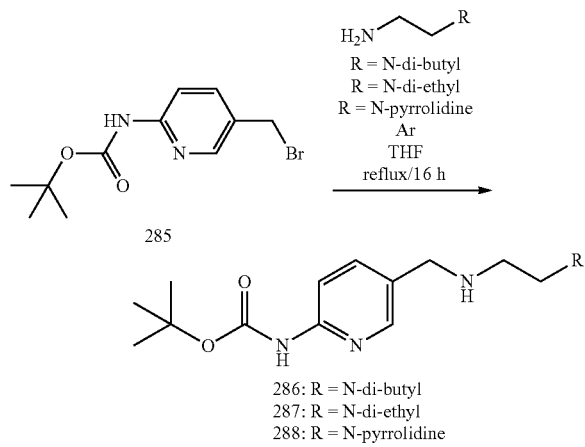

286: R = N-di-butyl
287: R = N-di-ethyl
288: R = N-pyrrolidine

Synthesis of tert-butyl (5-(((2-(dibutylamino)ethyl)amino)methyl)pyridin-2-yl)carbamate, (286). tert-butyl (5-(bromomethyl)pyridin-2-yl)carbamate, 285 (305 mg, 1.06 mmols) was dissolved in 15 ml of THF under Ar. N,N-dibutylethylenediamine (915 mg, 5.31 mmols) was added in one portion. The mixture was refluxed overnight, then the solvent evaporated under vacuum. The crude mixture was separated by flash column chromatography on basic alumina using CH$_2$Cl$_2$:MeOH 98:2 for elution. Yield 289 mg (72%). $^1$H NMR (400 MHz, Chloroform-d) δ 8.19 (s, 1H), 7.91 (d, J=8.5 Hz, 1H), 7.66 (dd, J=8.5, 2.1 Hz, 1H), 7.34 (s, 1H), 3.75 (s, 2H), 2.65 (t, J=5.8 Hz, 2H), 2.56 (t, J=5.7 Hz, 2H), 2.42-2.35 (m, 4H), 1.55 (s, 9H), 1.41 (td, J=14.2, 7.3 Hz, 4H), 1.29 (dq, J=14.4, 7.2 Hz, 4H), 0.91 (t, J=7.2 Hz, 6H).

Synthesis of tert-butyl (5-(((2-(diethylamino)ethyl)amino)methyl)pyridin-2-yl)carbamate. tert-butyl (5-(bromomethyl)pyridin-2-yl)carbamate, 285 (500 mg, 1.74 mmols) was dissolved in 45 ml of THF under Ar. N,N-diethylethylenediamine (1.01 g, 8.71 mmols) was added in one portion. The mixture was refluxed overnight, then the solvent evaporated under vacuum. The crude mixture was separated by flash column chromatography on basic alumina using CH$_2$Cl$_2$:MeOH 95:5 for elution. Yield 489 mg (87%). $^1$H NMR (400 MHz, Chloroform-d) δ 8.19 (d, J=1.8 Hz, 1H), 7.91 (d, J=8.6 Hz, 1H), 7.67 (dd, J=8.5, 2.2 Hz, 1H), 7.43 (s, 1H), 3.77 (s, 2H), 2.67 (t, J=5.9 Hz, 2H), 2.57 (t, J=5.8 Hz, 2H), 2.52 (q, J=7.1 Hz, 4H), 1.55 (s, 9H), 1.01 (t, J=7.1 Hz, 6H).

Synthesis of tert-butyl (5-(((2-(pyrrolidin-1-yl)ethyl)amino)methyl)pyridin-2-yl)carbamate, (288). tert-butyl (5-(bromomethyl)pyridin-2-yl)carbamate, 285 (500 mg, 1.74 mmols) was dissolved in 40 ml of THF under Ar atmosphere. 2-(pyrrolidin-1-yl)ethan-1-amine (994 mg, 8.71 mmols) was added in one portion. The mixture was refluxed overnight, then the solvent evaporated under vacuum. The crude mixture was separated by flash column chromatography on basic alumina using a CH$_2$Cl$_2$:MeOH gradient from 1% MeOH to 2% MeOH. Yield 229 mg (41%). $^1$H NMR (400 MHz, Chloroform-d) δ 8.17 (s, 1H), 7.88 (d, J=8.5 Hz, 1H), 7.68-7.62 (m, 1H), 7.34 (s, 1H), 3.75 (s, 2H), 2.71 (t, J=6.2 Hz, 2H), 2.60 (t, J=6.0 Hz, 2H), 2.47 (s, 4H), 1.76 (dt, H=6.7, 3.6 Hz, 4H), 1.52 (s, 9H).

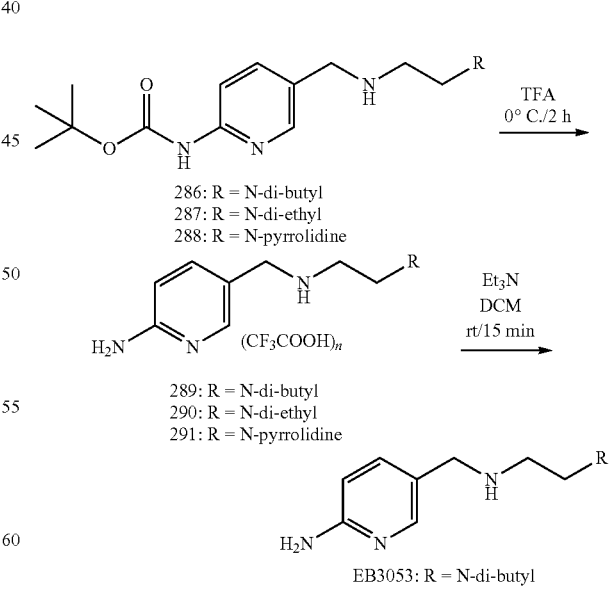

286: R = N-di-butyl
287: R = N-di-ethyl
288: R = N-pyrrolidine

289: R = N-di-butyl
290: R = N-di-ethyl
291: R = N-pyrrolidine

EB3053: R = N-di-butyl

N$^1$-(((6-aminopyridin-3-yl)methyl)-N$^2$,N$^2$-dibutylethane-1,2-diamine, (EB3053). tert-butyl (5-(((2-(dibutylamino)ethyl)amino)methyl)pyridin-2-yl)carbamate, 286 (805 mg, 2.13 mmols) was dissolved in 5 ml of TFA. The solution was cooled and stirred at 0° C. for 2 h. The solvent was evaporated under vacuum. The residue was triturated with cold ether to leave a yellow oil residue. The crude trifluoroacetate 289 was dissolved in 5 ml of $CH_2Cl_2$, triethylamine (10 equiv) was added and the mixture stirred 15 min at room temperature. The solvent was evaporated under vacuum. The title compound was isolated by flash column chromatography on reversed phase C18 SNAP cartridge on a SPI Biotage® System using a $MeCN:H_2O$ gradient from 5% MeCN to 100% MeCN. Yield 134 mg (13%). $^1$H NMR (400 MHz, Chloroform-d) δ 8.01 (d, J=1.9 Hz, 1H), 7.47 (dd, J=8.4, 2.3 Hz, 1H), 6.51 (d, J=8.4 Hz, 1H), 4.42 (s, 2H), 3.68 (s, 2H), 2.67 (t, J=5.7 Hz, 2H), 2.58 (t, J=5.7 Hz, 2H), 2.45-2.37 (m, 4H), 1.41 (ddd, J=14.4, 8.2, 5.8 Hz, 4H), 1.29 (dq, J=14.1, 7.0 Hz, 4H), 0.92 (t, J=7.3 Hz, 6H).

Synthesis of $N^1$-((6-aminopyridin-3-yl)methyl)-$N^2,N^2$-diethylethane-1,2-diamine trifluoroacetate, (290). tert-butyl (5-(((2-(diethylamino)ethyl)amino)methyl)pyridin-2-yl)carbamate, 287 (500 mg, 1.55 mmol) was dissolved in 7.4 ml of TFA. The solution was cooled and stirred at 0° C. for 2 h. The solvent was evaporated under vacuum. The oily residue was consistent with the title compound and was used as is without further purification. Yield 521 mg (100%). $^1$H NMR (400 MHz, Methanol-$d_4$) δ 8.00 (dd, J=9.2, 2.2 Hz, 1H), 7.95 (s, 1H), 7.04 (d, J=9.2 Hz, 1H), 4.06 (s, 2H), 3.42 (d, J=6.6 Hz, 2H), 3.31-3.26 (m, 4H), 1.35 (t, J=7.3 Hz, 6H).

Synthesis of 5-(((2-(pyrrolidin-1-yl)ethyl)amino)methyl)pyridin-2-amine trifluoroacetate, 291. tert-butyl (5-(((2-(pyrrolidin-1-yl)ethyl)amino)methyl)pyridin-2-yl)carbamate, 288 (583 mg, 1.82 mmols) was dissolved in 5.8 ml of TFA. The solution was cooled and stirred at 0° C. for 2 h. The solvent was evaporated under vacuum. The oily residue was consistent with the title compound and was used as is without further purification. Yield 608 mg (100%). $^1$H NMR (400 MHz, Deuterium Oxide) δ 7.89-7.84 (m, 2H), 7.01-6.97 (m, 1H), 4.18 (s, 2H), 3.67 (d, J=14.0 Hz, 2H), 3.57-3.50 (m, 2H), 3.46 (dt, J=9.8, 3.2 Hz, 2H), 3.06 (s, 2H), 2.08 (s, 2H), 1.99-1.84 (m, 2H).

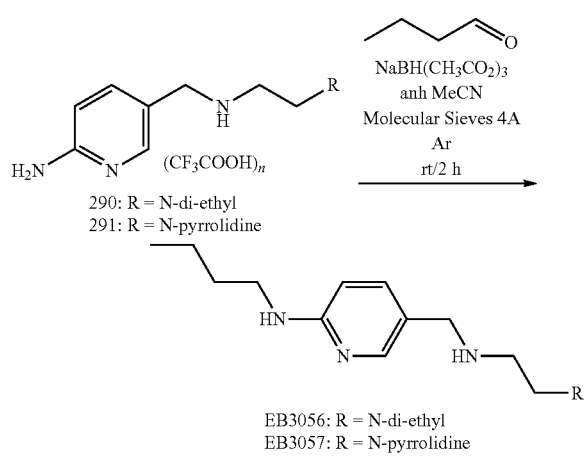

290: R = N-di-ethyl
291: R = N-pyrrolidine

EB3056: R = N-di-ethyl
EB3057: R = N-pyrrolidine

Synthesis of $N^1$-((6-(butylamino)pyridin-3-yl)methyl)-$N^2,N^2$-diethylethane-1,2-diamine, (EB3056). The title compound was prepared as described above for compound EB3060. Butyraldehyde (225 mg, 3.12 mmols) was dissolved in 25 ml of anhydrous MeCN followed by the addition of $N^1$-((6-aminopyridin-3-yl)methyl)-$N^2,N^2$-diethylethane-1,2-diamine trifluoroacetate, 290 (2.12 g, 3.12 mmols), 250 mg of 4 Å molecular sieves, sodium triacetoxyborohydride (662 mg, 3.12 mmols) and acetic acid (188 mg, 3.12 mmols). The crude mixture was separated by flash column chromatography on basic alumina using a $CH_2Cl_2$:EtOH gradient from 0% EtOH to 3% EtOH for elution. Yield 270.5 mg (31% yield). $^1$H NMR (400 MHz, Chloroform-d) δ 7.97 (d, J=1.8 Hz, 1H), 7.45 (dd, J=8.4, 2.2 Hz, 1H), 6.49 (d, J=8.4 Hz, 1H), 4.38 (s, 2H), 3.46 (s, 2H), 2.56-2.47 (m, 8H), 2.45-2.39 (m, 2H), 1.45 (ddd, J=14.8, 8.4, 6.3 Hz, 2H), 1.29 (dq, J=14.4, 7.3 Hz, 2H), 1.01 (t, J=7.2 Hz, 6H), 0.89 (t, J=7.3 Hz, 3H). $^{13}$C NMR (101 MHz, $CDCl_3$) δ 157.56, 148.25, 139.05, 125.27, 108.53, 56.03, 53.96, 51.78, 51.22, 47.57, 29.35, 20.70, 14.20, 11.90.

Synthesis of N-butyl-5-(((2-(pyrrolidin-1-yl)ethyl)amino)methyl)pyridin-2-amine, (EB3057). The title compound was prepared as described above for compound EB3060.

Butyraldehyde (159 mg, 2.2 mmols) was dissolved in 20 ml of anhydrous MeCN followed by the addition of 5-(((2-(pyrrolidin-1-yl)ethyl)amino)methyl)pyridin-2-amine trifluoroacetate, 291 (1.49 g, 3.12 mmols), 180 mg of 4 Å molecular sieves, sodium tri-acetoxyborohydride (466 mg, 2.2 mmols) and acetic acid (132 mg, 2.2 mmols). The crude mixture was separated by flash column on basic alumina using $CH_2Cl_2$:EtOH gradient from 0% EtOH to 3% EtOH for elution. Yield 156 mg (26% yield). $^1$H NMR (400 MHz, Chloroform-d) δ 7.94 (d, J=1.8 Hz, 1H), 7.43 (dd, J=8.4, 2.3 Hz, 1H), 6.47 (d, J=8.3 Hz, 1H), 4.34 (s, 2H), 3.45 (s, 2H), 2.61-2.52 (m, 4H), 2.50-2.44 (m, 4H), 2.43-2.38 (m, 2H), 1.75 (dq, J=6.7, 3.3 Hz, 4H), 1.43 (ddd, J=12.2, 8.4, 6.3 Hz, 2H), 1.27 (dt, J=15.0, 7.3 Hz, 2H), 0.86 (t, J=7.3 Hz, 3H). $^{13}$C NMR (101 MHz, $CDCl_3$) δ 157.55, 148.27, 139.06, 125.22, 108.55, 55.98, 54.68, 54.54, 53.88, 52.71, 29.28, 23.52, 20.71, 14.20.

Example 2

Compound Characterization $Ca^{2+}$ Spark Screening. Single ventricular myocytes were isolated from the hearts of 20±4 week old $RyR2^{R176Q/+}$ mice by a modified collagenase method (Li et al., *J. Vis. Exp.* 2014, 87:351357; Li et al., *Circ Res* 2012, 110:465-470; van Oort et al., *Hypertension* 2010, 55:932-8). Ventricular myocytes were loaded with the $Ca^{2+}$ indicator, Fluo-4-AM (2 μmol/l), and treated with 100 nM isoproterenol (ISO) to induce an increase in spontaneous $Ca^{2+}$ spark activity. Pre-loaded myocytes were exposed to the RyR2 inhibitor at 500 nM or untreated for 1 hour (37° C.). Inhibitors were reconstituted in DMSO to a working stock solution of 0.1M, followed by a serial dilution method to get the desired 500 nM concentration. Pre-loaded ventricular myocytes RyR2 activity was assessed to determine if the RyR2 inhibitor normalize excessive SR $Ca^{2+}$ release by measuring the $Ca^{2+}$ spark frequency (CaSpF). $Ca^{2+}$ sparks were recorded using line-scan mode with 1024 pixels per line at 500 Hz using LSM880 Zen Black confocal microscope (Carl Zeiss). 1-Hz steady-state $Ca^{2+}$ transient pacing of myocytes was induced followed by a ~10-~15 second pause during which sparks are recorded. Each inhibitor was compared to untreated negative and positive controls and repeated 2-3× (N=2-3 mice; overall containing 8-15 cells per group) to confirm accuracy of results. ImageJ software using SparkMaster plugin was used to measure the $Ca^{2+}$ spark frequency (CaSF). $Ca^{2+}$ transient amplitude (CaT) and SR load were quantified by normalizing peak fluorescence to basal fluorescence using clampfit. Data is presented as mean±SEM. Statistical significance was determined using paired or unpaired student's T-test where appropriate. Data was determined to be significant at *P<0.05 vs. untreated (control). Inhibitors that significantly reduced CaSPF (vs. untreated control) advanced to $IC_{50}$ determination.

$Ca^{2+}$ Spark $IC_{50}$ Determination. Dose-dependent inhibition of CaSPF by the RyR2 inhibitors was assessed over a range of doses (0.5 nM-5 µM) to determine the concentration necessary to normalize abnormal $Ca^{2+}$ release. Single ventricular myocytes were isolated from the hearts of 20±4 week old RyR2$^{R176Q/+}$ mice by a modified collagenase method. Ventricular myocytes were loaded with the $Ca^{2+}$ indicator, Fluo-4-AM (2 µmol/l), and treated with 100 nM ISO to induce an increase in spontaneous $Ca^{2+}$ spark activity. Pre-loaded myocytes were exposed to the RyR2 inhibitor at different dosages (0.5 nM-5 µM) and incubated for 1 hour (37° C.). Inhibitors were reconstituted in DMSO to a working stock solution of 0.1M, followed by a serial dilution method to get the desired concentration for each dose (0.5 nM-5 µM). The CaSPF dose-response data was fitted to a sigmoidal curve to determine the half-maximal inhibition concentration ($IC_{50}$). The $IC_{50}$ value obtained in this particular study corresponds to a half-maximal response for a given performance of the assay, as complete inhibition is generally not observed. The $IC_{50}$ value obtained from the sigmoidal plot was used to measure the potency in comparison to K201, a well characterized potent $Ca^{2+}$ inhibitor, based upon the equation: potency (vs K201)=$IC_{50(K201)}$/$IC_{50(compound)}$. Each compound was repeated 3× (N=3 mice) to confirm accuracy of results. The $Ca^{2+}$ spark frequency (CaSF) was assessed with ImageJ software using SparkMaster plugin. Compounds that were potent inhibitors of diastolic $Ca^{2+}$ Spark frequency but had little or no effect on the systolic $Ca^{2+}$ transient advanced to in-vivo testing.

In Vivo Screening ($ED_{50}$) at Two Escalating Doses. Intracardiac electrophysiology studies via programmed electrical stimulation were used to test the effects of the RyR2 inhibitor on the inducibility of CPVT. The drug (low dosage and high dosage, based on $IC_{50}$ values) was injected intraperitoneally in R176Q/+ mice ~15 minutes prior to programmed electrical stimulation and compared to placebo-treated R176Q/+ mice. Each compound (low and high dosage) was repeated 10× (N=10 mice) to confirm accuracy of results. The incidence of VT in the in vivo CPVT experiments at low and high doses tested is the % of animals that experience VT relative to all animals in a particular group.

Results of studies performed at the cellular level indicate that inherited mutations in RyR2, identified in patients suffering from catecholamine polymorphic ventricular tachycardia (CPVT), cause an increased susceptibility towards exercise or catecholamine-induced polymorphic ventricular arrhythmias. Likewise, mice heterozygous for mutation R176Q in RyR2 are more vulnerable to VT following catecholamine stimulation, with R176Q/+ mice exhibiting an increased incidence of isoproterenol-induced, spontaneous $Ca^{2+}$ release events. The above-discussed $Ca^{2+}$ spark assay may be used with R176Q/+ myocytes as an initial screening assay to test the ability of new compounds to inhibit spontaneous pathological SR $Ca^{2+}$ release in ventricular myocytes.

Cytotoxicity Assay. Frozen stocks of HEK293t and HepG2 cells were quickly thawed in a 37° C. water bath for culture, then cultured under 5% $CO_2$, 95% humidity conditions at 37° C. HEK293t cells were maintained in DMEM+GlutaMax-1 (Gibo, Cat #10569-010) containing 4.5 g/L D-Glucose, 110 mg/L sodium pyruvate, 10% FBS and 1× penicillin-streptomycin. HepG2 cells were maintained in DMEM (Gibo, Cat #11885-084) containing 1 g/L D-glucose, 110 mg/L sodium pyruvate, L-glutamine, 10% FBS and 1× penicillin-streptomycin. Both cell lines tested negative for mycoplasma. The cell seeding density in 96-well plate (Falcon, Cat #353219) was optimized for the AlamarBlue® dye (ThermoFisher Scientific) cell viability test. For plating in 96 well plates, 5000 cells in 200 µl media per well was selected as the seeding density for both cell lines. Cells were allowed to attach overnight after seeding, then treated with test compounds or assay control compounds for 48 h. Test compounds were serially diluted in DMSO to prepare a working solution. One µL of each compound working solution was added to 200 µl media to achieve the final test concentrations (0.005, 0.015, 0.045, 0.137, 0.41, 1.23, 3.7, 11.1, 33.3 and 100 µM). Cells were also treated with 0.5% DMSO as the vehicle control. Each compound concentration was tested in duplicate in each experiment. Two separate experiments were performed on each cell line to generate the final results. Puromycin and doxorubicin were used as assay control compounds in this study. Following 48 h incubation with test compounds, 20 µl of AlamarBlue® reagent was added directly to each well. The plates were incubated at 37° C. for 3 h. The fluorescence signal was measured by EnVision™ 2104 Multilabel Reader (PerkinElmer). Wells containing media only were included in each assay as the blank. Percent survival was calculated using the following equation. % survival was plotted versus compound concentration and $IC_{50}$ values were generated from GraphPad Prism 7 (nonlinear regression; GraphPad Software, Inc.).

$$\% \text{ survival} = \frac{\text{Signal of treated cells} - \text{blank}}{\text{Signal of vehicle} - \text{blank}} \times 100\%$$

Microsomal Stability Assay. Compound dilution: ~2 µl of compound or control from stock solution (10 mM) was diluted with 18 µl of DMSO followed by 180 µl methanol/water (v/v, 1:1) (final conc.: 100 µM); diclofenac, testosterone and propafenone were used as control compounds in this study. A working solution for each compound to be tested was prepared as follows: 20 µl from 100 µM intermediate solution was diluted with 180 µl of 100 mM potassium phosphate buffer (final conc.: 10 µM). Preparation of liver mixture and NADPH cofactor: (i) preparation of liver microsomes working solution (1.25×) (final conc.: 0.5 mg/ml); (ii) preparation of NADPH cofactor working solution (1.25×). Stop solution: a cold acetonitrile (ACN) solution including 100 ng/mi tolbutamide and 100 ng/mi labetalol as internal standards. Procedures: 10 µl of compound or control working solution/well was added to all plates (T0, T5, T10, T20, T30, T60, NCF60) except the matrix blank. 80 µl/well of microsomes solution was added to every plate, and the mixture of microsome solution and compound was incubated at 37° C. for about 10 min. 10 µl of 100 mM potassium phosphate buffer/well was added to NCF60, and incubated at 37° C. and the recording of time began. After pre-warming, 10 µL/well NADPH regenerating system was added to each plate to start reaction. The plate was incubated at 37° C. and the time recording began. 400 µl/well of the stop solution (cold acetonitrile solution at 4° C., including 100 ng/ml tolbutamide and 100 ng/ml labetalol) was added to terminate the reaction. The sampling plates were shaken for approximately 10 mM Samples were centrifuged at 4000 rpm for 20 mM 100 µl supernatant was transferred to 200 µl ultra pure water, mixed well, and the samples were analyzed by LC/MS/MS to determine compound concentration. For data analysis, first order kinetics was used to calculate $t_{1/2}$ and CL:

$$C_t = C_0 \cdot e^{-k \cdot t}$$

$$C_t = \frac{1}{2}C_0, t_{1/2} = \frac{\ln 2}{k} = \frac{0.693}{k}.$$

$$CL = Vd \cdot k.$$

$$* Vd = 2 \, ml/mg$$

Plasma Stability Assay. Species used included CD-1 mouse plasma (male-pooled), Sd rat plasma (male-pooled), and human plasma (mixed-pooled) containing EDTA-$K_2$ as an anticoagulant. The stop solution was 200 ng/mL tolbutamide, and 200 ng/mL labetalol in acetonitrile. Pooled frozen plasma was thawed for compound dilution in a water bath at 37° C. prior to use. Plasma was centrifuged at 4000 rpm for 5 minutes, and any clots were removed. The pH of the sample was measured and, if required, adjusted to 7.4±0.1. 100 µM working solutions were prepared by adding 4 µl of 10 mM stock solution to 396 µl of 45% methanol/$H_2O$. The solution was transferred to 98 µl/well of blank plasma for each time point in duplicate (0, 10, 30, 60, 120 minutes). A 2 µl aliquot of working solution (100 µM) was mixed with 98 µl of blank plasma to achieve 2 µM final concentration. Each time point sample (0, 10, 30, 60, 120 minutes) was incubated at 37° C. in a water bath. After incubation, the samples were quenched with the acetonitrile stop solution containing 200 ng/mL tolbutamide and 200 ng/mL labetalol at 1:30 ratio, mixed well on a shaker for 10 minutes, and then centrifuged at 4000 rpm for 15 minutes. 100 µL of supernatant was diluted with 100 µL of ultra-pure water for LC/MS/MS analysis. The percent remaining of test compound after incubation in plasma was calculated using the following equation:

% Remaining=100×(PAR at appointed incubation time/PAR at T0 time)

where PAR is the peak area ratio of analysis versus internal standard (IS). The appointed incubation times were T0 (0 minutes) and Tn (n=0, 10, 30, 60, 120 minutes). The half-life ($T_{1/2}$) is calculated from a log linear plot of concentration versus time.

$$C_t = \frac{1}{2}C_0, t_{1/2} = \frac{\ln 2}{k} = \frac{0.693}{k}$$

Blood-Brain Barrier (BBB) Penetration Potential. The BBB penetration potential is evaluated using MDR1-MDCK cell monolayers. MDR1-MDCK cell monolayers are grown to confluence on collagen-coated, microporous membranes in 12-well assay plates. The permeability assay buffer is Hanks' balanced salt solution containing 10 mM HEPES, and 15 mM glucose at a pH of 7.4. The buffer in the receiver chamber also contains 1% bovine serum albumin. The dosing solution concentration is 5 µM of compound in the assay buffer. Cell monolayers are dosed on the apical side (A-to-B) or basolateral side (B-to-A) and incubated at 37° C. with 5% $CO_2$ in a humidified incubator. Samples are taken from the donor and receiver chambers at 120 minutes. Each determination is performed in duplicate. The flux of lucifer yellow is also measured post-experimentally for each monolayer to ensure no damage was inflicted to the cell monolayers during the flux period. All samples are assayed by LC-MS/MS using electrospray ionization. The apparent permeability (Papp) and percent recovery are calculated as follows:

Papp=$(dCr/dt) \times Vr/(A \times CA)$

Percent Recovery=$100 \times ((Vr \times Cr^{final}) + (Vd \times Cd^{final}))/(Vd \times CN)$ where dCr/dt is the slope of the cumulative concentration in the receiver compartment versus time in µM $s^{-1}$; Vr is the volume of the receiver compartment in $cm^3$; Vd is the volume of the donor compartment in $cm^3$; A is the area of the insert (1.13 $cm^2$ for 12-well); CA is the average of the nominal dosing concentration and the measured 120 minute donor concentration in µM; CN is the nominal concentration of the dosing solution in µM; Cr' is the cumulative receiver concentration in µM at the end of the incubation period; $Cd^{final}$ is the concentration of the donor in µM at the end of the incubation period; and efflux ratio (ER) is defined as $P_{app}$ (B-to-A)/$P_{app}$ (A-to-B).

Characterizations of several exemplary compounds are shown in FIGS. 17A-17E and 18A-18E. Some of these compounds are more potent than the well-known parent inhibitor tetracaine (entry 26) and the well-known RyR inhibitor K201 (entry 28). Entry 27 is 4-MmC, an early compound of interest that provided initial proof-of concept that RyR channel modulators could become inhibitors via changes in their electronic properties. Entry 29 corresponds to a tetracaine analog exhibiting an $IC_{50}$ in the nM range. As expected, plasma stability was low due to the ester group.

Example 3

Use for Ameliorating at Least One Sign or Symptom of Cardiac Arrhythmia or Heart Failure Efficacy of the disclosed compounds for ameliorating at least one sign or symptom of a cardiac arrhythmia or heart failure in a subject may be assessed by any suitable method. Suitable assessments may include, but are not limited to, electrocardiography, echocardiography, x-ray imaging, ultrasound, use of a Holter monitor or event monitor, cardiac catheterization, coronary angiography, stress testing, blood marker analysis (e.g., BNP (brain natriuretic peptide) level, nuclear heart scan, cardiac MRI, electrophysiology study, tilt-table test, or subject-reported frequency, severity, and/or duration of cardiac arrhythmias, and combinations thereof. Thus, efficacy may be demonstrated by a reduction or cessation of heart arrhythmia symptoms (e.g., heart palpitations, fatigue, dizziness, lightheadedness, fainting or near-fainting spells, rapid heartbeat or pounding, shortness of breath, chest pain), reduction in frequency and/or duration of heart arrhythmia, and/or improving results on cardiac assessments such as those disclosed above.

In some embodiments, administration of a therapeutically effective dose of a compound as disclosed herein to a subject produces at least a 5% reduction in at least one sign or symptom of a cardiac arrhythmia or heart failure in the subject, such as at least a 10% reduction, at least a 20% reduction, at least 30% reduction, at least 40% reduction, at least 50% reduction, at least 60% reduction, at least 70% reduction, at least 80% reduction, or at least 90% reduction in at least one sign or symptom of a cardiac arrhythmia or heart failure. In certain embodiments, administration of the compound may result in complete cessation of heart arrhythmia signs or symptoms and/or normalization of one or more heart failure indicator.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, or a stereoisomer, tautomer, pharmaceutically acceptable salt, hydrate, or solvate thereof, according to the formula
wherein:

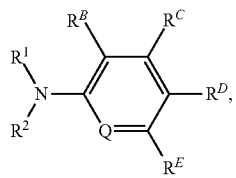

$R^B$ is H, aliphatic, —O-aliphatic, —S-aliphatic, —O—C(O)-aliphatic, or halogen;
$R^C$ is H or aliphatic;
$R^D$ is —(CR$^7_2$)$_n$-X-(CR$^7_2$)$_m$-N(R$^4$)R$^5$, —(CH$_2$)$_q$SO$_3$M, —(CH$_2$)$_q$NH$_2$, or —(CH$_2$)$_q$OH;
$R^E$ is H, —O-aliphatic, aliphatic, —S-aliphatic, —O—C(O)-aliphatic, or halogen;
Q is C-R$^3$;
X is N(R$^6$);
$R^1$ and $R^2$ independently are H or aliphatic;
$R^3$ is H, aliphatic, —O-aliphatic, or —S-aliphatic;
$R^4$ and $R^5$ independently are H, aliphatic, aryl or heteroaryl, or $R^4$ and $R^5$ together with N form a heterocycloaliphatic or heteroaryl ring;
$R^6$ is H or aliphatic;
each $R^7$ independently is H, halogen, or aliphatic;
M is a monatomic cation; and
m, n, and q independently are integers from 1 to 10,
wherein if $R^D$ is —(CR$^7_2$)$_n$X—(CR$^7_2$)$_m$—N(R$^4$)R$^5$, then at least one of the following conditions applies
(i) at least one of $R^1$ and $R^2$ is other than H, or
(ii) at least one of $R^C$ and $R^E$ is other than H, or
(iii) X is other than N(H), or
(iv) m is not 2, or
(v) n is not 1, or
(vi) if Q is CH then $R^B$ is not —O-aliphatic, or
(vii) if $R^B$ is H then Q is not C-R$^3$ where $R^3$ is —O-aliphatic, and
wherein the compound is not.

2. The compound according to claim 1, wherein $R^B$ is H, aliphatic, —O-aliphatic, —S-aliphatic, or halogen.

3. The compound according to claim 2, wherein:
$R^D$ is —(CR$^7_2$)$_n$X-(CR$^7_2$)$_m$N(R$^4$)R$^5$; and
X is N(R$^6$) where $R^6$ is aliphatic.

4. The compound according to claim 1, wherein:
(i) $R^4$ and $R^5$ are alkyl; or
(ii) m is 2, or n is 1, or m is 2 and n is 1; or
(iii) $R^6$ is H, or each $R^7$ is H, or $R^6$ is H and each $R^7$ is H; or
(iv) any combination thereof.

5. The compound according to claim 1, wherein $R^D$ is —(CH$_2$)$_q$NH$_2$, —(CH$_2$)$_q$OH, or —(CH$_2$)$_q$SO$_3$M where q is an integer from 1 to 10 and M is a monatomic cation.

6. The compound according to claim 1, wherein the compound is:
N$^1$-(4-amino-2-methoxybenzyl)-N$^2$,N$^2$-diethylethane-1,2-diamine;
3-methoxy-4-(((2-(pyrrolidin-1-yl)ethyl)amino)methyl)aniline;
sodium (4-amino-2-methoxyphenyl)methanesulfonate;
sodium (4-(dibutylamino)-3-methoxyphenyl)methanesulfonate;
sodium (4-amino-3-methoxyphenyl)methanesulfonate;
4-((2-(diethylamino)ethoxy)methyl)-2,3-dimethoxyaniline; or
N$^1$-(4-amino-3-methylbenzyl)-N$^2$,N$^2$-diethylethane-1,2-diamine.

7. A pharmaceutical composition, comprising:
a therapeutically effective amount of at least one compound according to claim 2, or a stereoisomer, tautomer, pharmaceutically acceptable salt, hydrate, or solvate thereof; and
at least one pharmaceutically acceptable additive.

8. A method, comprising:
inhibiting activity of a ryanodine receptor by contacting the ryanodine receptor with an effective amount of a compound according to claim 2, or a stereoisomer, tautomer, pharmaceutically acceptable salt, hydrate, or solvate thereof.

9. The method of claim 8, wherein contacting the ryanodine receptor comprises administering the effective amount of the compound, or stereoisomer, tautomer, pharmaceutically acceptable salt, hydrate, or solvate thereof, to a subject.

10. The method of claim 9, wherein the subject is a subject identified as having, or being at risk of having, a cardiac arrhythmia or heart failure.

11. The method of claim 8, wherein the compound is:
N$^1$-(4-amino-2-methoxybenzyl)-N$^2$,N$^2$-diethylethane-1,2-diamine;
3-methoxy-4-(((2-(pyrrolidin-1-yl)ethyl)amino)methyl)aniline;
sodium (4-amino-2-methoxyphenyl)methanesulfonate; or
any combination thereof.

12. A method for ameliorating at least one sign or symptom of a cardiac arrhythmia or heart failure, the method comprising:
administering one or more therapeutically effective doses of a compound according to claim 1, or a stereoisomer, tautomer, pharmaceutically acceptable salt, hydrate, or solvate thereof, over an effective period of time to a subject identified as having, or being at risk of having, a cardiac arrhythmia or heart failure, thereby ameliorating at least one sign or symptom of the cardiac arrhythmia or heart failure.

13. The method of claim 12, wherein the compound is:
N$^1$-(4-amino-2-methoxybenzyl)-N$^2$,N$^2$-diethylethane-1,2-diamine;
3-methoxy-4-(((2-(pyrrolidin-1-yl)ethyl)amino)methyl)aniline;
sodium (4-amino-2-methoxyphenyl)methanesulfonate; or
any combination thereof.

14. The method of claim 8, wherein the compound has a calcium spark response IC$_{50}$ value within a range of from 20 nM to 500 nM as determined in cells from a catecholaminergic polymorphic ventricular tachycardic (CPVT) mouse model.

* * * * *

UNITED STATES PATENT AND TRADEMARK OFFICE
CERTIFICATE OF CORRECTION

PATENT NO. : 11,427,542 B2
APPLICATION NO. : 17/042616
DATED : August 30, 2022
INVENTOR(S) : Thainashmuthu et al.

Page 1 of 1

It is certified that error appears in the above-identified patent and that said Letters Patent is hereby corrected as shown below:

In the Claims

In Claim 1 at Column 83, Line 56, "wherein the compound is not" should read

--wherein the compound is not 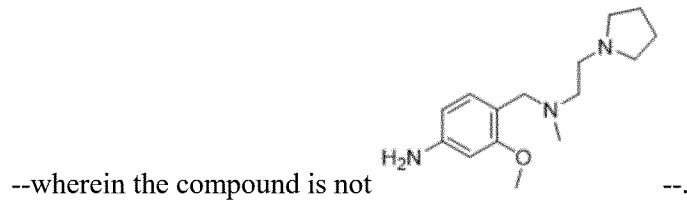 --.

In Claim 7 at Column 84, Line 20, "claim 2" should read --claim 1--.

In Claim 8 at Column 84, Line 27, "claim 2" should read --claim 1--.

Signed and Sealed this
Fourth Day of October, 2022

Katherine Kelly Vidal
*Director of the United States Patent and Trademark Office*